(12) United States Patent
de Villiers et al.

(10) Patent No.: US 8,734,519 B2
(45) Date of Patent: May 27, 2014

(54) POSTERIOR SPINAL DEVICE AND METHOD

(75) Inventors: Malan de Villiers, Gauteng (ZA); David Hovda, Mountain View, CA (US)

(73) Assignee: Spinalmotion, Inc., Mountain View, CA (US)

(*) Notice: Subject to any disclaimer, the term of this patent is extended or adjusted under 35 U.S.C. 154(b) by 368 days.

(21) Appl. No.: 11/787,110

(22) Filed: Apr. 12, 2007

(65) Prior Publication Data
US 2007/0282449 A1 Dec. 6, 2007

Related U.S. Application Data

(60) Provisional application No. 60/744,710, filed on Apr. 12, 2006, provisional application No. 60/746,731, filed on May 8, 2006, provisional application No. 60/883,493, filed on Jan. 4, 2007.

(51) Int. Cl.
*A61F 2/44* (2006.01)

(52) U.S. Cl.
USPC ............... 623/17.16; 623/17.14; 623/17.15

(58) Field of Classification Search
USPC ............................ 623/17.11–17.16
See application file for complete search history.

(56) References Cited

U.S. PATENT DOCUMENTS

| | | | |
|---|---|---|---|
| 3,486,505 A | 12/1969 | Morrison | |
| 3,867,728 A | 2/1975 | Stubstad et al. | |
| 4,309,777 A | 1/1982 | Patil | |
| 4,531,917 A | 7/1985 | Linkow et al. | |
| 4,566,466 A | 1/1986 | Ripple et al. | |
| 4,619,660 A | 10/1986 | Christiansen et al. | |
| 4,673,407 A | 6/1987 | Martin | |
| 4,759,766 A | 7/1988 | Buttner-Janz et al. | |
| 4,759,769 A | 7/1988 | Hedman et al. | |
| 4,834,757 A | 5/1989 | Brantigan | |

(Continued)

FOREIGN PATENT DOCUMENTS

| | | | |
|---|---|---|---|
| DE | 3023353 A1 | 4/1981 | |
| DE | 19710392 C1 * | 7/1999 | ............... A61F 2/44 |

(Continued)

OTHER PUBLICATIONS

Machien Translation of Specification of DE 197 10 392 C1 (published Jul. 1, 1999), performed Sep. 25, 2013 at <<espacenet.com>>.*

(Continued)

*Primary Examiner* — Michael T Schaper
(74) *Attorney, Agent, or Firm* — Wilson Sonsini Goodrich & Rosati

(57) ABSTRACT

An intervertebral joint assembly includes an upper support and a lower support, each of which has two or more components. The upper and lower support components are arranged in situ to form the upper and lower supports, respectively. By arranging the supports in situ, the supports can be introduced from the back of the patient, for example with an arthroscope. Each of the upper and lower supports has a surface adapted to engage a vertebra and a surface adapted to engage the other support or an intermediate member to form an articulate joint which articulates the joint assembly. In some embodiments, the components of the upper and lower supports are assembled in situ, for example with pivoting, telescoping or bending, to form the upper and lower supports, respectively. The supports can be attached to vertebrae with pedicles screws, and/or other anchors attached to the supports.

8 Claims, 47 Drawing Sheets

(56) References Cited

U.S. PATENT DOCUMENTS

| | | |
|---|---|---|
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,306,308 A | 4/1994 | Gross et al. |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,948 A | 11/1998 | Zuckerman et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schar et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,387,130 B1 | 5/2002 | Stone et al. |
| 6,395,032 B1 | 5/2002 | Gauchet |
| 6,402,785 B1 * | 6/2002 | Zdeblick et al. ........... 623/17.16 |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,719,794 B2 | 4/2004 | Gerber et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthan |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,852,126 B2 | 2/2005 | Ahlgren |
| 6,863,673 B2 | 3/2005 | Gerbec et al. |
| 6,875,213 B2 | 4/2005 | Michelson |
| 6,896,680 B2 | 5/2005 | Michelson |

(56) References Cited

U.S. PATENT DOCUMENTS

| | | |
|---|---|---|
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,966,931 B2 | 11/2005 | Huang |
| 6,986,788 B2 | 1/2006 | Paul et al. |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,169,182 B2 | 1/2007 | Errico et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,582 B2 | 12/2007 | Brady |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,517,363 B2 | 4/2009 | Rogers et al. |
| 7,531,001 B2 | 5/2009 | de Villiers et al. |
| 7,549,995 B2 | 6/2009 | Schultz et al. |
| 7,563,284 B2 | 7/2009 | Coppes et al. |
| 7,563,286 B2 | 7/2009 | Gerber et al. |
| 7,575,599 B2 | 8/2009 | Villiers et al. |
| 7,585,326 B2 | 9/2009 | de Villiers et al. |
| 7,637,913 B2 | 12/2009 | de Villiers et al. |
| 7,708,776 B1 | 5/2010 | Blain et al. |
| 7,708,777 B2 | 5/2010 | O'Neil et al. |
| 7,731,753 B2 | 6/2010 | Blain et al. |
| 7,731,754 B2 | 6/2010 | de Villiers et al. |
| 7,753,956 B2 | 7/2010 | de Villiers et al. |
| 8,021,429 B2 | 9/2011 | Viker |
| 8,236,058 B2 | 8/2012 | Fabian et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0028251 A1 | 2/2003 | Mathews |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0083747 A1 | 5/2003 | Winterbottom et al. |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2003/0236520 A1 | 12/2003 | Lim et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0054412 A1 | 3/2004 | Gerbec et al. |
| 2004/0059318 A1 | 3/2004 | Zhang et al. |
| 2004/0073307 A1 | 4/2004 | Keller |
| 2004/0073311 A1 | 4/2004 | Feree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0172133 A1 | 9/2004 | Gerber et al. |
| 2004/0176843 A1 | 9/2004 | Zubok et al. |
| 2004/0186569 A1 | 9/2004 | Berry |
| 2004/0186577 A1 | 9/2004 | Ferree |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1* | 12/2004 | Taylor ............... 623/17.13 |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0060036 A1 | 3/2005 | Schultz et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zuckerman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |

(56) References Cited

U.S. PATENT DOCUMENTS

| | | |
|---|---|---|
| 2005/0251262 A1 | 11/2005 | de Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0004454 A1 | 1/2006 | Ferree et al. |
| 2006/0015183 A1 | 1/2006 | Gilbert et al. |
| 2006/0020342 A1 | 1/2006 | Ferree et al. |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Feree |
| 2006/0064169 A1 | 3/2006 | Ferree et al. |
| 2006/0069439 A1 | 3/2006 | Zucherman et al. |
| 2006/0069440 A1 | 3/2006 | Zucherman et al. |
| 2006/0116768 A1 | 6/2006 | Krueger et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178744 A1 | 8/2006 | de Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0247781 A1 | 11/2006 | Francis |
| 2006/0259144 A1 | 11/2006 | Trieu |
| 2006/0259146 A1 | 11/2006 | Navarro et al. |
| 2006/0265068 A1 | 11/2006 | Schwab |
| 2006/0265077 A1* | 11/2006 | Zwirkoski .................. 623/17.16 |
| 2006/0287728 A1 | 12/2006 | Mokhtar et al. |
| 2006/0293752 A1 | 12/2006 | Moumene et al. |
| 2006/0293753 A1 | 12/2006 | Thramann |
| 2006/0293754 A1 | 12/2006 | de Villiers et al. |
| 2007/0010826 A1 | 1/2007 | Rhoda et al. |
| 2007/0021837 A1 | 1/2007 | Ashman et al. |
| 2007/0032875 A1 | 2/2007 | Blacklock et al. |
| 2007/0061011 A1 | 3/2007 | de Villiers et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | de Villiers et al. |
| 2008/0051901 A1 | 2/2008 | de Villiers et al. |
| 2008/0125864 A1 | 5/2008 | de Villiers et al. |
| 2008/0125865 A1 | 5/2008 | Abdelgany |
| 2008/0133011 A1 | 6/2008 | de Villiers et al. |
| 2008/0133017 A1 | 6/2008 | Beyar et al. |
| 2008/0154301 A1 | 6/2008 | de Villiers et al. |
| 2008/0154382 A1 | 6/2008 | de Villiers et al. |
| 2008/0215155 A1 | 9/2008 | de Villiers et al. |
| 2008/0221696 A1 | 9/2008 | de Villiers et al. |
| 2008/0228274 A1 | 9/2008 | de Villiers et al. |
| 2008/0228277 A1 | 9/2008 | de Villiers et al. |
| 2008/0294259 A1 | 11/2008 | de Villiers et al. |
| 2009/0043391 A1 | 2/2009 | de Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0192617 A1 | 7/2009 | Arramon et al. |
| 2009/0205188 A1 | 8/2009 | de Villiers et al. |
| 2009/0210060 A1 | 8/2009 | de Villiers et al. |
| 2009/0222101 A1 | 9/2009 | de Villiers et al. |
| 2009/0276051 A1 | 11/2009 | Arramon et al. |
| 2009/0326656 A1 | 12/2009 | de Villiers et al. |
| 2010/0004746 A1 | 1/2010 | Arramon |
| 2010/0016972 A1 | 1/2010 | Jansen et al. |
| 2010/0016973 A1 | 1/2010 | de Villiers et al. |
| 2010/0030335 A1 | 2/2010 | Arramon |
| 2010/0049040 A1 | 2/2010 | de Villiers et al. |
| 2010/0069976 A1 | 3/2010 | de Villiers et al. |
| 2010/0076558 A1 | 3/2010 | de Villiers et al. |
| 2010/0087868 A1 | 4/2010 | Barr et al. |
| 2010/0100141 A1 | 4/2010 | de Villiers et al. |
| 2010/0179419 A1 | 7/2010 | de Villiers et al. |
| 2010/0268344 A1 | 10/2010 | de Villiers et al. |
| 2010/0286787 A1 | 11/2010 | de Villiers et al. |

FOREIGN PATENT DOCUMENTS

| | | |
|---|---|---|
| DE | 10035182 A1 | 2/2002 |
| EP | 333990 A2 | 9/1989 |
| EP | 0333990 A3 | 5/1990 |
| EP | 560140 A1 | 9/1993 |
| EP | 560141 A1 | 9/1993 |
| EP | 591712 A1 | 4/1994 |
| EP | 0 820 740 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A2 | 9/2003 |
| EP | 1344508 A3 | 9/2003 |
| EP | 1 405 615 A1 | 4/2004 |
| EP | 1417940 A1 | 5/2004 |
| EP | 1442715 A2 | 8/2004 |
| EP | 1442715 A3 | 11/2004 |
| EP | 1 570 813 | 9/2005 |
| FR | 2 803 741 | 7/2001 |
| JP | 61-122859 | 6/1986 |
| JP | 63-164948 | 7/1988 |
| JP | 01-136655 | 5/1989 |
| JP | 06-007391 | 1/1994 |
| JP | 2002-521090 T | 7/2002 |
| JP | 2002-532144 | 10/2002 |
| JP | 2003-508119 T | 3/2003 |
| WO | WO 99/20209 | 4/1999 |
| WO | WO 99/30651 | 6/1999 |
| WO | WO 00/04851 | 2/2000 |
| WO | WO 00/35384 | 6/2000 |
| WO | WO 00/42954 | 7/2000 |
| WO | WO 00/42954 A3 | 11/2000 |
| WO | WO 01/01893 A1 | 1/2001 |
| WO | WO 01/15637 | 3/2001 |
| WO | WO 01/68003 A1 | 9/2001 |
| WO | WO 02/11650 | 2/2002 |
| WO | WO 2004/000170 | 12/2003 |
| WO | WO 2004/000171 | 12/2003 |

(56) References Cited

FOREIGN PATENT DOCUMENTS

| WO | WO 2004/026187 A1 | 4/2004 |
|----|----|----|
| WO | WO 2004/054477 | 7/2004 |
| WO | WO 2005/004756 A2 | 1/2005 |
| WO | WO 2005/004756 A3 | 1/2005 |
| WO | WO 2005/011522 A2 | 2/2005 |
| WO | WO 2005/053580 A1 | 6/2005 |
| WO | WO 2005/072662 | 8/2005 |
| WO | WO 2005/112834 | 12/2005 |
| WO | WO 2005/112834 A3 | 5/2006 |
| WO | WO 2006/119092 A2 | 11/2006 |
| WO | WO 2006/119092 A3 | 11/2006 |
| WO | WO 2005/011522 A3 | 1/2007 |
| WO | WO 2007/121320 | 10/2007 |
| WO | WO 2007/121320 A3 | 6/2008 |
| ZA | 03/9312 | 11/2003 |

OTHER PUBLICATIONS

Buttner-Janz, "The Development of the Artificial Disc," Introduction, pp. 1-18, Library of Congress Catalogue No. 92-75582, ISBN 0-9635430-0-8 (1989).

Hellier, et al., "Wear Studies for Development of an Intervertebral Disc Prosthesis," *Spine*, vol. 17 No. 6 Supplement pp. 86-96 (1992).
Lee, et al., "Impact Response of the Intervertebral Disc in a Finite-Element Model," *Spine* vol. 25, No. 19, pp. 2431-2439.
Lehuec et al., "Shock Absorption in Lumber Disc Prosthesis," Journal of Spinal Disorders & Techniques, vol. 16, No. 4, pp. 346-351.
International Search Report of PCT Application No. PCT/US05/26160, dated Jul. 21, 2005.
International Search Report of PCT Application No. PCT/US06/002263, dated Jul. 27, 2007.
International Search Report and Written Opinion of PCT Application No. PCT/US07/66564, Apr. 15, 2008, 6 pages.
European search report and opinion dated Sep. 26, 2011 for EP Application No. 07760593.9.
Office action dated Jan. 5, 2010 for U.S. Appl. No. 12/025,561.
Office action dated Feb. 1, 2012 for U.S. Appl. No. 12/827,852.
Office action dated May 29, 2012 for U.S. Appl. No. 12/841,717.
Office action dated Jun. 6, 2012 for U.S. Appl. No. 12/827,852.
Office action dated Jun. 16, 2009 for U.S. Appl. No. 12/025,561.
Office action dated Dec. 7, 2011 for U.S. Appl. No. 12/841,717.

* cited by examiner

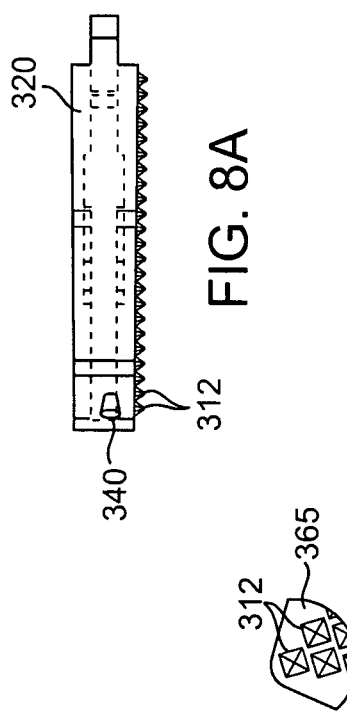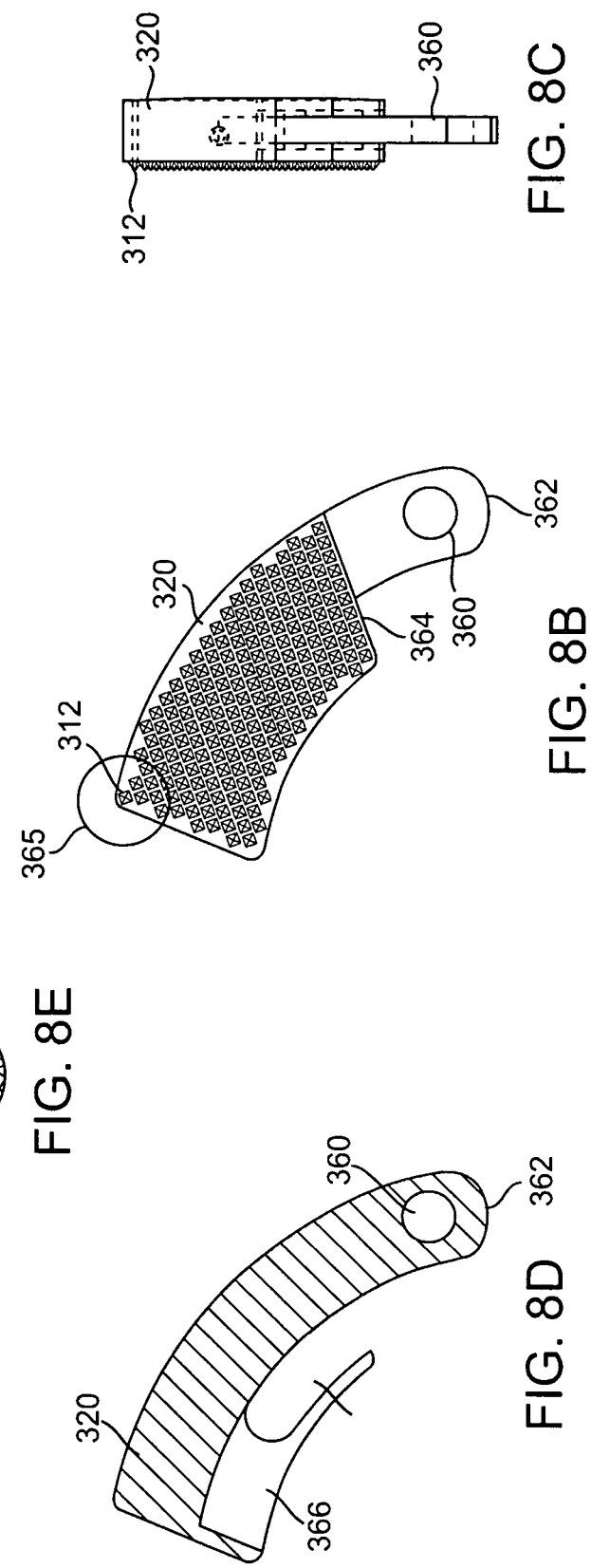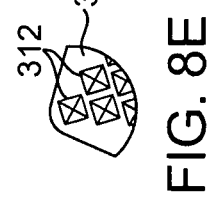

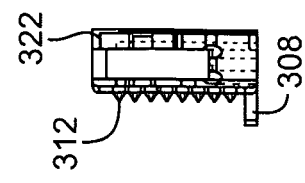
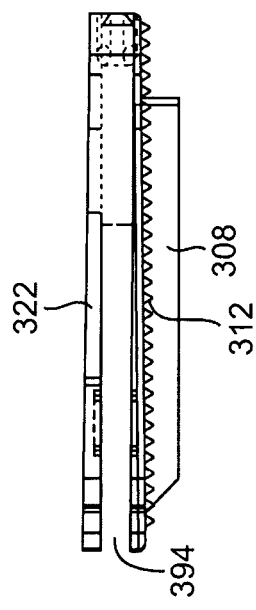
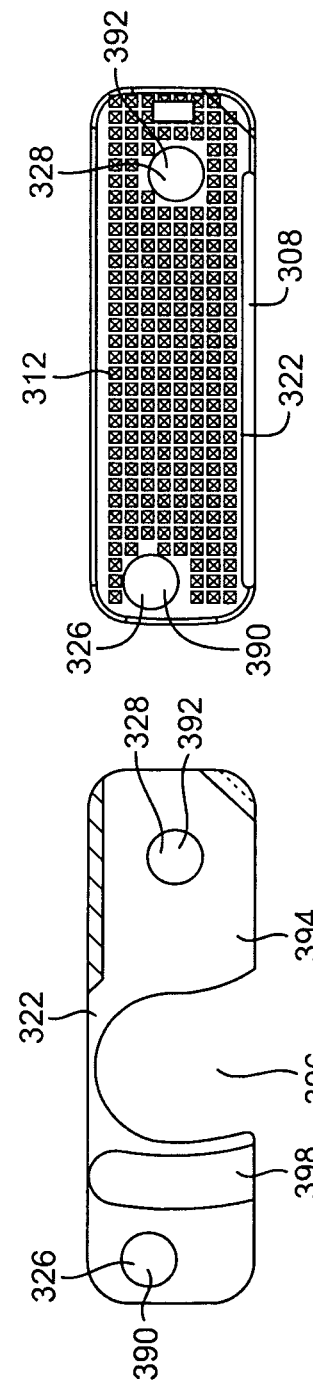
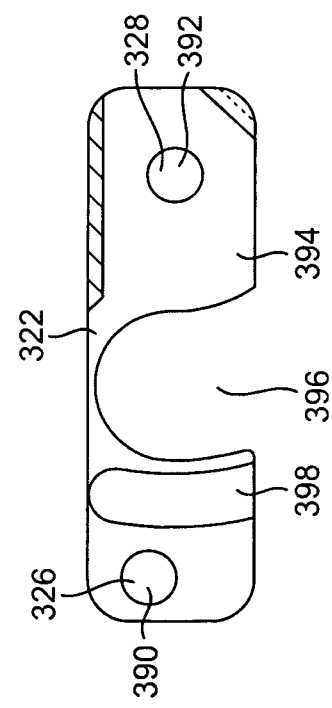

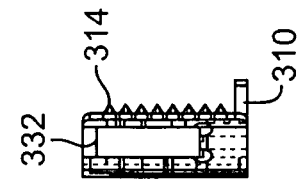
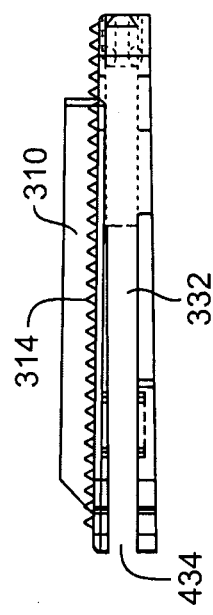
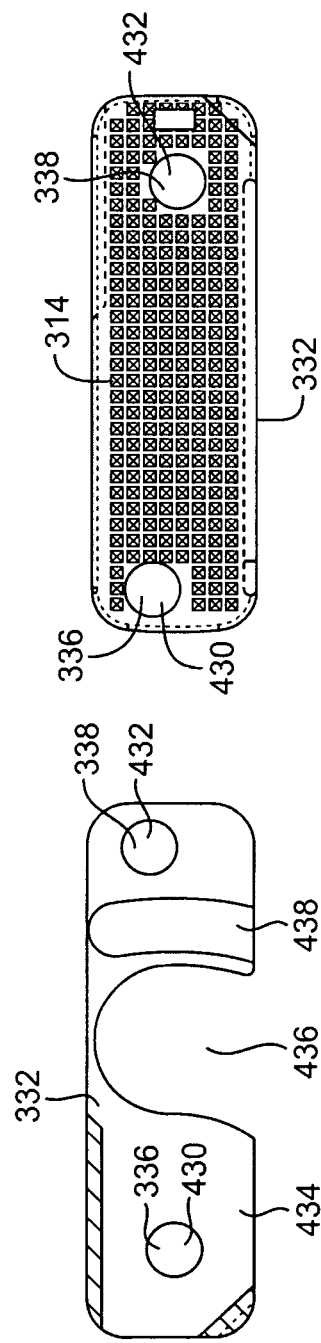
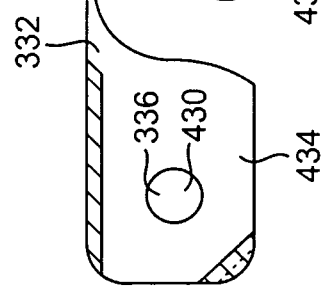

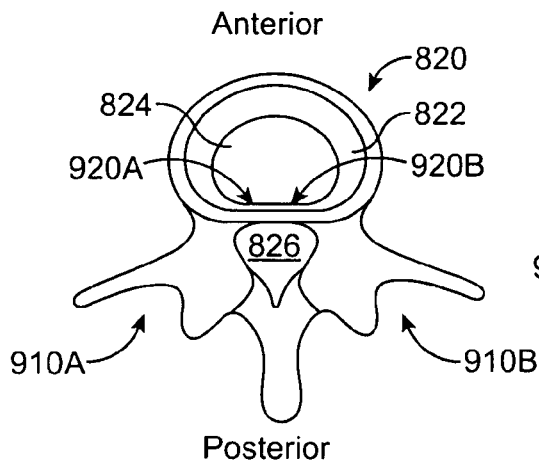
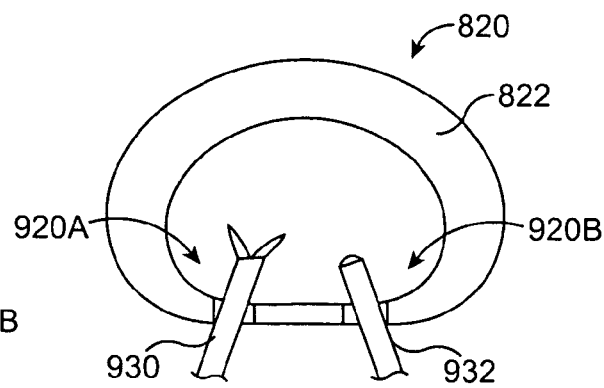
FIG. 22A    FIG. 22B
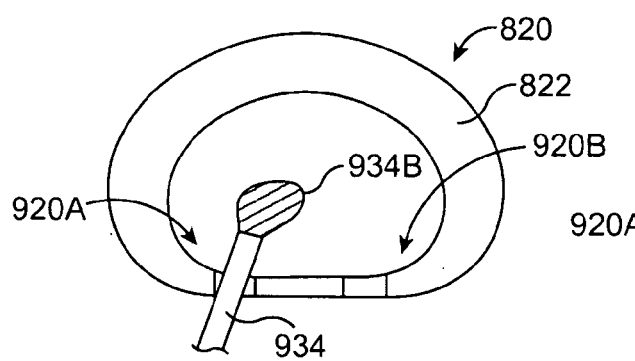
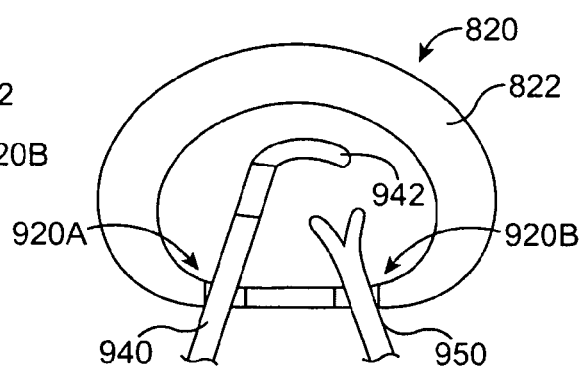
FIG. 22C    FIG. 22D
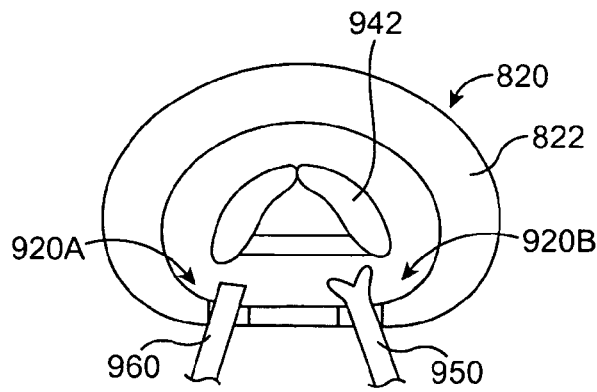
FIG. 22E

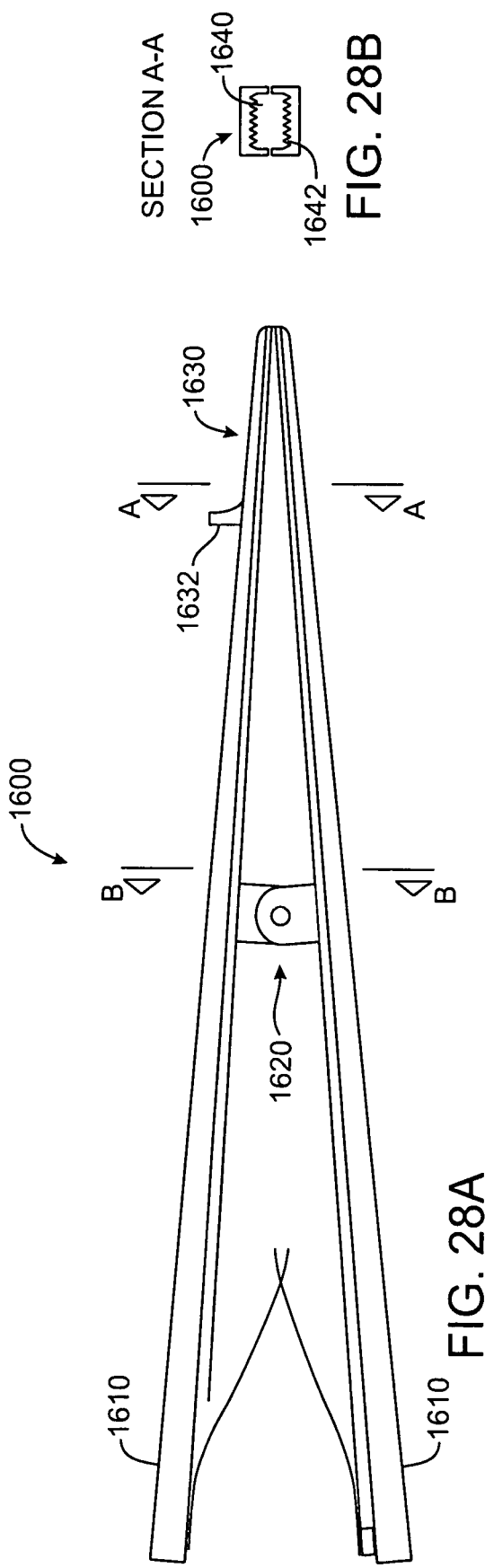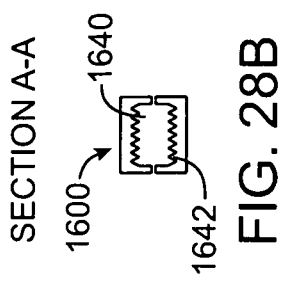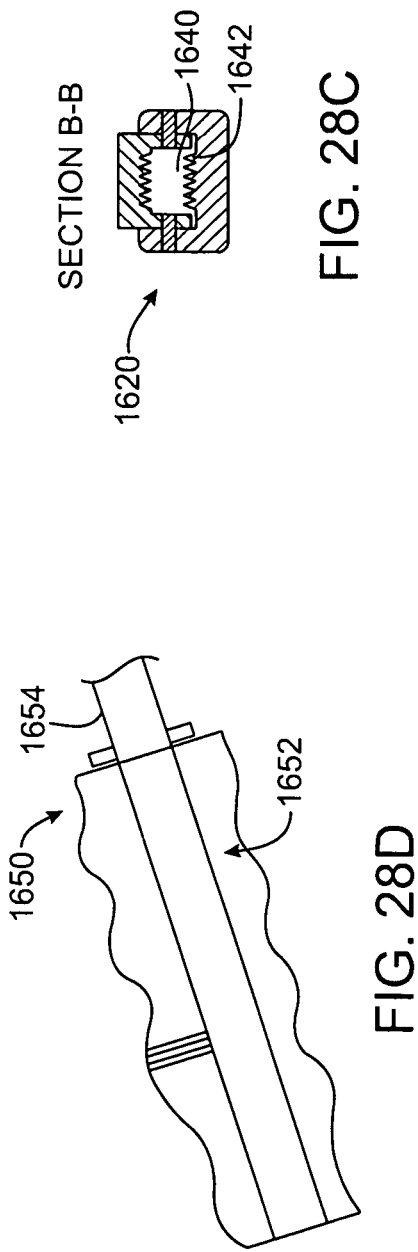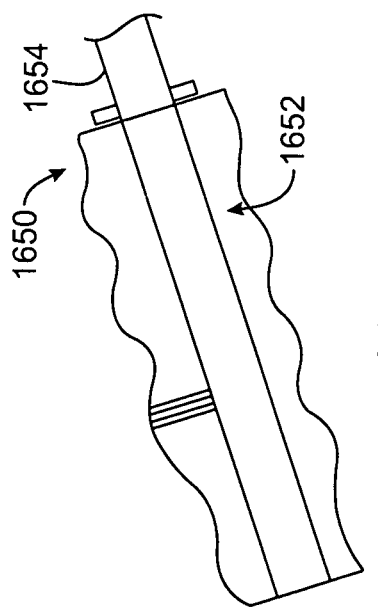

POSTERIOR SPINAL DEVICE AND METHOD

CROSS REFERENCE TO RELATED APPLICATIONS

The present application claims priority from the following provisional applications: U.S. Appl. No. 60/744,710, filed Apr. 12, 2006, entitled "Spinal Disk Arthroscopy"; U.S. Appl. No. 60/746,731, filed May 8, 2006, entitled "Spinal Disk Arthroscopy"; U.S. Appl. No. 60/883,493, filed on Jan. 4, 2007, entitled "Spinal Disk Arthroscopy"; the full disclosures of which are incorporated herein by reference.

The disclosure of the present application is related to those of U.S. application Ser. No. 10/855,253, filed May 26, 2004, entitled "Prosthetic Disc for Intervertebral Insertion" U.S. Publ. No. 2005/0021145 ; U.S. application Ser. No. 10/913,780, filed Aug. 6, 2004, entitled "Methods and Apparatus for Intervertebral Disc Prosthesis Insertion"; U.S. application Ser. No. 11/187,733, filed Jul. 21, 2005, entitled "Intervertebral Prosthesis Placement Instrument"; U.S. application Ser. No. 10/903,913, filed Jul. 30, 2004, entitled "Intervertebral Prosthetic Disc with Metallic Core", U.S. Publ. No. 2006/0025862 ; U.S. Appl. No. 60/820,769, filed on Jul. 28, 2006, entitled "Spinal Prosthesis with Offset Anchors", U.S. Appl. No. 60/820,770, filed on Jul. 28, 2006, entitled "Spinal Prosthesis with Multiple Pillar Anchors" the full disclosures of which are incorporated herein by reference.

BACKGROUND OF THE INVENTION

1. Field of the Invention

This invention relates to medical devices and methods. More specifically, the invention relates to a prosthetic disc for intervertebral insertion, such as in the lumbar and cervical spine. The invention also relates to the replacement of zygophyseal joints.

In the event of damage to a lumbar or cervical intervertebral disc, one possible surgical treatment is to replace the damaged disc with an intervertebral disc prosthesis. Several types of intervertebral disc prostheses are currently available. One type available under the trademark LINK.®™ SB Charite (Waldemar Link Gmbh, Hamburg, Germany), includes upper and lower prosthesis plates or shells which engage the adjacent vertebral bodies with a low friction core between the plates. [See EP 1142544A1 and EP 1250898A1] A potential drawback of that design is that the prosthetic device must be inserted from the anterior side of the patient, and this approach can be difficult and may require a vascular surgeon as the prosthetic devices passes near important blood vessels located anterior to the spine. Other currently available intervertebral disc prostheses usually have similar drawbacks, including invasiveness of the surgery and/or surgical skill and complexity.

Another prosthetic approach has been to fuse the vertebrae, for example with transforaminal lumbar interbody fusion (TLIF) surgery or posterior lumbar interbody fusion (PLIF) surgery. Fusion surgery generally requires at least partial removal of one or more facet joints, bone grafting, and support with a fusion cage to stop the motion at that segment. Although the fusion cages can be inserted from the back of the patient, such prostheses generally do not provide a flexible joint at the damaged disc site or other implant site. Thus a potential disadvantage of these fusion approaches is that motion is not restored.

In light of the above, it would be desirable to provide improved prostheses, particularly less invasive surgical prostheses which at least partially restore motion.

2. Description of the Background Art

Published U.S. patent applications 2002/0035400A1 and 2002/0128715A1 describe disc implants which comprise opposing plates with a core between them over which the plates can slide. Other patents related to intervertebral disc prostheses include U.S. Pat. Nos. 4,759,766; 4,863,477; 4,997,432; 5,035,716; 5,071,437; 5,370,697; 5,401,269; 5,507,816; 5,534,030; 5,556,431; 5,674,296; 5,676,702; 5,702,450; 5,824,094; 5,865,846; 5,989,291; 6,001,130; 6,022,376; 6,039,763; 6,139,579; 6,156,067; 6,162,252; 6,315,797; 6,348,071; 6,368,350; 6,416,551; 6,592,624; 6,607,558; 6,706,068 and 6,936,071. Other patent applications related to intervertebral disc prostheses include U.S. Patent Application Publication Nos.: 2003/0009224; 2003/0074076; 2003/0191536; 2003/0208271; 2003/0135277; 2003/0199982; 2001/0016773 and 2003/0100951. Other related patents include WO 01/01893A1, WO 2005/053580, EP 1344507, EP 1344506, EP 1250898, EP 1306064, EP 1344508, EP 1344493, EP 1417940, EP 1142544, and EP 0333990.

BRIEF SUMMARY OF THE INVENTION

The present invention provides an implanted intervertebral joint assembly which both restores motion and can be implanted from the back of the patient, thereby decreasing the invasiveness of the procedure, for example with a smaller posterior surgical incision avoiding important blood vessels located anterior to the spine. Components of the assembly are usually introduced to the surgical site through an incision, in some instances aided with an arthroscope (or other viewing device), and assembled in situ to form an upper support and a lower support. Each of upper and lower supports has a surface adapted to engage a vertebra and a surface adapted to engage the other support or an intermediate member to form an articulate joint which articulates the supports. The upper and lower supports usually include bone anchors and/or structures to receive anchoring screws to anchor the supports to the vertebrae. The intervertebral joint assembly with formed supports is implanted between vertebrae to replace a damaged disc or damaged zygophyseal joint, thereby providing an articulate prosthesis at the implant site.

The components can be assembled, formed and arranged in many ways to form the supports in situ. For example, the upper and lower supports can be formed by injecting a bladder with a polymer or by deformation of a metal as with stents. Typically, the upper and lower supports will be shaped as rings, discs, triangles, polygons or the like, and the components will be a segment or portion of the support so that assembly of the components forms the support. For example, in the case of rings, the components may each be an arc of the ring, with no one arc spanning more than 180 degrees. Thus, there will be at least two ring components, more often at least three or more ring segments. The segments may be joined in a variety of ways. In the illustrated embodiments shown below, the segments are joined by pivots, but in other embodiments the components could be joined by springs, fasteners, coaxial (telescoping) sleeves, linkages, or the like. In still other embodiments, the components could be unjoined prior to implantation and joined by coupling members, screws, adhesives, or in other ways after introduction into the patient.

In one aspect the present invention comprises an intervertebral joint assembly comprising an upper support and a lower support. The supports each have two or more components which can be arranged in situ to form the supports, so that the invasiveness of the surgery is minimized. The upper support has a lower surface and the lower support has an upper surface. The upper and lower surfaces are adapted to engage each other or an intermediate member to form an articulate joint, thereby restoring at least some motion between vertebrae when the assembly is positioned between vertebrae. Although the intermediate member often comprises biconvex spherical surfaces, any combination of surfaces can be used including plano/concave, plano/convex and biconcave surfaces. While the member is preferably made of metal such as cobalt chrome, the member can be made of biocompatible polymer. For embodiments without an intermediate member in which the upper and lower surfaces of the supports directly engage each other, the engagement surfaces are typically concave and convex, and while the surfaces are preferably formed in metal such as cobalt chrome, the surfaces can be formed in any biocompatible material, for example polymer.

The supports will have surfaces adapted to engage the adjacent vertebrae and facilitate insertion of the assembly into the intervertebral space. Usually, the surfaces will be flat, although they may be modified or slightly shaped to conform to the vertebrae. In the illustrated embodiments, the two or more components will assemble to form an upper flat surface to engage an upper vertebra. Similarly, the two or more components of the lower support will assemble to form a lower flat surface to engage the upper surface of a lower vertebra.

In some embodiments, the vertebrae engagement surfaces may have anchors and/or other structures to attach and anchor the supports to the vertebrae. For example, at least one component of the upper support includes at least one structure which is adapted to anchor the support in an upper vertebra, for example an anchor or hole adapted to receive an anchoring screw; and/or at least one component of the lower support includes at least one structure which is adapted to anchor the support in a lower vertebrae, for example an anchor or hole adapted to receive an anchoring screw. Various sizes and shapes of anchors can be used. For example, the anchor(s) can comprise an elongate anchor, or fin, adapted to enter a groove formed in a vertebra while the assembly is inserted into an intervertebral location. Also, the anchor may comprise a protrusion having a tip adapted to engage the surface of the vertebrae, for a example a tip at the end of a pyramidal protrusion or a tip at the end of a conic protrusion. Additional anchors can be attached to each of the components. For example, at least two components of the upper support can comprise one or more anchors adapted to anchor the upper support in the upper vertebrae and/or at least two components of the lower support can comprise one or more anchors adapted to anchor the lower support in the lower vertebrae. Alternatively or in addition to anchors, at least one of the support components can include a structure, for example a hole, adapted to receive an anchoring screw. Anchoring screws can be used instead of elongate anchors to attach the supports to the vertebrae. For example, the use of anchoring screws can permit adjustment to the position of the joint assembly after the joint assembly is inserted in the intervertebral space because the screws can be attached after the joint assembly is positioned at the desired final position within the intervertebral space.

Any number of appropriately arranged components can be assembled to form the supports. For example, each support can comprise three or more components with each component having a first end and a second end which mechanically couple the components arranged to form the supports. To provide stability to the assembly, the engagement surfaces of the articulate joint can be located at least partially within a bounded area on each support defined by locations where the components are coupled, for example a triangular bounded area defined by three joints located near the ends of three interlocking components.

In the illustrated embodiments, the components of the supports are pivotally attached (hinged) so that they can be assembled in situ to form the support by unfolding the components at a surgical site. For example, the components can be adapted to fold or collapse to a narrow profile, usually straight, configured for introduction to a surgical site. After introduction, the structure can be pivoted and/or unfolded to form the first support at the surgical site. This process can be repeated to form the second support at the surgical site. In another embodiment, both supports are unfolded simultaneously. Such an "elongate" arrangement of components allows a smaller incision to be used, and in some instances allows the implant to be introduced with an arthroscope or other viewing devices. While assembly of the components to form the supports can be accomplished in many ways, assembly of the components can include at least one of pivoting, telescoping or bending the components. In an embodiment, one or more supports comprise three components: a distal component, a middle component and a proximal component, and at least one of the three components includes an elongate anchor adapted to enter a groove formed in a vertebra. Alternatively, at least one of the three components includes a hole to receive an anchoring screw.

Articulation of the upper and lower supports can be achieved in any number of ways. For example, the lower surface of the upper support can comprise a convex or concave feature, and the upper surface of the lower support can comprise a concave or convex feature which mates the feature on the upper support. Alternatively, an intermediate member comprising first and second curved surfaces, or a first curved surface and a second flat surface, can be positioned between the supports so that the first and second surfaces engage the upper and lower supports, respectively. Preferably, the intermediate member is allowed to move freely, or float, between both surfaces of the two supports. Alternatively, the intermediate member can be held rigidly against one of the supports while allowed to slide along the other support to articulate the supports.

In many embodiments the upper support comprises an upper support ring and a the lower support comprises a lower support ring, usually including an outer circular periphery and an open interior. The upper ring can include two or more separable components. The upper ring components can be introduced in a disassembled condition and joined in situ to form the upper ring. The lower ring can include two or more separable components. The lower ring components can be introduced in a disassembled configuration and joined in situ to form the lower ring. The upper ring may have a lower surface and the lower ring may have an upper surface. The upper and lower surfaces can be adapted to permit the rings to articulate.

In some embodiments the lower surface of the upper ring may include a convex or concave feature, and the upper surface of the lower ring may include a concave or convex feature which mates the feature on the upper ring. In further embodiments the upper and lower rings can separate into at least two arcuate sections. In other embodiments, the upper and lower rings can separate into at least three arcuate sections. In yet other embodiments bone anchors may hold the rings in place. For example, external posts having elongate shafts can be used to attach the rings to the bone anchors, and the elongate shafts can mate with the bone anchors and/or the rings.

In another aspect the present invention comprises a method for introducing a joint assembly to an intervertebral space between a pair of vertebral bodies. The upper support components are introduced. The upper components are arranged in situ into an upper support. The lower support components are introduced to the intervertebral space. The lower support components are arranged into a lower support. The support surfaces are arranged to articulate.

In some embodiments the support components are introduced from the back of the patient (i.e. posteriorly). The upper support and/or the lower support can be attached to bone anchors to provide additional support, and external posts can be used to attach the bone anchors to the upper support and/or the lower support. The components of the upper and lower supports can be introduced and arranged together. The components of each support can be arranged by pivoting one or more components on each support from a first narrow profile arrangement to a second wide profile arrangement. For example, at least one gear one each support can be rotated to pivot the one or more components of each support.

In many embodiments a method for assembling an intervertebral prosthesis in situ within a patient comprises introducing components of the intervertebral prosthesis into the patient in a narrow profile arrangement. The components at least one gear is rotated to pivot the components from the narrow profile arrangement to a wide profile arrangement to assemble the prosthesis.

In specific embodiments, the components of the prosthesis are retained by a placement instrument while the components are introduced in the narrow profile configuration. The at least one gear can be disposed on one or more of the components and engaged by a rack disposed on the placement instrument so that the at least one gear rotates while the components are advanced distally and/or the rack is retracted proximally.

In another aspect, the present invention provides an instrument for introducing a joint assembly to an intervertebral space between a pair of vertebral bodies. The instrument comprises a shaft and a cartridge to retain the joint assembly. The cartridge is coupled to the shaft. The cartridge comprises a structure to engage the intervertebral joint assembly and pivot at least one component of the intervertebral joint assembly.

In specific embodiments, the structure comprises at least one of a rack or a gear to engage the intervertebral joint assembly. The cartridge comprises a casing. The casing can be shaped to at least partially cover the joint assembly and permit the joint assembly to slide relative to the casing. The casing can be shaped to hold upper and lower components of the joint assembly together and limit movement while the casing at least partially covers the joint assembly. The cartridge can comprise an inner part shaped to fit at least partially within the casing and move relative to the casing. The shaft can comprise threads to advance the inner part and/or retract the casing. The inner part can comprise a protrusion to extend between components of upper and lower support components of the joint assembly and limit movement. The protrusion can comprise a wedge with proximally inclined opposing surfaces and opposed flanges to limit movement between upper and lower support components of the joint assembly.

In many embodiments an intervertebral joint assembly comprises an upper support having a lower surface in which the upper support comprises two or more components and at least one gear to arrange the components. The upper support components may be arranged in situ with rotation of the at least one gear on the upper support to form the upper support. A lower support has an upper surface and comprises two or more components and at least one gear to arrange the components. The lower support components may be arranged in situ with rotation of the at least one gear on the lower support to assemble the lower support. The upper and lower surfaces are adapted to engage each other or an intermediate member to form an articulate joint.

In specific embodiments, the at least one gear on each support can be connected to the at least one of the components of each support so that rotation of the at least one gear pivots the at least one component. The at least one gear on each support can be fixed to the at least one component. Each support can comprise three or more components and at least two gears to arrange the three or more components. The two or more components of each support can be connected with a joint, and rotation of the at least one gear on each support may pivot at least one of the two or more components about the joint. An axis of rotation of the at least one joint can be aligned with an axis of rotation of the at least one gear. Each surface may be formed in a protrusion extending from each support. The at least one gear on each support may comprise an annular shape disposed around the protrusion on each support. Each protrusion may comprise a flange that extends toward the intermediate member to retain the member. In addition or in combination, each protrusion may comprise a retention element that extends at least partially over the at least one gear to retain the at least one gear while the gear rotates around the protrusion. Each protrusion can extend from the component on each support to an annular rim, and at least one annular rim can comprise a bevel to limit articulation between the upper support and the lower support to a pre-determined angle.

In many embodiments, an intervertebral prosthesis is provided. The prosthesis comprises a first support adapted to expand from a narrow profile to an expanded profile while in the intervertebral space. A second support is adapted to expand from a narrow profile to an expanded profile while in the intervertebral space. The first and second supports are adapted to engage each other or an intermediate member to articulate while in the expanded configurations.

In many embodiments, the prosthesis comprises anchors adapted to permit stacking with another prosthesis positioned in an adjacent intervertebral space. In specific embodiments, the first support and the second support articulate with at least one of a flexion/extension, a lateral bending, an axial rotation or a lateral translation.

In another aspect, a method of articulating between adjacent vertebrae is provided. The method comprises inserting an intervertebral prosthesis into an intervertebral space between the adjacent vertebrae. The intervertebral prosthesis is expanded from a narrow profile configuration to an expanded configuration. The prosthesis articulates the vertebrae in the expanded configuration.

In specific embodiments, the prosthesis is inserted into the intervertebral space from a posterior lateral approach. The posterior lateral approach may substantially comprise a Wiltse approach. Tissue can be dissected with a blunt instrument along the posterior lateral approach. An access opening from about 7 to 15 mm across may be formed along the posterior lateral approach. In many embodiments, the facet joints of the adjacent vertebrae remain substantially intact after insertion of the prosthesis into the intervertebral space.

In many embodiments, a method of articulating adjacent vertebrae is provided. The method comprises penetrating a spinal disc annulus located between the adjacent vertebrae to form an opening in the spinal disc annulus. A spinal prostheses can be inserted in a narrow profile configuration through the opening. The spinal prosthesis can be expanded inside the annulus from the narrow profile configuration to an expanded profile configuration. The spinal prosthesis can articulate the vertebrae while in the expanded configuration.

In specific embodiments, the spinal disc annulus is penetrated to form another opening away from the opening. A distraction tool is inserted through the another opening to distract the adjacent vertebrae. The vertebrae can be distracted with the distraction tool while the prosthesis is inserted through the opening.

In many embodiments, a method of removing an expandable prosthesis from an intervertebral space is provided. The method comprises collapsing the expandable prosthesis from an expanded configuration to a narrow profile configuration while the prosthesis is positioned in the intervertebral space. The expandable prosthesis is removed from the intervertebral space in the narrow profile configuration.

In many embodiments, the expandable prosthesis can be removed from a removal opening formed to remove the expandable prosthesis. In specific embodiments, the expandable prosthesis can be removed from an insertion opening formed to insert the expandable prosthesis.

In many embodiments, a method of preparing an intervertebral space for a prosthesis is provided. The method comprises removing material from the intervertebral space. An expandable member is inserted into the intervertebral space to evaluate the intervertebral space.

In specific embodiments, additional material is removed in response to the evaluated intervertebral space. The expandable member may comprise at least one of a balloon or a template.

In many embodiments, a method of positioning a prosthesis in an intervertebral space is provide. The method comprises inserting a first instrument through a first surgical opening to contact the prosthesis at a first location. A second instrument can be inserted through a second surgical opening to contact the prosthesis at a second location. A position of the prosthesis can be adjusted with the first instrument and the second instrument.

In specific embodiments, the second surgical opening comprises a contra-lateral opening. The second instrument may be connected to the prosthesis.

In another aspect, a prosthesis assembly for insertion into an intervertebral space is provided. The prosthesis assembly comprises a first end portion adapted to attach to a first instrument while the prosthesis assembly is positioned in an intervertebral space. A second end portion is adapted to attach to a second instrument while the prosthesis assembly is positioned in the intervertebral space.

In specific embodiments, at least one of the first end portion or the second end portion comprises a spacer adapted for removal from the prosthesis. The prosthesis assembly may be expandable from a first narrow profile configuration to a second expanded configuration, and the prosthesis assembly may comprise a locking mechanism to lock components of the prosthesis assembly in the expanded configuration.

In many embodiments, an instrument for introducing a prosthesis into an intervertebral space between a pair of vertebral bodies is provided, the instrument comprises a shaft. A structure is connected to the shaft near the end of the shaft. The structure can be adapted to retain the joint assembly while the joint assembly is advanced into the intervertebral space such that components of the prosthesis pivot from a narrow profile configuration to an expanded profile configuration while the prosthesis is advanced into the intervertebral space.

In specific embodiments, the structure may comprise at least one of casing or a spacer to limit movement of the components while the components pivot from the narrow profile configuration to the expanded profile configuration. The structure may comprise a spacer attached to the components of the prosthesis.

BRIEF DESCRIPTION OF THE DRAWINGS

FIGS. 8A-8E show the distal support component of the upper support of FIGS. 5 and 6A-6D.

FIGS. 10A-10D show the proximal support component of the upper support of FIGS. 5 and 6A-6D.

FIGS. 13A-13D show the proximal support component of the lower support of FIGS. 5 and 6A-6D.

FIGS. 22A to 22E show a method for introducing a joint assembly into an intervertebral disc space, in accordance with embodiments of the present invention.

FIGS. 28A to 28D show a placement instrument as in FIGS. 27A to 27C, according to embodiments of the present invention.

DETAILED DESCRIPTION OF THE INVENTION

The present invention is generally directed to replacement of spinal disc and zygophyseal joints, for example joints between facets of inferior and superior articular processes of adjacent vertebra. By providing components which can be assembled in situ to form supports, the surgical site can be accessed from the back or posterior side of the patient. This access to the surgical site from the posterior side of the patient can be easier to perform. For example where access to the surgical site avoids important arteries and/or veins, the presence of a vascular surgeon may not be necessary.

Figure 1:
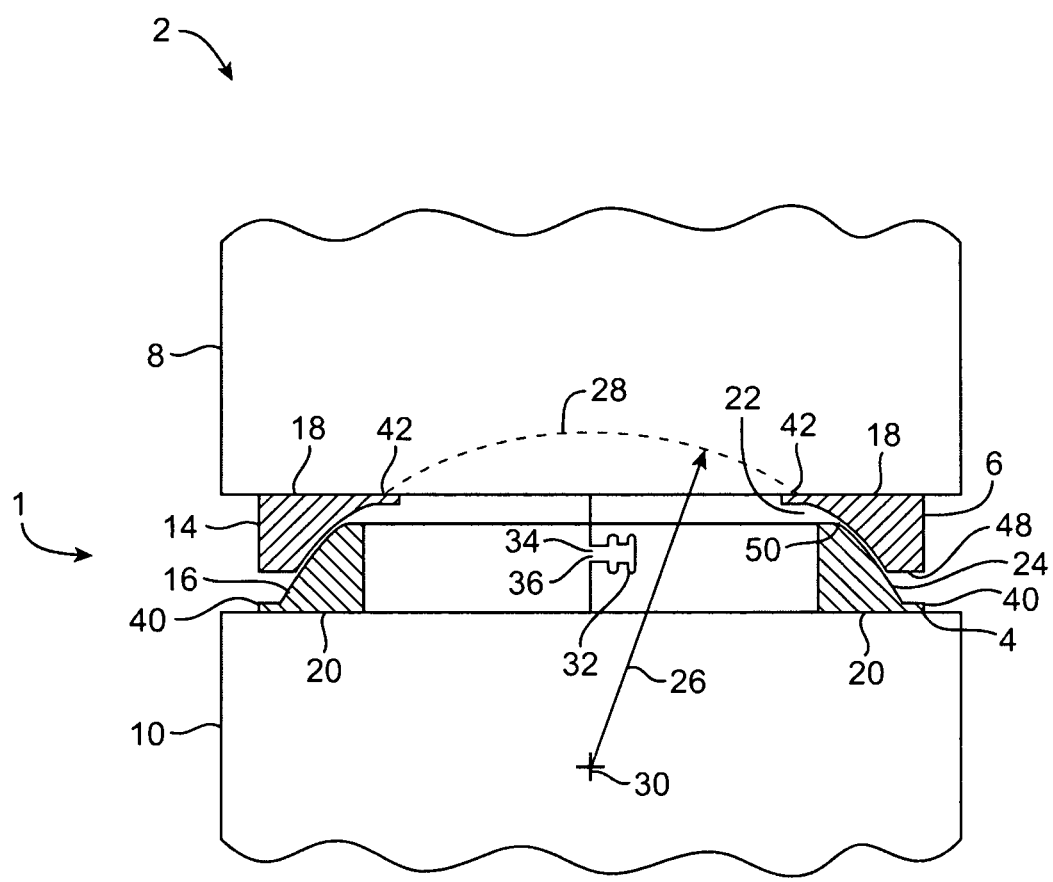
FIG. 1 shows a cross sectional side view of an intervertebral joint assembly.

FIG. 1 illustrates an intervertebral joint assembly 1 for insertion into a spine 2 of a patient. The joint assembly can include an inferior endplate 4 and a superior end plate 6. The joint assembly can be inserted between two adjacent spinal vertebrae, for example a superior vertebra 8 and an inferior vertebra 10. Joint assembly 1 includes a superior component such as an upper ring 14 and an inferior component such as a lower ring 16. Upper ring 14 can be formed from separable components 18 by joining separable components 18 in situ. Lower ring 16 can be formed from separable components 20 in situ. In situ formation of upper and lower rings 14 and 16 generally includes forming the ring with at least a portion of the ring between superior vertebra 8 and inferior vertebra 10. Separable components 20 can be joined with a locking mechanism 36. The locking mechanism includes a first interlocking segment, such as channel 32, and second interlocking segment, such as key 34, generally in the appearance of a lock and key mechanism. Upper ring 14 can include superior plate 6, and lower ring 16 can include inferior plate 4. The end plates can attach the rings to the vertebrae with fins and or serrations as described in U.S. application Ser. No. 10/855,253, filed May 26, 2004, entitled "Prosthetic Disc for Intervertebral Insertion", U.S. Pub. No. 20050021145, the full disclosure of which has been previously incorporated herein by reference. Upper ring 14 has a lower surface 22, and lower ring 16 has an upper surface 24 Lower surface 22 is formed with a feature such as radius of curvature 26. Upper surface 24 is formed with the feature such as radius of curvature 26 so that the upper and lower surfaces mate. For example, as both the upper surface 24 and the lower surface 22 are formed to a spherical shape having radius of curvature 26, the surfaces mate and move along a spherical surface of articulation 28. The spherical surface of articulation has a center 30. As shown in FIG. 1. the center of the surface of articulation is located in the inferior vertebra 10, and upper surface 24 is convex while lower surface 22 is concave. In an alternate embodiment, center 30 of surface of articulation 28 can be located in the superior vertebra 8, and upper surface 24 concave while lower surface 22 is convex. In alternate embodiments, the upper and lower surfaces can be formed with a mating feature which is not the surface of a sphere, such as an outer surface of a doughnut, or torus. Lower ring 16 can include a lower flange 40 which limits motion of the rings over the surface of articulation. A portion 48 of upper ring 14 can be formed to receive lower flange 40 formed in lower ring 16, thereby limiting motion of the upper and lower rings. Upper ring 18 can include an upper flange 42 which limits motion of the rings over the surface of articulation. A portion 50 of lower ring 16 can be formed to receive upper flange 42, thereby limiting motion of the upper and lower rings. The components of the joint assembly can be made from any suitable biocompatible material including Titanium, Cobalt Chrome. In particular, it may be desirable to coat a Cobalt/Chrome surface with Titanium where the plates meet with the vertebrae. Also, it may be desirable to provide channels permitting lubrication of the convex and concave surfaces. Channels permitting lubrication of surfaces are described in U.S. application Ser. No. 10/903,913, filed Jul. 30, 2004, entitled "Intervertebral Prosthetic Disc with Metallic Core", published under U.S. Publ. No. 2006/0025862, the full disclosure of which has been previously incorporated herein by reference.

Figure 2A:
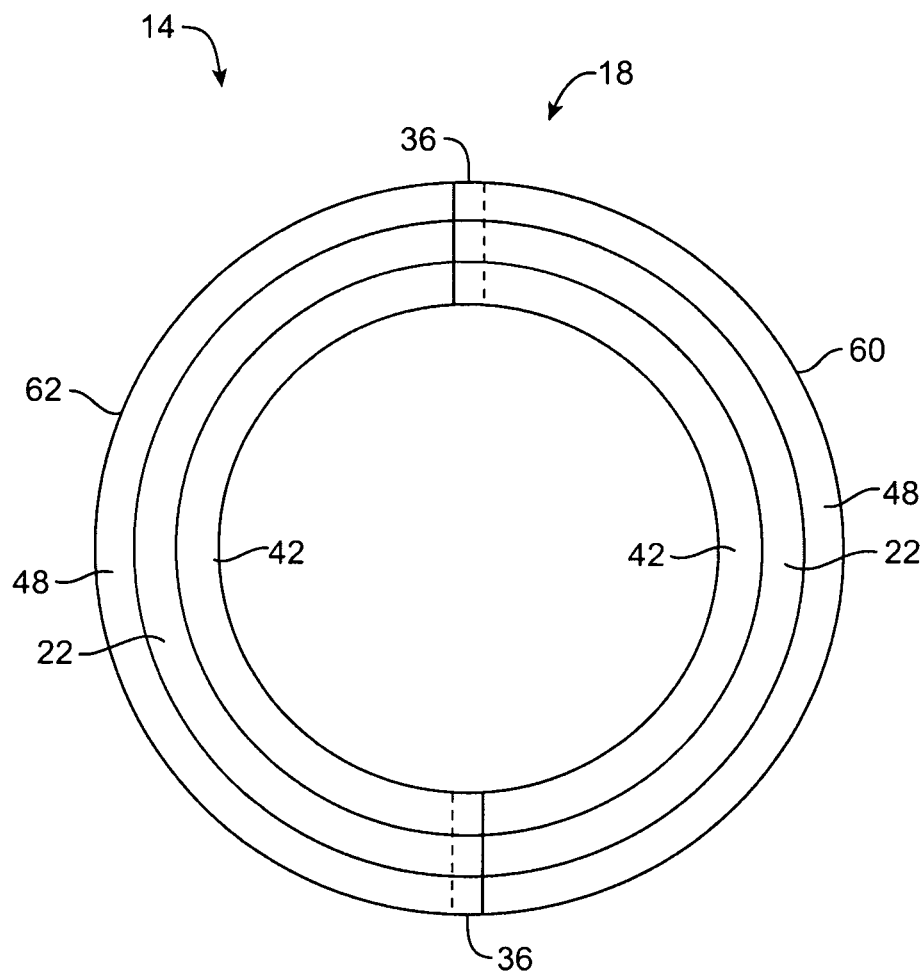
FIG. 2A shows an upper ring formed from arcuate sections.

Turning now to FIG. 2A, upper ring 14 can be formed with separable components 18 such as arcuate sections 60 and 62. Locking mechanism 36 can be used at two locations to permit the arcuate sections to be joined together in situ to form the upper ring.

Figure 2B:
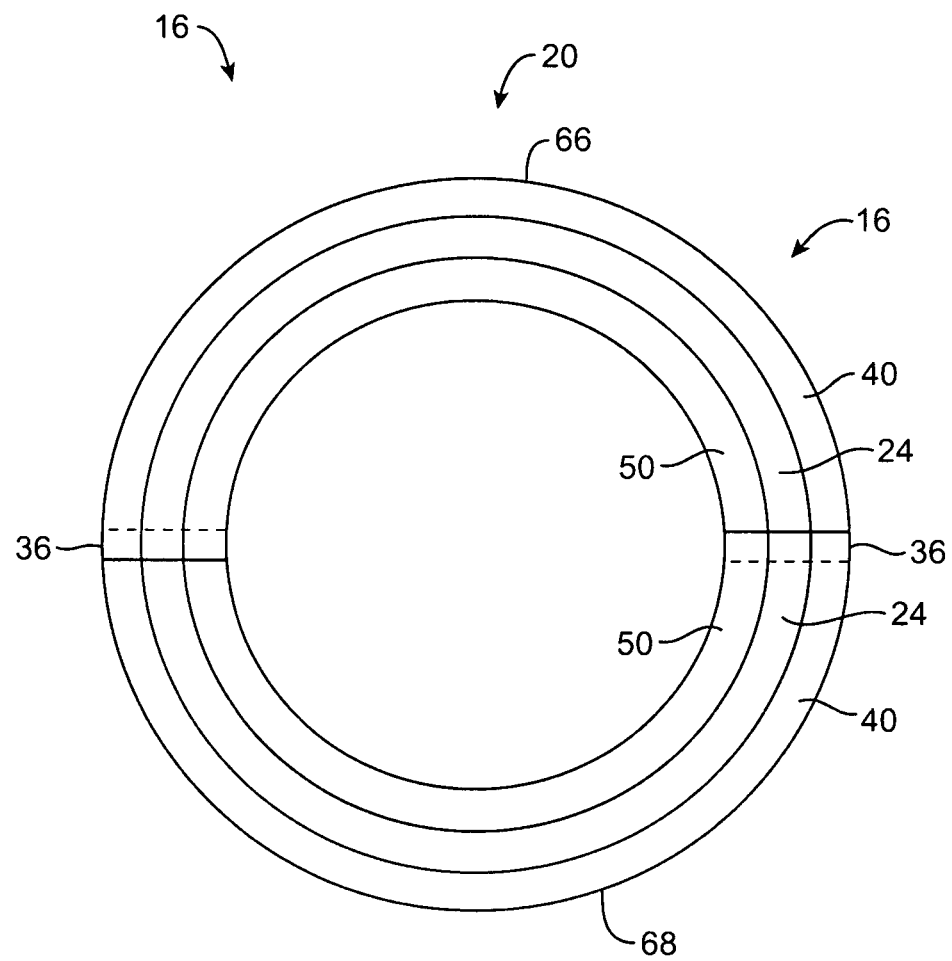
FIG. 2B shows a lower ring formed from arcuate sections.

Turning now to FIG. 2B, lower ring 16 can be formed with separable components 20 such as arcuate sections 66 and 68. Locking mechanism 36 can be used at two locations to permit the arcuate sections to be joined together in situ to form the lower ring.

Figure 2C:
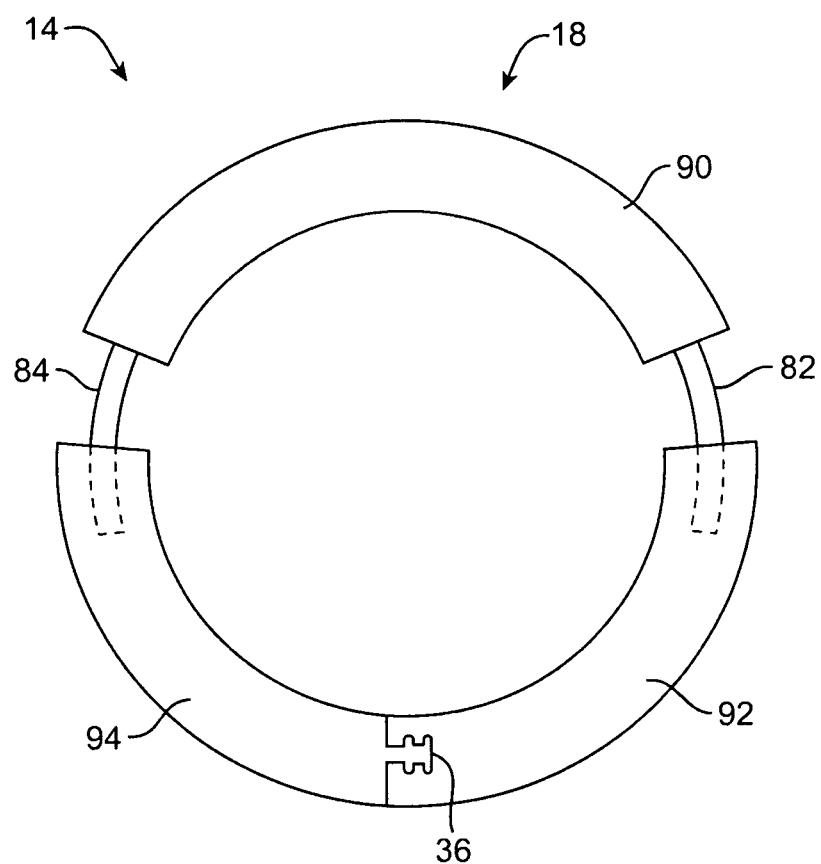
FIG. 2C shows a top down view of an upper ring formed with three arcuate sections and a low profile connector.

Turning now to an embodiment illustrated in FIG. 2C, an upper ring 16 can be formed with three arcuate sections 90, 92 and 94. Locking mechanism 36 rigidly joins components 92 and 94. A first low profile connector 82 joins arcuate section 90 and arcuate section 92. Low profile connector 82 can be formed in arcuate section 90. Arcuate section 92 can have an opening formed thereon to receive low profile connector 82, so as to permit insertion of low profile connector 82 into arcuate connector 92. In alternate embodiments, arcuate section 90 can have an opening formed thereon to receive low profile connector 82. A second low profile connector 84 joins arcuate section 90 and arcuate section 94. Second low profile connector 84 can be formed in arcuate section 90. Arcuate section 94 can have an opening formed thereon to receive second low profile connector 84, so as to permit insertion of low profile connector 84 into second arcuate connector 94. Insertion of first low profile connector 82 into first arcuate section 92 and insertion of second low profile connector 84 into second arcuate section 94 forms upper ring 18 as a rigid structure. Lower ring 16 can be formed from three arcuate sections 20 in a manner similar to that shown above with respect to upper ring 14.

Figure 2D:
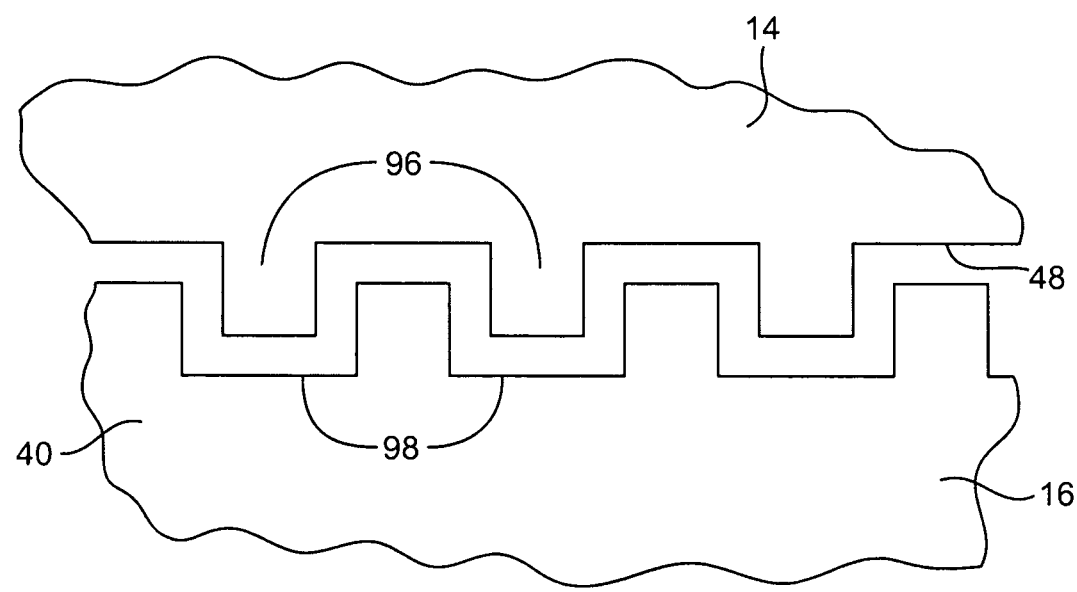
FIG. 2D shows a torsion stops formed in an upper ring.

Turning now to FIG. 2D which shows torsion stops which can be provided to prevent torsional rotation of upper ring 14 relative to lower ring 16. Stops 96 can be formed in the surface of upper ring 14. Lower ring 16 can have openings 98 shaped to receive stops 96. Torsional motion is limited by stops 96 engaging the surface of lower ring 16. In alternate embodiments, stops can be formed in the surface of lower ring 16 and openings can be formed upper ring 14 to receive the stops.

Figure 3:
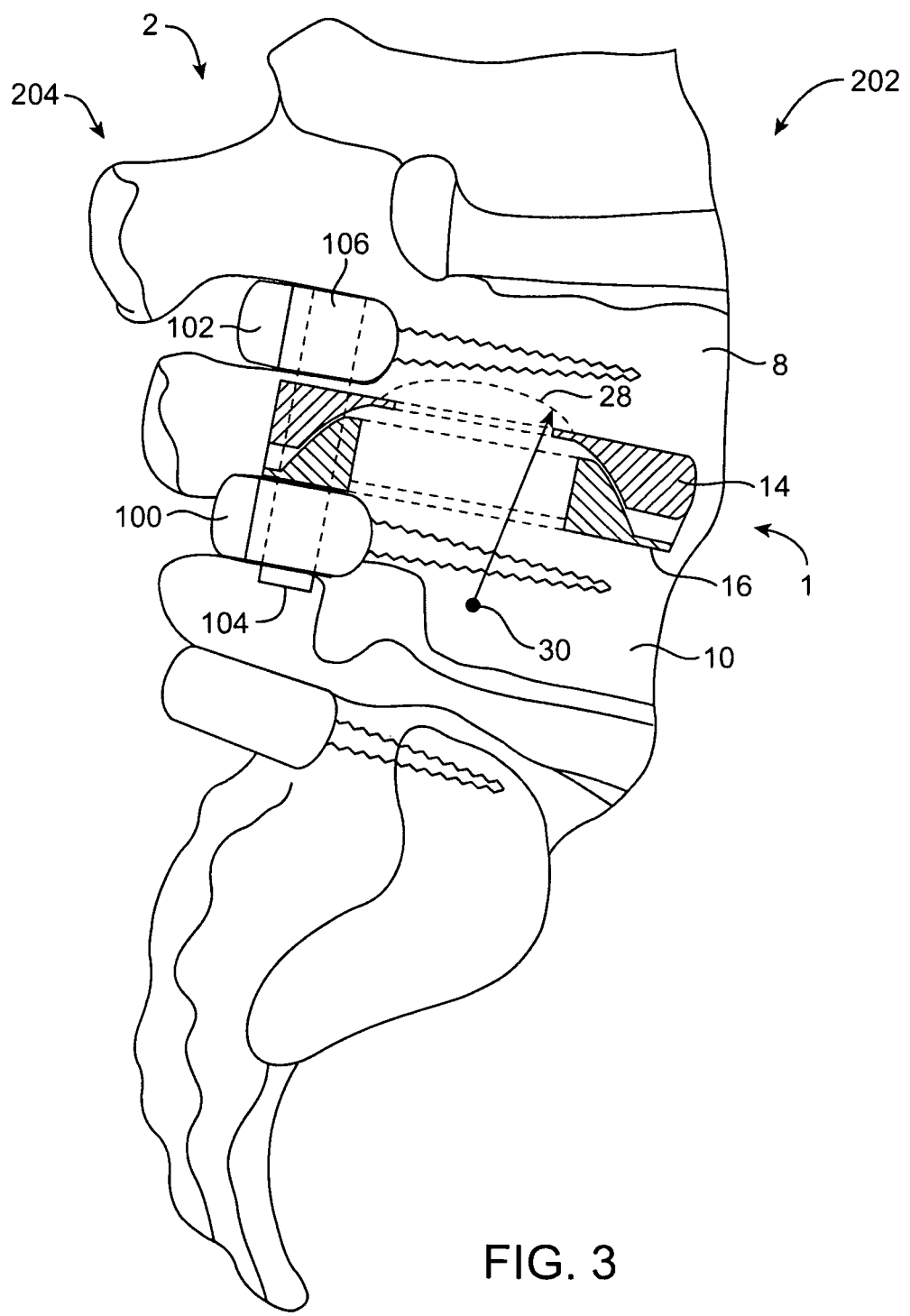
FIG. 3 shows a cross-sectional side view of a joint assembly supported with screws.

Turning now to FIG. 3, a cross-sectional side view of a joint assembly supported with screws is shown. An inferior pedicle screw 100 is inserted into an inferior pedicle of inferior vertebra 10. Pedicle screw 100 can comprise a conventional pedicle screw. Inferior pedicle screw 100 supports lower ring 16 and anchors lower ring 16 to inferior vertebra 10. A superior pedicle screw 102 is inserted into a superior pedicle of superior vertebra 8. Superior pedicle screw 102 supports upper ring 14 and anchors upper ring 14 to superior vertebra 8. An inferior post 104 can be inserted from lower ring 16 into inferior pedicle screw 100 to affix lower ring 16 to inferior pedicle screw 100. A superior post 106 can project upwards from upper ring 14 into superior pedicle screw 102 to affix upper ring 14 to superior pedicle screw 102. In alternate embodiments, the pedicle screws or custom designed screws can pass through support structures attached to the upper and lower rings. These support structures may resemble rods as used in pedicular screw fixation systems or may be integral posts forming part of the posterior part of the endplates. A dorsal, back or posterior location on spine 2 is generally designated as back 204 of spine 2 of the patient. A ventral, front or anterior location on spine 2 is generally designated as front 202 of spine 2 of the patient.

Figure 4:
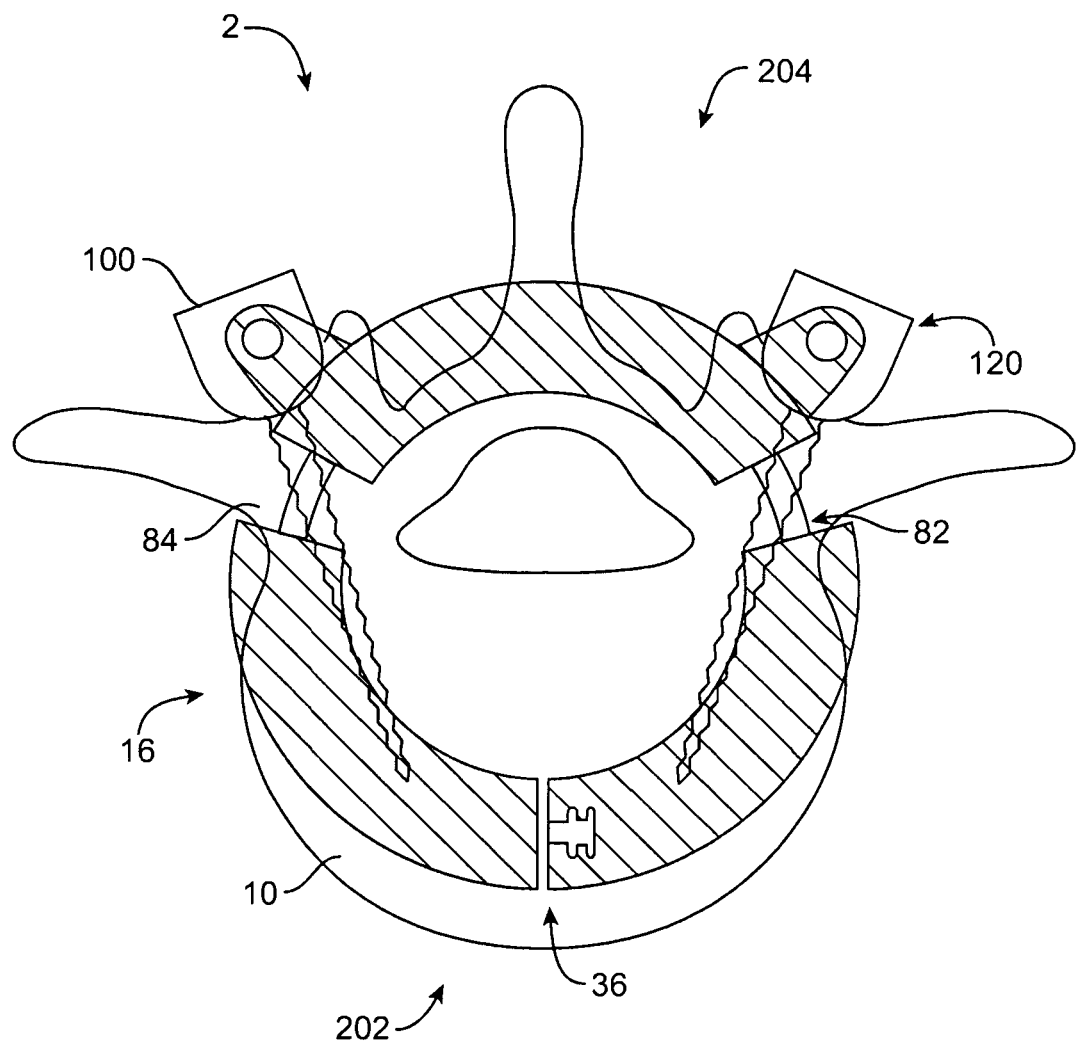
FIG. 4 shows a top down view of the joint assembly of FIG. 3.

Turning now to FIG. 4, a top down view of the joint assembly of FIG. 3 is shown. A second inferior pedicle screw 120 is inserted into inferior vertebra 10 of spine 2 of the patient to anchor the lower ring. Both first inferior pedicle screw 100 and second inferior pedicle screw 120 can be inserted from the back of the patient.

Components of lower ring 16 as described above can be provided at the surgical site by access from the posterior side of the patient. Access can be provided to permit in situ assembly of intervertebral joint 1, for example posterior access and assembly with an arthroscope. Lower ring 16 can be formed in situ as described above, and anchored to the inferior vertebra 10 with the pedicle screws. Components of upper ring 14 as described above can be provided and assembled at the surgical site with access from the posterior side of the patient. A second superior pedicle support screw similar to first superior pedicle support screw 102 can be inserted into superior vertebra 8. Upper ring 14 can be assembled in situ and anchored to superior vertebra 8 as described above to form assembled intervertebral joint 1.

Figure 5:
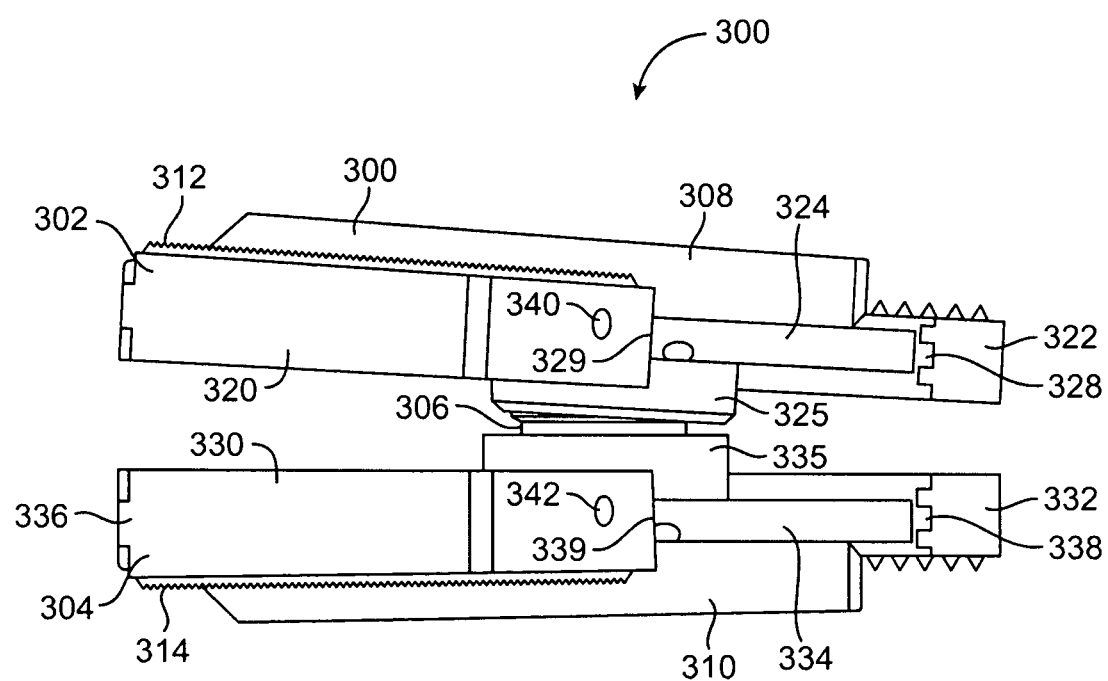
FIG. 5 shows a self expanding intervertebral joint assembly in accordance with an embodiment.

FIG. 5 shows a self expanding intervertebral joint assembly 300. The assembly includes an upper support 302 and a lower support 304. An intermediate member, or biconvex core 306 is positioned between the upper and lower supports to permit the upper and lower supports to articulate. An elongate anchor 308, is located on the upper support and anchors the assembly into the upper vertebra. Another elongate anchor 310 is located on the lower support and anchors the lower support into the lower vertebral. The elongate anchors are adapted to enter a groove formed in the vertebrae. Pyramidal anchors 312 are located on the upper support to anchor the upper support into the upper vertebra. Pyramidal anchors 314 are located on the lower support and anchor the lower support on the lower vertebra.

Upper support 302 includes a distal component 320, a proximal component 322 and a middle component 324 which can be arranged in situ to form the upper support. Distal component 320 is connected to proximal component 322 with an articulate joint 326. Proximal component 322 is connected to middle component 324 with a joint 328. These components are arranged in situ to form the lower support by articulating the upper support components about the joints. An aperture 340 is located in the distal component 320. A cable can be passed through the aperture. The cable is used to arrange the components by pulling on the cable to pivot the components into place as described more fully herein below.

Lower support 304 includes a distal component 330, a proximal component 332 and a middle component 334 which can be arranged in situ to form the lower support. Distal component 330 is connected to proximal component 332 with an articulate joint 336. Proximal component 332 is connected to middle component 334 with a joint 338. These components are arranged in situ to form the lower support by articulating the upper support components about the joints. An aperture 342 is located in the distal component 320. A cable can be passed through the aperture. The cable is used to arrange the components by pulling on the cable to pivot the components into place as described more fully herein below.

The upper and lower supports include features which permit the supports to articulate and restore motion between the vertebrae. Upper support 302 has a protruding structure 325 which has a concave surface feature formed therein, as shown below, which mates the upper surface of biconvex core 306. Lower support 304 has a protruding structure 335 which has a concave surface feature formed therein, as shown below, which mates the lower surface of biconvex core 306. In an alternate embodiment, the features of the upper and lower support are in direct contact and mate to provide articulation. For example, the upper support can have a protrusion with a convex surface, and the lower support can have a protrusion with a concave surface, in which the two surfaces mate to form a load bearing articulate joint.

FIGS. 6A-6D show a method for introducing the joint assembly of FIG. 5 into an intervertebral space. As shown in these figures, the upper and lower supports are arranged and introduced together, although the upper and lower supports can be arranged sequentially. In a preferred embodiment, an insertion instrument removably attaches to the proximal components and holds the components together as shown in FIGS. 6A-6D. While many instruments can be adapted to removably attach the proximal components, one such instrument is described in U.S. application Ser. No. 11/187,733, filed Jul. 21, 2005, entitled "Intervertebral Prosthesis Placement Instrument", the full disclosure of which has been previously incorporated herein by reference Referring to FIG. 6A, distal component 320 and proximal component 322 of the upper support 302 are arranged in an elongate configuration for introduction to the surgical site. Middle component 324 is folded within a recess so that the upper support components have a slender profile for introduction into the surgical site. Distal component 330 and proximal component 332 of lower support 304 are similarly arranged in an elongate configuration with middle component 324 is folded within a recess so that the lower support components have a slender profile.

Figure 6A:
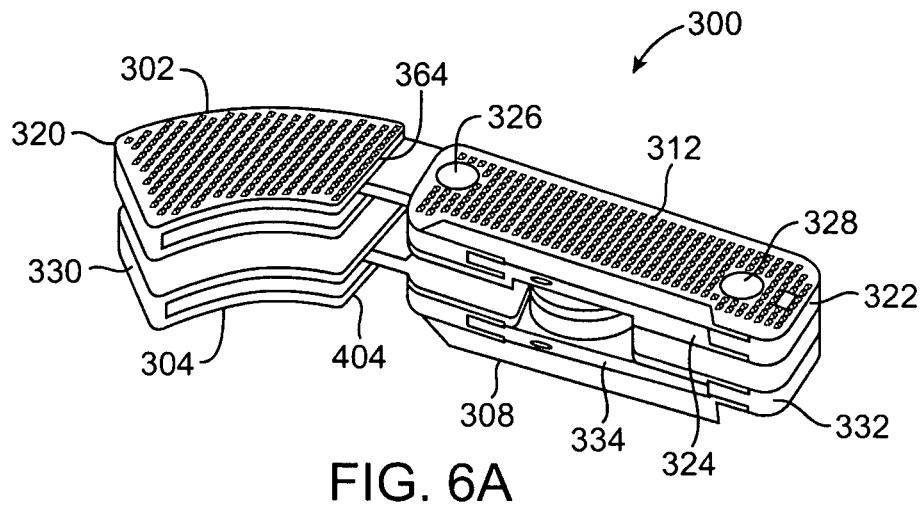
FIGS. 6A-6D show a method for introducing the joint assembly of FIG. 5 into an intervertebral space.
Figure 6B:
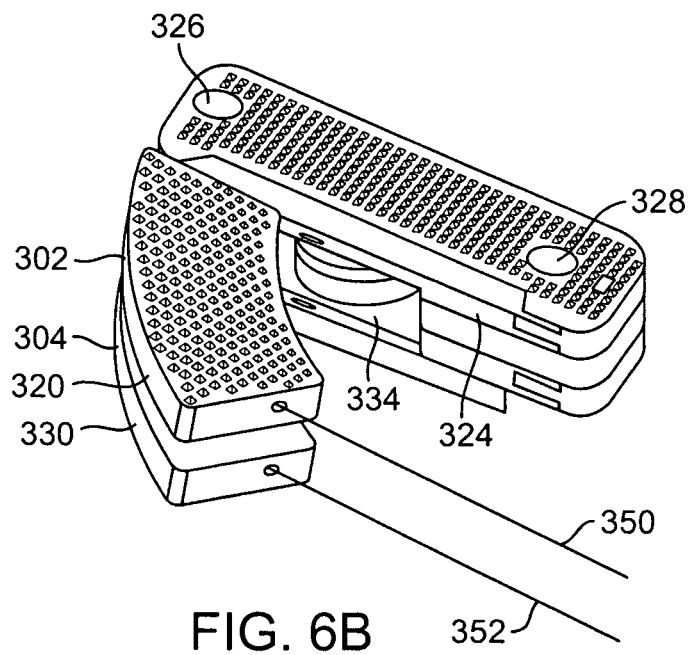

Referring now to FIG. 6B, the components are shown in an intermediate configuration. The distal components 320, 330 are pivoted proximally with respect to the proximal components. Distal component 320 has pivoted about joint 326. Cable 350 is used to pull upper support distal component 320 and pivot distal component 320 about joint 326. A stop 364 limits pivoting motion of distal component 320 in relation to proximal component 322. Cable 352 is used to pull lower support distal component 330 proximally and pivot distal component 330 about joint 336. A stop 404 (shown in FIG. 6A) limits pivoting motion of distal component 330. A groove (shown below) can be provided in each of the upper and lower distal components so that the middle components will not deploy until the distal components have reached the stops.

Figure 6C:
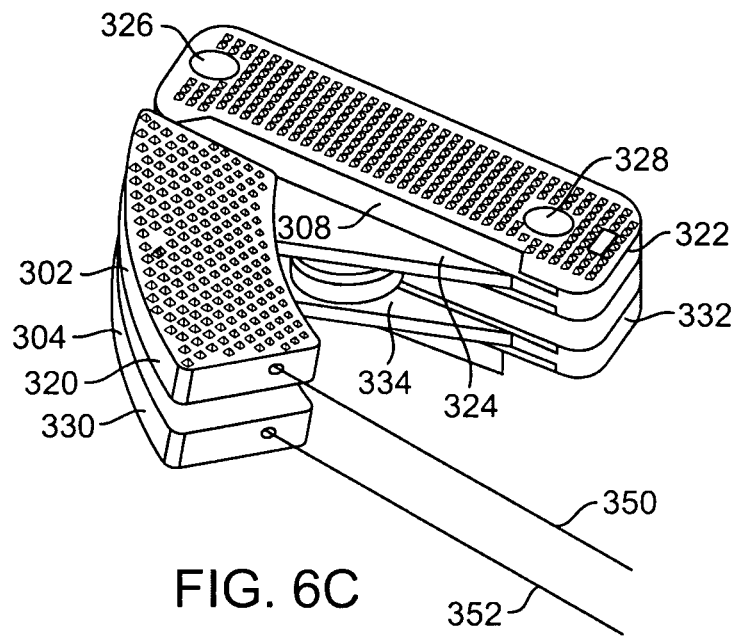
Figure 6D:
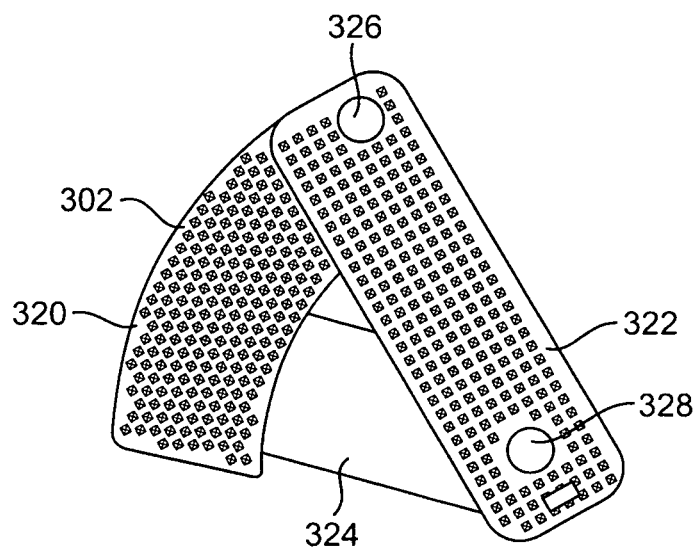

Referring now to FIG. 6C, the middle components 324, 334 of the upper and lower supports, respectively, pivot outward after the distal components are arranged. Upper cable 350 is attached near the distal end of middle component 324 so that cable 350 pulls on middle component 324 to pivot about joint 328. Similarly, lower cable 352 is attached near the distal end of middle component 334 so that cable 352 pulls on middle component 334 to pivot about joint 328. The cables are pulled until the middle components reach a final position as shown in FIG. 6D. The cable can also be guided through upper proximal component 322 and lower proximal component 332 and from there into a tensioner which can be part of the placement instrument which will facilitate pulling thereof.

Referring now to FIG. 6D, this top view shows middle component 324 in a final position so that the upper support is fully formed. Stops can be provided on each of the distal and middle components to limit pivoting motion of the middle components about the proximal components. The upper and lower support are fully formed once the middle components pivot to reach the stops. Stops can be formed with a protrusion which slides in a groove as described more fully herein below. Once the upper and lower supports are fully formed, the joint assembly is inserted into the intervertebral space. In a preferred embodiment, the joint assembly is inserted partially into the intervertebral space in a rigid wedge configuration and then allowed to freely articulate, so as to limit stretching and promote ligamentotaxis, as described in co-dending U.S. application Ser. No. 10/913,780, filed Aug. 6, 2004 entitled "Methods and Apparatus for Invertebral Disc Prosthesis Insertion", the full disclosure of which has been previously incorporated herein by reference.

Figure 7A:
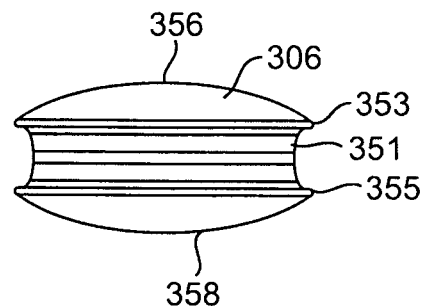
FIGS. 7A and 7B show the biconvex core of the joint assembly of FIGS. 5 and 6A-6D.
Figure 7B:
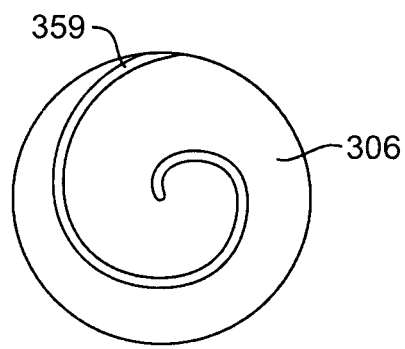

FIGS. 7A and 7B show biconvex core 306 of the joint assembly 300 of FIGS. 5 and 6A-6D. FIG. 7A shows a side view of the core, and FIG. 7B shows a top view of the core. Core 306 includes a groove 351 and an upper flange 353 and a lower flange 354. Groove 351 engages a flange on the lower support, shown herein below, to retain core 306 within joint assembly 300, as described in U.S. application Ser. No. 10/855,253, filed May 26, 2004, entitled "Prosthetic Disc for Intervertebral Insertion", U.S. Pub. No. 2005/0021145, the full disclosure of which is incorporated herein by reference. Core 306 includes an upper convex surface 356 and a lower convex surface 358. These surfaces mate with surfaces in the protrusions described above. Core 306 can be made from any biocompatible material including known biocompatible polymers and metals. In a preferred embodiment, core 306 is made from metal, for example cobalt chrome, and includes at least one channel 359 to permit fluid to lubricate the load bearing surfaces of the core, as described in U.S. application Ser. No. 10/903,913, filed Jul. 30, 2004, entitled "Intervertebral Prosthetic Disc with Metallic Core", published as U.S. Pub. No. 2006/0025862, the full disclosure of which is incorporated herein by reference. Although core 306 is shown as biconvex, the core can be any shape and have any combination of surfaces including plano/convex, plano/concave and biconcave surfaces. Core 306 includes a channel 351 formed around the periphery of the core. Channel 351 is formed in core 306 to define an upper rim flange 353 and a lower rim flange 355. Channel 351 receives a flange on the lower support to limit motion of the core in relation to the lower support, for example to prevent the core from sliding off the concave surface of the lower support. In an alternate embodiment, both the upper support and the lower support have a flange which is received by channel 351 to prevent the supports from sliding off the core.

FIG. 8A through FIG. 8E show distal component 320 of upper support 302. FIG. 8B shows a front view of distal component 320 while FIG. 8A, FIG. 8C and FIG. 8D show top, side and cross-sectional views, respectively, of distal component 320. Distal component 320 has a proximal end 362, and also includes an aperture 360 formed near proximal end 362. Aperture 360 mates with proximal component 322 to form pivot joint 326. Several pyramidal anchors 312 are formed on the surface of distal component 320 and anchor the support to the upper vertebra. Distal component 320 includes a distal region 365, which is shown in detail in FIG. 8E. Each pyramidal anchor has a square base about 0.9 mm on each side and a height of about 0.8 mm. As shown in FIG. 8A aperture 340 is formed in distal component 320 to pass cable 350 as described above. A recess 366 is formed in distal component 320 to permit the middle component to pivot toward distal end portion 365. Within recess 366 a groove 368 is formed in component 320 which receives a protrusion formed in the middle component, described herein below.

Figure 9C:
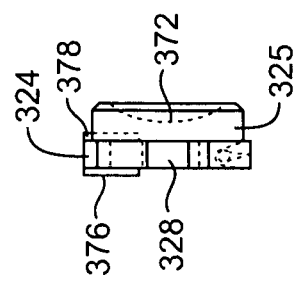
FIGS. 9A-9C show the middle support component of the upper support of FIGS. 5 and 6A-6D.
Figure 9A:
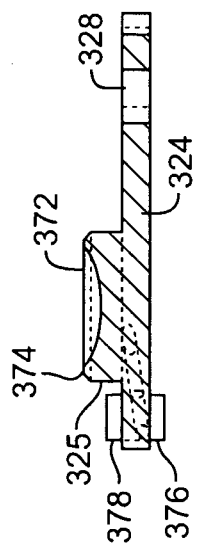
Figure 9B:
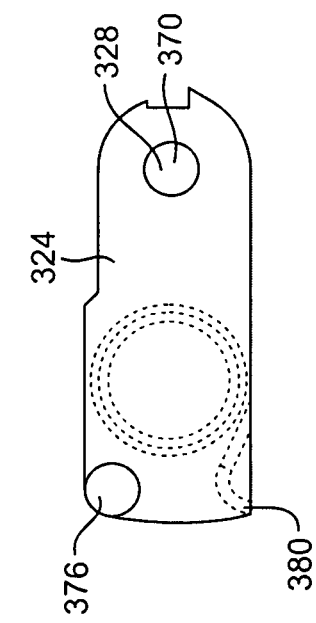

FIG. 9A through FIG. 9C show middle support component 324 of upper support 302. FIG. 9B shows a front view of middle component 324 while FIG. 9A shows a top view and FIG. 9C shows a side view. Middle component 324 has an aperture 370 formed near the proximal end. Aperture 370 mates with proximal component 322 to form pivot joint 328. An aperture 380 formed in the distal end of middle component 324 has cable 350 positioned therein as described above. Proximal advancing of cable 352 pivots middle component 324 about joint 328. An upper protrusion 376 is located near the distal end of middle component 324. A lower protrusion 378 is also located near the distal end of middle component 324. Protrusion 378 slides in grove 368 of distal component 320 as described above. Middle component 324 includes protruding structure 325. Protruding structure 325 includes a concave surface feature 372 which engages the biconvex core. Protruding structure 325 also includes a bevel 374 which mates with flange formed on protruding structure 335 as described herein below.

FIG. 10A through FIG. 10D show proximal support component 322 of upper support 302. FIG. 10B shows a front view of component 322 while FIGS. 10A, 10C and 10D show top, side and cross-sectional views of component 322, respectively. An aperture 392 is formed near the proximal end of proximal component 322. Aperture 392 mates with middle component 324 to form pivot joint 328 as described above. Proximal component 322 includes elongate anchor 308, and pyramidal anchors 312 as described above. An aperture 390 is formed near the distal end of proximal component 322. Aperture 390 mates with distal component 320 to form pivot joint 326 as described above. Proximal component 322 includes a recess 394 which at least partially encloses middle component 324 while the components are in an elongate configuration as described above. Within recess 394 component 322 has a groove 398 formed therein. Groove 398 receives the protrusion of the middle component as described above to permit the middle component to pivot from within recess 394 as described above. A cutout 396 is formed in proximal component 322. Cutout 396 receives protruding structure 325 while middle component 324 is positioned within recess 394.

Figure 11D:
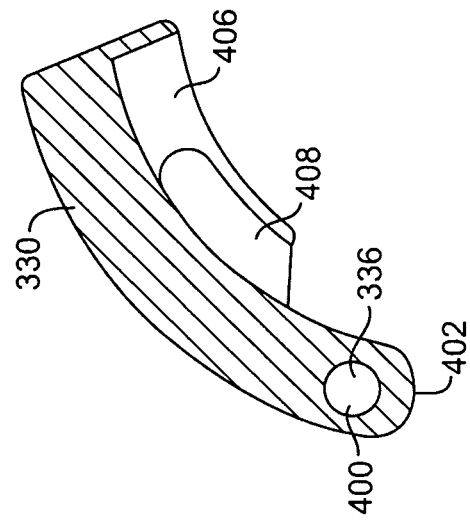
FIGS. 11A-11D show the distal support component of the lower support of FIGS. 5 and 6A-6D.
Figure 11C:
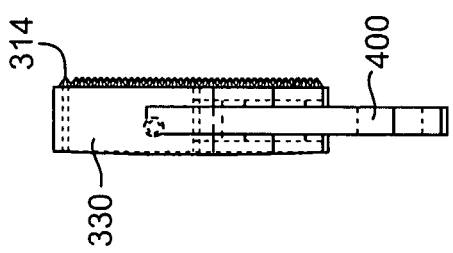
Figure 11A:
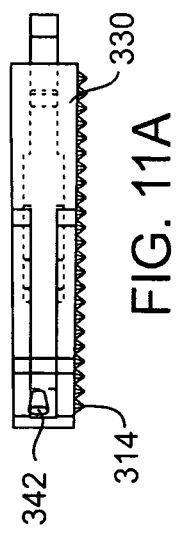
Figure 11B:
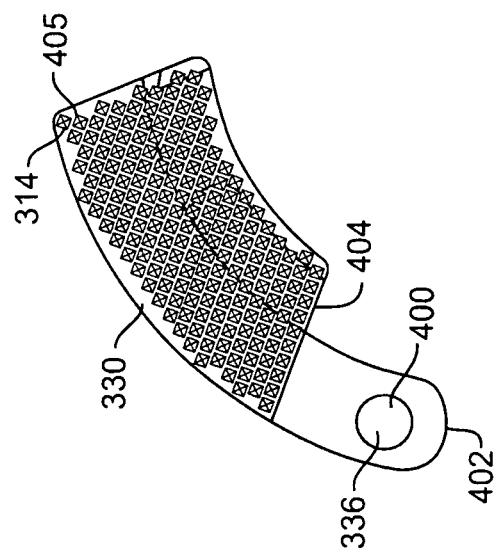

FIG. 11A through FIG. 11D show distal component 330 of lower support 304. FIG. 11B shows a front view of distal component 330 while FIG. 11A, FIG. 11C and FIG. 11D show top, side and cross-sectional views, respectively of distal component 330. Distal component 330 has a proximal end 336, and also includes an aperture 400 formed near proximal end 336. Aperture 336 mates with proximal component 332 to form pivot joint 336. Several pyramidal anchors 314 are formed on the surface of distal component 330 and anchor the support to the lower vertebra. Distal component 330 includes a distal end 402. Each pyramidal anchor has a square base about 0.9 mm on each side and a height of about 0.8 mm. As shown in FIG. 11A aperture 342 is formed in distal component 330 to pass cable 352 as described above. A recess 406 is formed in distal component 330 to permit the middle component to pivot toward distal end 405. Within recess 406 a groove 408 is formed in component 330 which receives a protrusion formed in the middle component, described herein below.

Figure 12D:
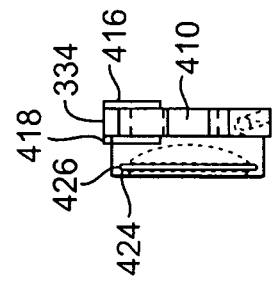
FIGS. 12A-12D show the middle support component of the lower support of FIGS. 5 and 6A-6D.
Figure 12C:
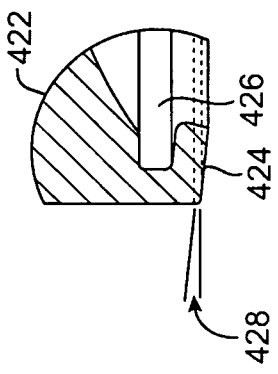
Figure 12A:
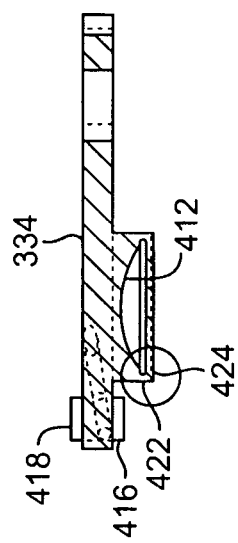
Figure 12B:
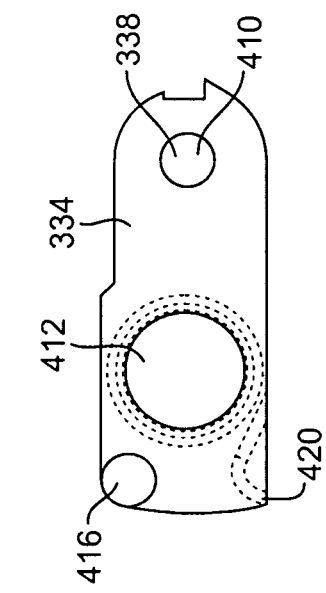

FIG. 12A through FIG. 12D show middle support component 334 of lower support 304. FIG. 12B shows a front view of middle component 334 while FIG. 12A shows a top view and FIG. 12C shows a side view. Middle component 334 has an aperture 410 formed near the proximal end. Aperture 410 mates with proximal component 332 to form pivot joint 338. An aperture 420 formed in the distal end of middle component 334 has cable 352 positioned therein as described above. Proximal advancing of cable 352 pivots middle component 334 about joint 338. An upper protrusion 416 is located near the distal end of middle component 334. A lower protrusion 418 is also located near the distal end of middle component 334. Protrusion 418 slides in grove 408 of distal component 330 as described above. Middle component 334 includes protruding structure 335. Protruding structure 335 includes a concave surface feature 412 which engages the biconvex core. Protruding structure 335 also includes a flange 424, or retaining ring, as shown in detail in FIG. 12D. Flange 424 mates bevel 374 as described above. Flange 424 is slopped at an angle 428 to mate with bevel 374 while the upper and lower supports of the joint assembly are deflected at a maximum angle of about six degrees. A groove 426 extends around protruding structure 335. Grove 426 mates with the flange on the biconvex core described above, thereby retaining the biconvex core between upper protruding structure 325 and lower protruding structure 335. In an alternate embodiment, the upper support also includes a groove and a flange which are similar to groove 426 and flange 424, and the upper support grove and flange mate with upper rim flange 353 and channel 351 as described above. Thus, in this alternate embodiment both the upper support and the lower support include groves and flanges which mate with the core to prevent the upper and lower supports from sliding off the core.

FIGS. 13A-13D show the proximal support component of the lower support of FIGS. 5 and 6A-6D. FIG. 13A through FIG. 13D show proximal support component 332 of lower support 304. FIG. 10B shows a front view of component 332 while FIGS. 13A, 13C and 13D show top, side and cross-sectional views of component 332, respectively. An aperture 432 is formed near the proximal end of proximal component 332. Aperture 432 mates with middle component 334 to form pivot joint 338 as described above. Proximal component 332 includes elongate anchor 310, and pyramidal anchors 314 as described above. An aperture 430 is formed near the distal end of proximal component 332. Aperture 430 mates with distal component 330 to form pivot joint 336 as described above. Proximal component 332 includes a recess 434 which at least partially encloses middle component 334 while the components are in an elongate configuration as described above. Within recess 434 component 332 has a groove 438 formed therein. Groove 438 receives the protrusion of the middle component as described above to permit the middle component to pivot from within recess 434 as described above. A cutout 436 is formed in proximal component 332. Cutout 436 receives protruding structure 335 while middle component 334 is positioned within recess 434.

Figure 14:
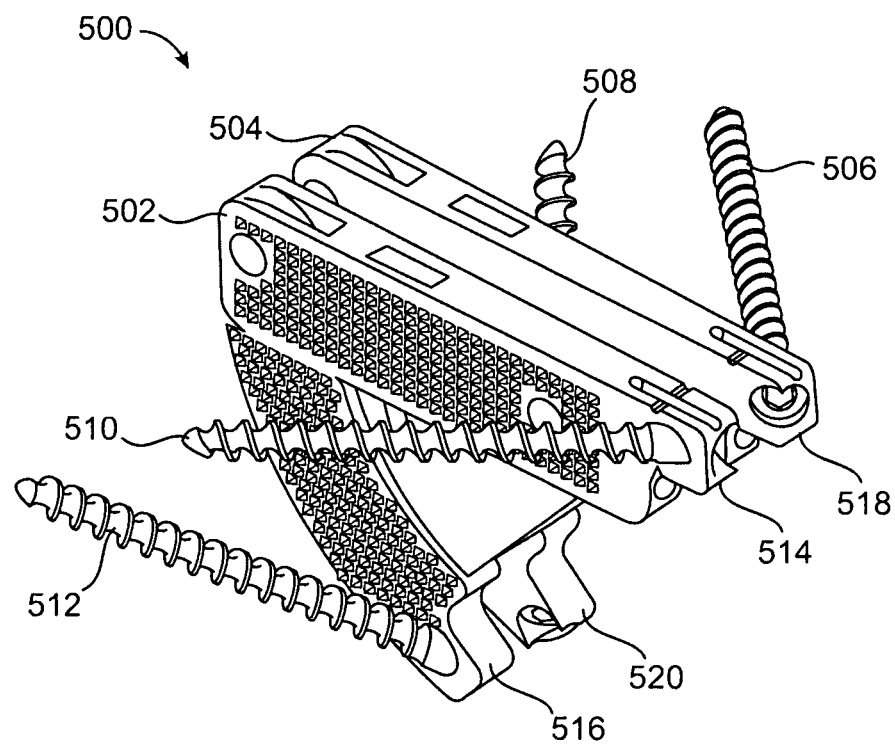
FIG. 14 shows an embodiment using anchoring screws driven from the posterior instead of elongate anchors.

FIG. 14 shows an embodiment of an articulate intervertebral joint assembly 500 using anchoring screws 506, 508, 510, and 512 instead of a pair of elongate anchors as described above. Joint assembly 500 is made with many of the components as described above and can be assembled in situ by unfolding and/or pivoting the components as described above. Joint assembly 500 includes an upper support 502 and a lower support 504. Upper support 502 includes a protruding structure 514 on the proximal component and a protruding structure 516 on the distal component. Protruding structure 514 has a hole formed therein to receive anchoring screw 510, and protruding structure 516 has a hole formed therein to receive anchoring screw 512. Lower support 504 includes a protruding structure 518 on the proximal component and a protruding structure 520 on the distal component. Lower support protruding structure 518 has a hole formed therein to receive anchoring screw 506, and protruding structure 520 has a hole formed therein to receive anchoring screw 508.

While joint assembly 500 is assembled in situ similarly to joint assembly 300 as described above, the use of screws instead of elongate fins can provide advantages. After upper support 502 and lower support 504 are assembled in situ, joint assembly 500 is fully inserted and positioned in the intervertebral space. In some embodiments, joint assembly 500 is assembled at least partially in the intervertebral space by pivoting the components while a portion of at least one component is positioned within the intervertebral space. The position of assembly 500 is adjusted to a desired final position after assembly 500 has been fully inserted into the intervertebral space. Such adjustment after insertion into the intervertebral space can be difficult with some embodiments using elongate anchors as described above. The anchoring screws are inserted to hold the joint assembly in place at the desired final position. The anchoring screws are driven from the posterior of the patient and attach to the vertebrae and/or pedicles as described above. As shown in FIG. 14 the anchoring screws are used instead of the elongate anchors shown above, although anchoring screws can be used in conjunction with elongate anchors in other embodiments.

Figure 15:
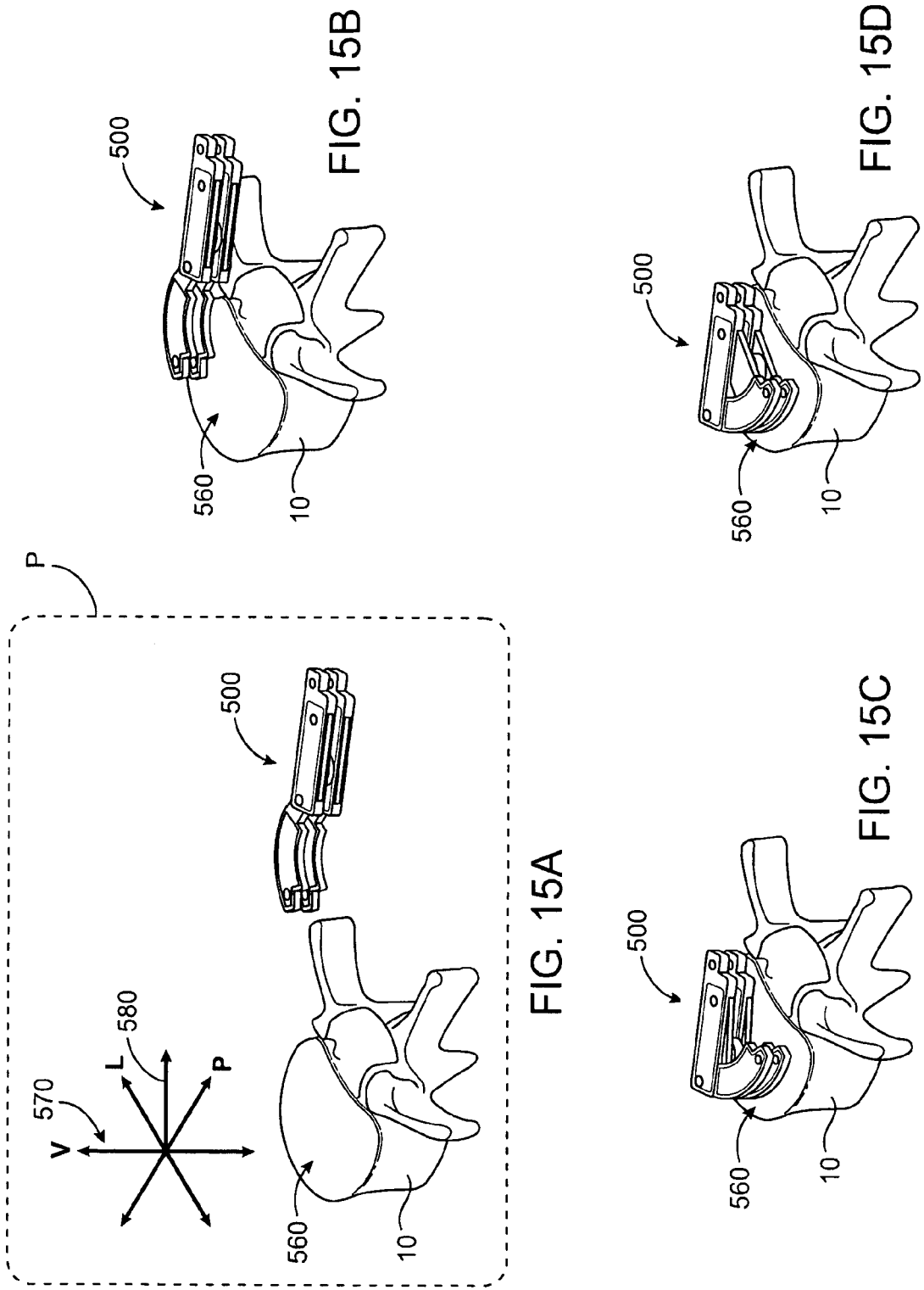
FIGS. 15A to 15D show a method of implanting a self expanding intervertebral joint assembly as in FIG. 14 according to an embodiment.

FIGS. 15A to 15D show a method of introducing a self expanding intervertebral joint assembly 500 as in FIG. 14 according to an embodiment. Joint assembly 300 can be similarly introduced. Joint assembly 500 is introduced into a patient P as shown in FIG. 15A. A patient reference system 570 includes a lateral patient direction L, a posterior patient direction P and a vertical patient direction V. Vertical patient direction V corresponds to vertical as the patient is standing and also corresponds to an inferior to superior orientation on the patient. An intervertebral space 560 is located adjacent the inferior vertebrae 10. For clarity only one vertebra several vertebrae as described above is shown. As shown in these figures, the upper and lower supports are arranged and introduced together, although the upper and lower supports can be arranged sequentially. An oblique direction 580 is located between the lateral and posterior directions. Although the joint assembly is introduced into the patient from a posterior direction, the implant can be rotated in the oblique direction near the spine to enter the spine along oblique direction 580. In some embodiments the joint assembly is introduced from the lateral direction, for example from the side of the patient. Although lateral introduction from the side of the patient can require a greater surgical distance traversed from the skin of the patient to the implant site, the tissue cut is typically muscle or other soft tissue such that the lateral implantation can be less invasive than implantation from the posterior direction.

Referring again to FIG. 15A, the distal component and the proximal component of the upper support are arranged in an elongate configuration for introduction to the surgical site as described above. The middle component is folded within a recess so that the upper support components have a slender profile for introduction into the surgical site. The distal component and the proximal component of the lower support are similarly arranged in an elongate configuration with the middle component folded within a recess so that the lower support components have a slender profile.

Referring now to FIG. 15B, the components are shown introduced into intervertebral space 560 in the elongate configuration. The distal component is advanced at least partially into the intervertebral space while the components remain in the elongate configuration.

Referring now to FIG. 15C, the components are shown in an intermediate configuration in the intervertebral space. The components have pivoted about the joints while the implant is positioned at least partially within the intervertebral space. The distal components are pivoted proximally with respect to the proximal components, and the distal components have pivoted about the joints. Cables as described above are used to pull the distal components and pivot the distal components about the joints. The stops as described above limit pivoting motion of the distal components in relation to the proximal components.

Referring now to FIG. 15D, the middle components of the upper and lower supports have been pivoted outward to the final position. The cables are attached near the distal end of middle components so that cables pull on the middle components to pivot the middle components about the joints, as described above. The middle components pivot while the proximal and distal components are positioned within the intervertebral space. The cables are pulled until the middle components reach the final position as shown in FIG. 15D. In some instances, it may be desirable to position the implant within the intervertebral space after the upper and lower supports are formed. The upper and lower supports are anchored to the vertebrae with screws as described above.

Figure 16:
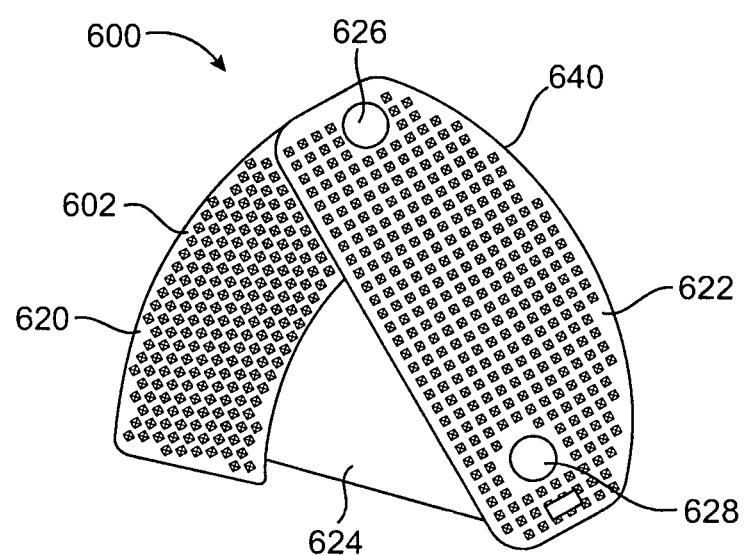
FIG. 16 shows a self expanding intervertebral joint assembly with a curved proximal component a curved middle component according to an embodiment.

FIG. 16. shows a self expanding intervertebral joint assembly 600 with a curved proximal component and a curved middle component according to an embodiment. Joint assembly 600 shows modifications to joint assembly 300 shown above, and joint assembly 500 can be similarly modified. An upper support 602 includes a distal component 620, a proximal component 622 and a middle component 624. The distal component is attached to the proximal component with an articulate joint 626. The proximal component is attached to the middle component with a joint 628. Proximal component 622 includes a curved edge 640. Curved edge 640 can correspond with any curve, for example an arc formed with from a radius of a circle. Curved edge 640 permits the proximal component to have a larger surface area oriented toward the vertebra. Additional anchors, for example pyramidal anchors, are provided on this larger surface area to attach to the vertebra. Middle component 624 also includes a curved edge which nests in proximal component 622. The curved edge of middle component 624 provides the middle component with a larger cross sectional width and a larger surface area than embodiments 300 and 500 shown above. The larger cross sectional width is sufficiently wide so that at least a portion of the middle component remains within the proximal component while the support is formed and no hole is present in the upper surface of the formed upper support. The lower support is formed similar to the upper support with curved edges on the proximal and middle components so as to provide a larger surface area on the lower support and a formed lower support without a hole in the middle. In alternate embodiments, the middle components include several small anchors, for example pyramidal anchors, on the surfaces oriented toward the vertebrae. In additional embodiments, the middle component is curved on the outer edge opposite edge 640 so that the upper support is curved on each outward facing edge of the proximal, distal and middle components. In these additional embodiments, the lower support is similarly formed.

Figure 17:
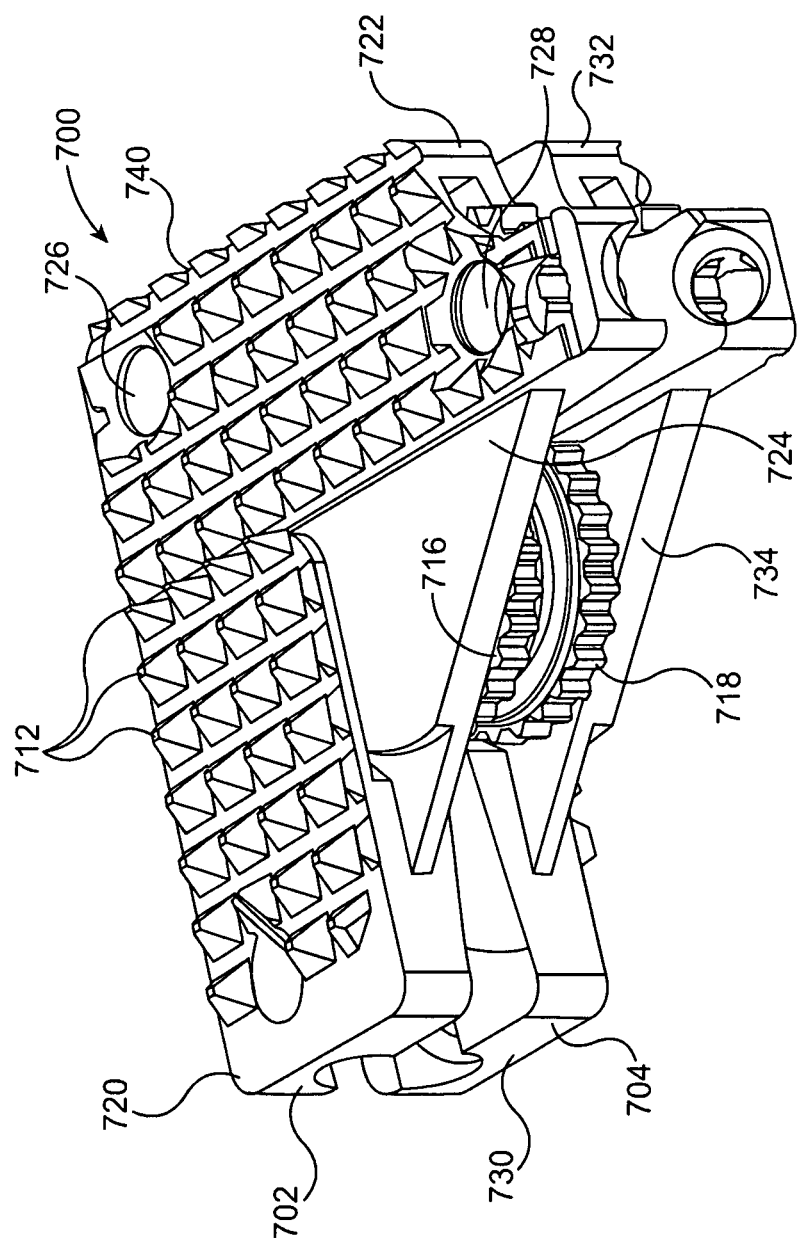
FIG. 17 shows a perspective view of a self expanding intervertebral joint assembly with gears in accordance with embodiments of the present invention.

FIG. 17 shows a perspective view of a self expanding intervertebral joint assembly 700 with gears in accordance with embodiments of the present invention. The assembly includes an upper support 702 and a lower support 704. An intermediate member, or biconvex core 706 is positioned between the upper and lower supports to permit the upper and lower supports to articulate. Pyramidal anchors 712 are located on the upper support to anchor the upper support into the upper vertebra. Pyramidal anchors 714 (shown in FIG. 19) are located on the lower support and anchor the lower support on the lower vertebra.

Upper support 702 includes a distal component 720, a proximal component 722 and a middle component 724 which can be arranged in situ to form the upper support. At least one gear is disposed on each of the components of the upper support. Distal component 720 is connected to proximal component 722 with an articulate joint 726. Proximal component 722 is connected to middle component 724 with a joint 728. These components are arranged in situ to form the lower support by articulating the upper support components about the joints. A retention ring gear 716 is located on the upper support and disposed around the protruding retention ring structure of the upper support that retains the biconvex core as described above. In many embodiments, gear 716 may comprise a freewheeling gear. Gear 716 can be used to arrange the components of the upper support by rotating so as to pivot the components into place as described more fully herein below.

Lower support 704 includes a distal component 730, a proximal component 732 and a middle component 734, which can be arranged in situ to form the lower support. At least one gear is disposed on each of the components of the lower support. Distal component 730 is connected to proximal component 732 with an articulate joint 736 (shown below in FIG. 19). Proximal component 732 is connected to middle component 734 with a joint 738 (shown below in FIG. 19). These components are arranged in situ to form the lower support by articulating the upper support components about the joints. A retention ring gear 718 is located on the lower support and disposed around the protruding retention ring structure of the lower support that retains the biconvex core as described above. In many embodiments, gear 716 may comprise a freewheeling gear. Gear 718 can be used to arrange the components of the lower support by rotating so as to pivot the components into place as described more fully herein below.

Figure 18:
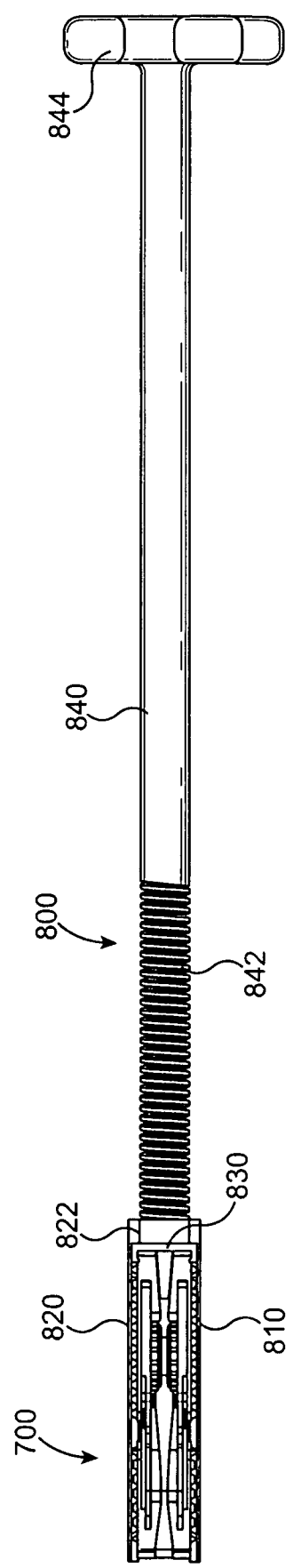
FIG. 18 shows a schematic illustration of a placement instrument with a cartridge loaded with a self-expanding intervertebral joint assembly as in FIG. 17 in accordance with embodiments of the present invention.

FIG. 18 shows a schematic illustration of a placement instrument 800 with a cartridge 810 loaded with a self-expanding intervertebral joint assembly 700 as in FIG. 17 in accordance with embodiments of the present invention. The cartridge can permit smooth deployment of the intervertebral joint assembly in a narrow, uneven space such as a narrow uneven intervertebral space. Cartridge 810 comprises an outer cartridge casing 820, an inner cartridge part 830, and a shaft 840. Shaft 840 is connected to cartridge 810. Shaft 840 has threads 842 formed thereon. Threads 842 mate with threads 822 formed in outer cartridge casing 820. A knob 844 is connected near one end of shaft 840 and rotation of knob 844 causes rotation of shaft 840 so as to advance shaft 840 in relation to outer cartridge casing 820.

Rotation of shaft 840 can advance inner cartridge part 840 so as to advance and deploy self-expanding intervertebral joint assembly 700. Shaft 840 is connected to inner cartridge part 830 such that rotation of shaft 840 can cause inner cartridge part 830 to advance distally along with shaft 840. Self expanding intervertebral joint assembly 700 is positioned near inner cartridge part 830. As inner cartridge part 830 advances distally intervertebral joint assembly 700 is pushed forward and advances distally. In some embodiments outer cartridge casing 820 can retract while the inner cartridge part advances distally or retract while the inner remains, The gears of the intervertebral joint assembly are mechanically coupled to the outer cartridge casing to rotated the gears as the assembly advances relative to the outer cartridge casing. Rotation of gears 716 and gear 718 can pivot the components of the upper and lower assembly so as to form the upper and lower supports, respectively.

Figure 19A:
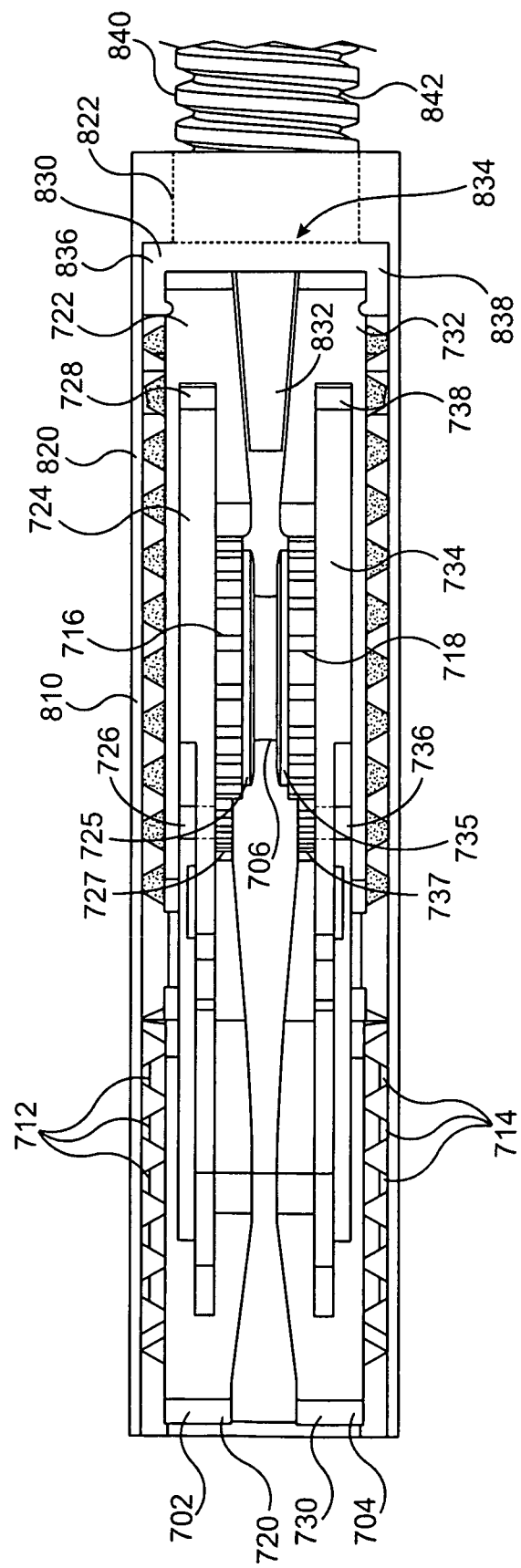
FIGS. 19A and 19B schematically illustrate details of the self-expanding intervertebral joint assembly loaded in the cartridge as in FIGS. 17 and 18, in accordance with embodiments of the present invention.
Figure 19B:
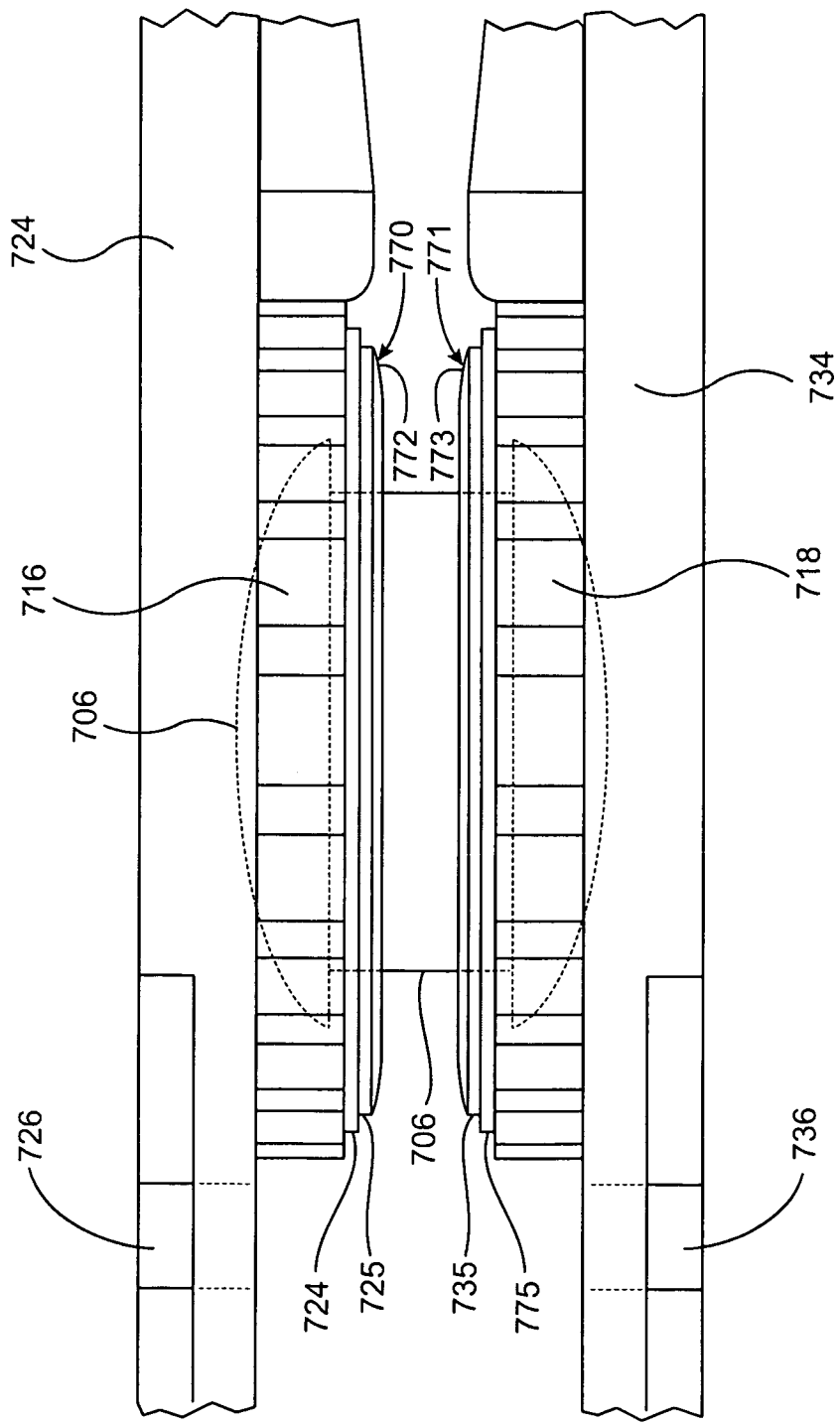

FIGS. 19A and 19B schematically illustrate details of the self-expanding intervertebral joint assembly loaded in the cartridge as in FIGS. 17 and 18, in accordance with embodiments of the present invention. Outer cartridge casing 820 extends over at least a portion of intervertebral joint assembly to permit advancement of the joint assembly into at least a portion of the intervertebral space while the joint assembly is substantially covered with outer cartridge casing 820. Outer cartridge casing 820 covers pyramidal anchors 712 and pyramidal anchors 714. Distal component 720 of upper support 702 and distal component 730 of lower support 704 are located near an opening in outer cartridge casing 820. Inner cartridge part 830 includes a wedge 832, upper flange 836 and lower flange 838. The upper and lower flanges include inner opposing surfaces, and the inner surface of each flange opposes one of the wedge surfaces to clamp the components of the upper and lower supports in a parallel configuration. Inner cartridge part 830 is connected to shaft 840.

Self expanding intervertebral joint assembly 700 includes structure to permit articulation between upper support 702 and lower support 704 to restore motion between the vertebrae. Upper support 702 has a protruding structure 725 which extends from middle component 724 and has a concave surface feature formed therein, as shown herein above, which mates the upper surface of biconvex core 706. Lower support 704 has a protruding structure 735 which extends from middle component 734 and has a concave surface feature formed therein, as shown herein above, which mates the lower surface of biconvex core 706. In an alternate embodiment, the features of the upper and lower support are in direct contact and mate to provide articulation. For example, the upper support can have a protrusion with a convex surface, and the lower support can have a protrusion with a concave surface, in which the two surfaces mate to form a load bearing articulate joint.

Protruding structure 725 and protruding structure 735 can also include structures to retain the biconvex core and upper and lower retention ring gears, respectively. Protruding structure 725 can include a retention ring, rim or annular flange as described above such as an annular flange 770 that projects radially inward toward biconvex core 706 to retain biconvex core 706. Annular flange 770 has a bevel 772 formed thereon to limit motion between the upper and lower supports. Retention ring gear 716 can have an annular shape formed to mate with protruding structure 725. Protruding structure 725 can include an outer circular surface that mates with an inner surface of inner annular surface of retention ring gear 716. Retention ring gear 716 can rotate around protruding structure 725. In addition to inwardly protruding annular flange 770 that retains biconvex core 706, protruding structure 725 can include a retention element 774 such as an outwardly protruding annular flange and/or C-ring clip to retain retention ring gear 716. Protruding structure 735 can include a radially inwardly projecting retention ring, rim or annular flange such as an annular flange 771 that extends toward biconvex core 706 to retain biconvex core 706. Retention ring gear 718 can also have an annular shape formed to mate with protruding structure 735. Protruding structure 735 can include an outer circular surface that mates with an inner annular surface of retention ring gear 718. Retention ring gear 718 can rotate around protruding structure 735. In addition to an inwardly protruding annular flange that retains biconvex core 706, protruding structure 735 can include an outwardly protruding retention element 775 such as an annular flange and/or C-ring clip to retain retention ring gear 718.

Implant 700 includes structures that pivot while the upper and lower supports are formed. A pivot gear 727 can engage upper retention ring gear 716. Pivot gear 727 is connected to joint 726 so that rotation of pivot gear 727 rotates pivot joint 726 to rotate distal component 720. A pivot joint 728 connects proximal component 722 to middle component 724 of upper support 702. Rotation about pivot joint 728 pivots middle component 724 toward the deployed position. A pivot gear 737 can engage lower retention ring gear 718. Pivot gear 737 is connected to pivot joint 736 so that rotation of pivot gear 737 rotates pivot joint 736 to rotate distal component 704 toward the deployed position. A pivot joint 738 connects proximal component 732 to middle component 734 of lower support 704. Rotation about pivot joint 738 pivots middle component 734 toward the deployed position.

Wedge 832, upper flange 836 and lower flange 838 restrain motion of the joint assembly during deployment by clamping the joint assembly while the joint assembly is advanced. Wedge 832 is positioned between upper support 702 and lower support 704. Wedge 832 and upper flange 836 engage proximal component 722 of upper support 702. Wedge 832 and lower flange 838 engage proximal component 732 of lower support 704. Advancement of inner cartridge part 830 advances wedge 832, upper, the upper and lower supports distally to engage gears of the support FIGS. 20A to 20E show a method for introducing the joint assembly with the cartridge as in FIGS. 17 to 19 into an intervertebral space, in accordance with embodiments of the present invention. The upper and lower supports are arranged and introduced together, although the upper and lower supports can be arranged sequentially. In a preferred embodiment, placement instrument 800 removably attaches to the components and holds the components of the upper and lower support together during assembly of the components as shown in FIGS. 20A-20D. The components of the upper and lower supports are arranged in a narrow profile configuration while positioned within the cartridge. The components of each support can be arranged to a second wide profile configuration to form the assembled upper and lower supports.

Figure 20A:
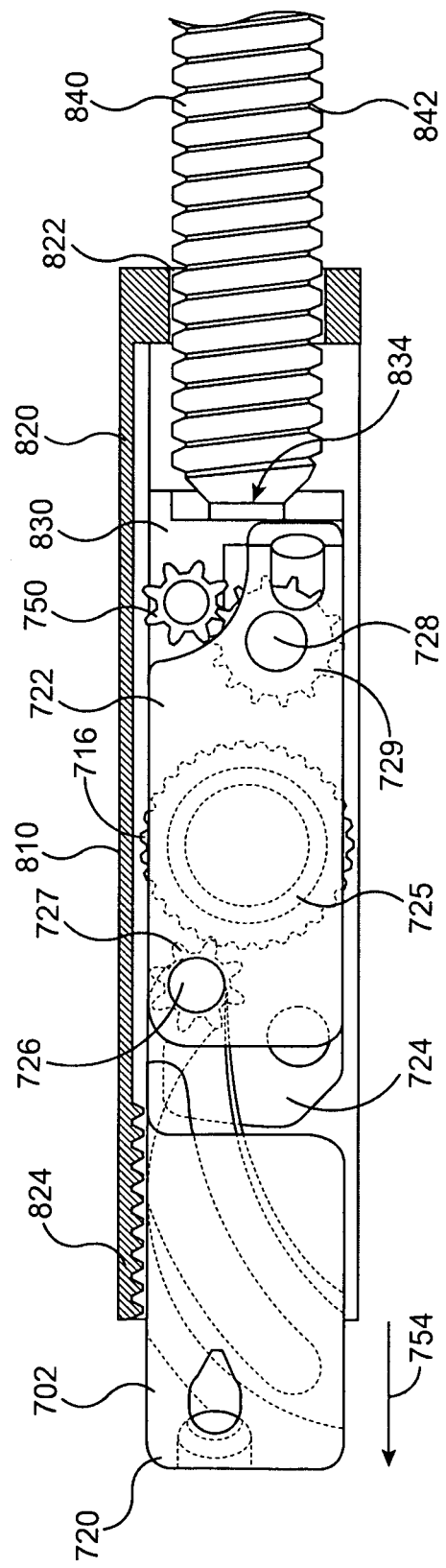
FIGS. 20A to 20E show a method for introducing the joint assembly with the cartridge as in FIGS. 17 to 19 into an intervertebral space, in accordance with embodiments of the present invention.

Referring now to FIG. 20A, distal component 720 and proximal component 722 of upper support 702 can be arranged in an elongate configuration for introduction to the surgical site. Middle component 724 is folded within a recess so that the upper support components have a slender profile for introduction into the surgical site. Distal component 730 and proximal component 732 of lower support 704 are similarly arranged in an elongate configuration, and middle component 724 is folded within a recess so that the lower support components have a slender profile. Outer cartridge casing 820 has an inner surface that includes a structure, for example a rack 824, formed thereon. Rack 824 includes teeth that can engage retention ring gear 716 and retention ring gear 718. In alternate embodiments, the cartridge can comprise a gear on or near the outer casing to engage at least one of the gears of the supports. A joint 834 connects shaft 840 to inner cartridge part 830 and permits shaft 840 to rotate while inner cartridge part 830 is advanced distally. An arrow 754 indicates distal advancement of inner cartridge part 830 and the components of the upper and lower supports in relation to rack 824 of outer cartridge casing 820. Rack 824 may not engage the retention ring gears until inner cartridge part 830 and the components of the upper and lower supports have advanced distally by a predetermined amount.

Figure 20B:
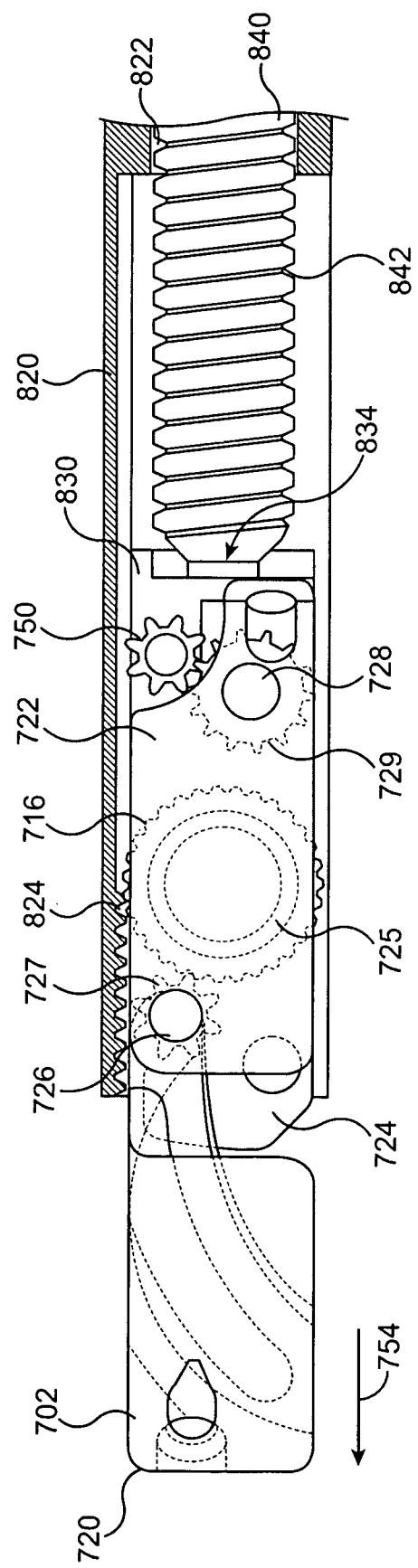

Referring now to FIG. 20B, inner cartridge part 830 has advanced the components of the upper and lower supports a sufficient distance so that rack 824 engages retention ring 824 of the upper support and the retention ring of the lower support. Retention ring gear 716 also engages pivot gear 727. Pivot gear 727 can be fixedly connected to distal component 720 of upper support 702 so that rotation of pivot gear 727 pivots distal component 720. Rack 824 can also engage retention ring gear 718 of lower support 704. Pivot gear 737 of lower support 704 can be fixedly connected to distal component 730 of lower support 704 so that rotation of pivot gear 737 pivots distal component 730. The retention ring gears can rotate about an axis of rotation that may be concentric with the protruding structures that retain the biconvex core. The pivot gears can rotate about an axis of rotation that is concentric with the pivot gears. In many embodiments, the axis of rotation of each retention ring gear is aligned with the axes of rotation of each pivot gear so that the axes are parallel. The axis of rotation of pivot gear 727 is concentric with an axis of rotation of joint 726, and the axis of rotation of pivot gear 737 is concentric with an axis of rotation of joint 736.

Figure 20C:
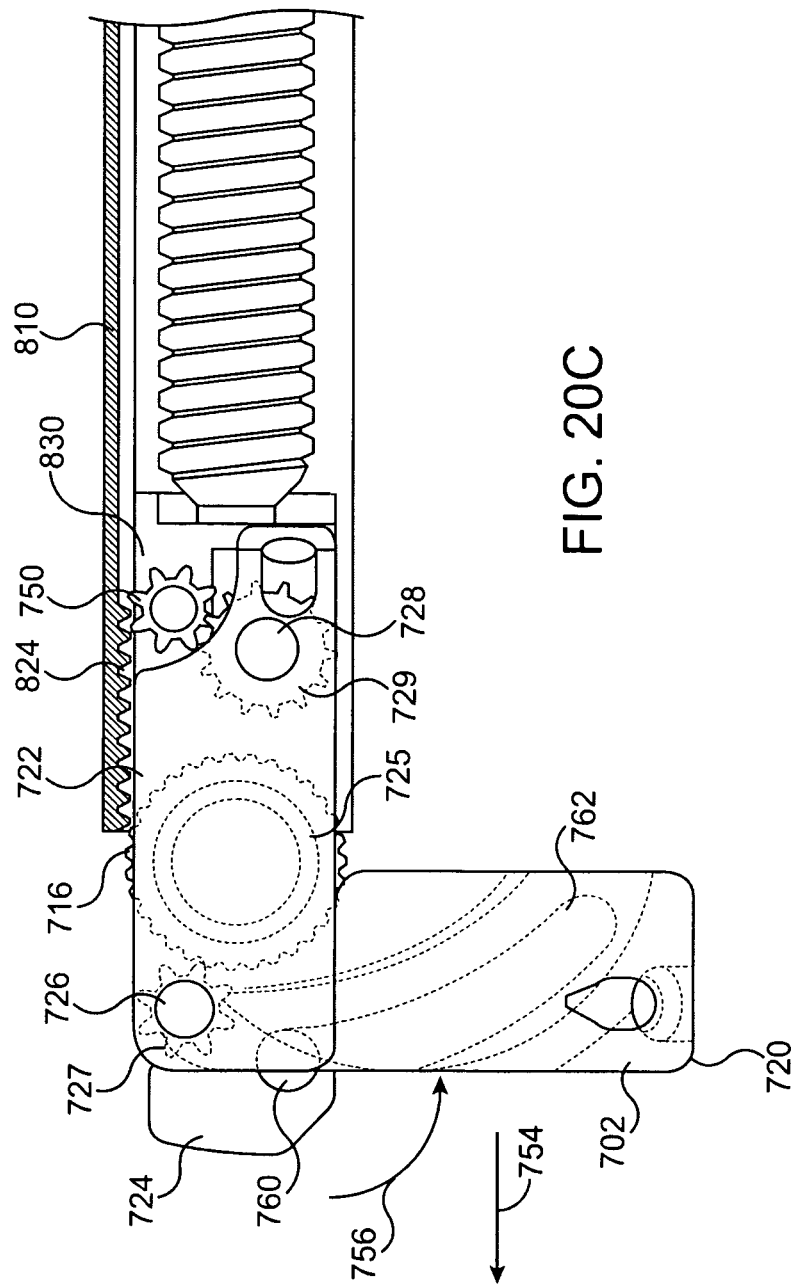

Referring now to FIG. 20C, the components are shown in an intermediate configuration. Distal component 720 and distal component 730 pivot proximally with respect to the proximal components as indicated with an arrow 756. Distal component 720 pivots about joint 726, and distal component 730 pivots about joint 736. Distal component 720 pivots to a stop against proximal component 722. Retention ring gear 725, pivot gear 727 and rack 824 are dimensioned to pivot distal component 702 a pre-determined amount, for example 90 degrees, in response to retention ring gear 716 moving along rack 824. A pinion gear 750 engages rack 824 while distal component 720 is positioned in the final deployed configuration. Pinion gear 750 can be mounted on proximal component 722 and/or inner cartridge part 830. Distal advancement of inner cartridge part 830 causes pinion gear 750 to engage rack 824 and rotate while inner cartridge part 830 advances distally. Pinion gear can 830 engage pivot gear 729 and rotate pivot gear 729. Pivot gear 729 can be fixedly connected to middle component 724 so that rotation of pivot gear 729 about joint 728 pivots middle component 724. Each of the components of the lower support can be similarly dimensioned and positioned to effect pivotal rotation of the lower components.

Middle component 724 can include a protrusion 760. Protrusion 760 can be shaped to slide within a channel 762, groove, or curved slot, formed in distal component 702. Pivotal rotation of middle component 724 can advance protrusion 760 along channel 762. The components of the lower support can include a similar protrusion and channel.

Figure 20D:
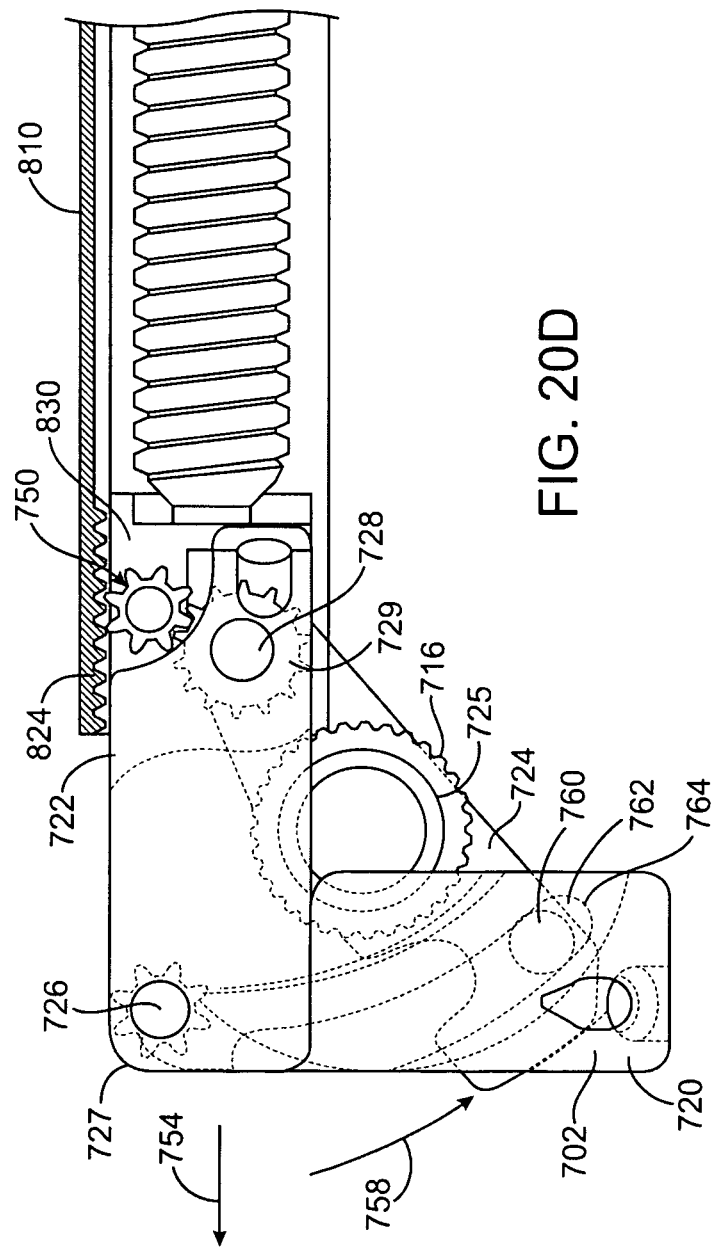

Referring now to FIG. 20D, middle component 324 and middle component 334 of the upper and lower supports, respectively, pivot outward after the distal components are arranged. Stops can be provided on each of the distal and middle components to limit pivoting motion of the middle components about the proximal components. An arrow 758 indicates pivotal motion of middle component 724 toward the final position to form the upper support. The upper and lower support can be fully formed once the middle components pivot to reach the stops. Channel 762 includes an end that receives protrusion 760 to stop pivotal motion of middle component 724. Pinion gear 750, pivot gear 729 and channel 760 can be dimensioned so that pinion gear 750 reaches a distal end of rack 824 when protrusion 760 reaches end 764 of channel 762. Pivot gear 729 rotates about an axis of rotation that can be concentric with a corresponding pivot gear on the lower support 704. Joint 728 rotates about an axis of rotation that can be concentric with pivot gear 729.

Figure 20E:
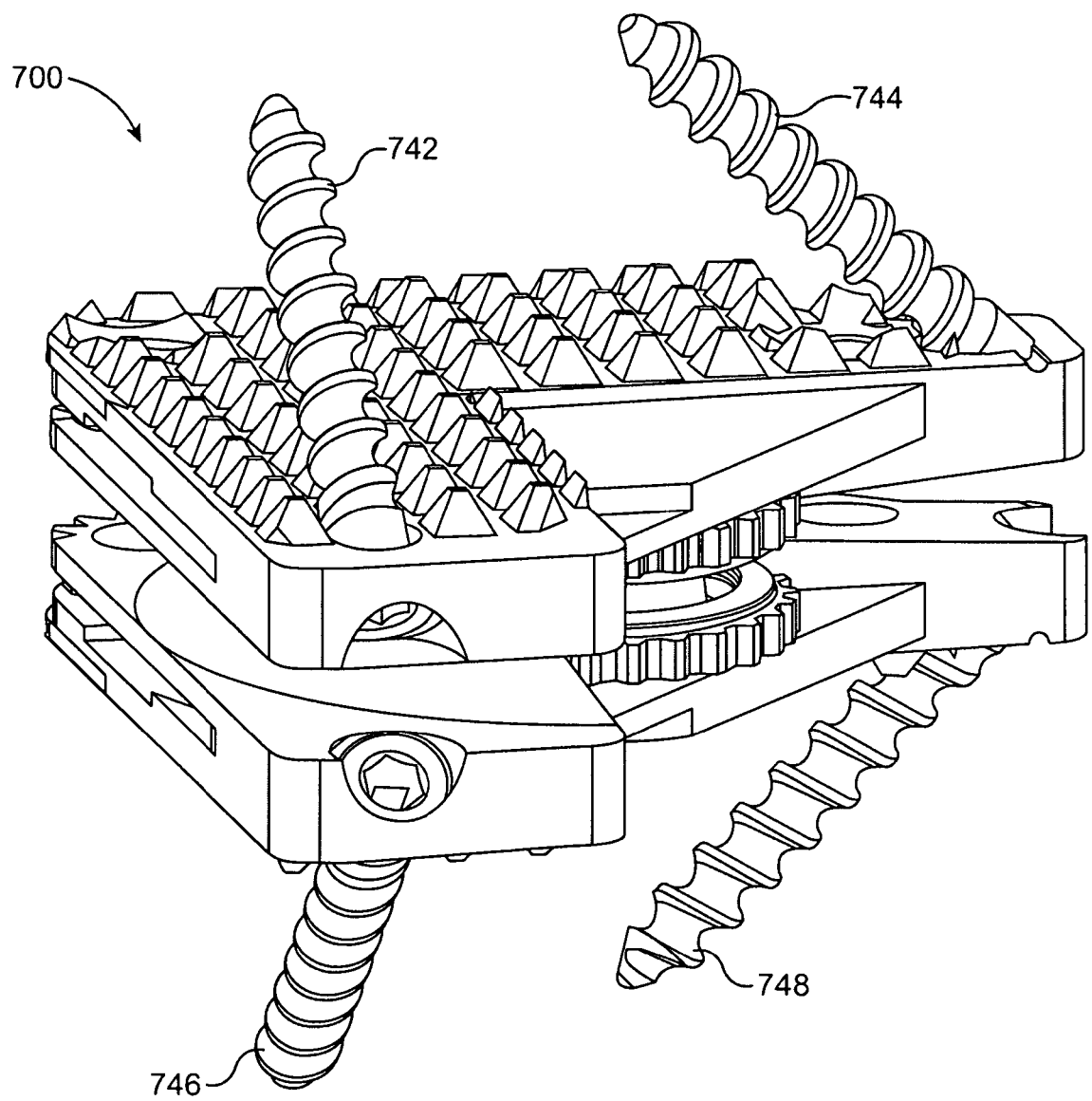

Referring now to FIG. 20E, this isometric view shows middle component 724 and middle component 734 in final positions, such that the upper and lower supports are fully formed. Screws 742, 744, 746 and 748 can be used to anchor the upper support and the lower to the superior and inferior vertebrae, respectively. In some embodiments, the outer cartridge casing is inserted at least partially into and or near the intervertebral space while the upper and lower support components are advanced relative to the outer cartridge casing and into the intervertebral space so as to form the upper and lower supports in the intervertebral space, for example as is shown in FIGS. 15A to 15D. In many embodiments, the upper and lower supports can be formed near the intervertebral space while the outer cartridge casing is positioned outside and near the intervertebral space. In an embodiment, the joint assembly can be inserted partially into the intervertebral space in a rigid wedge configuration and then allowed to freely articulate, so as to limit stretching and promote ligamentotaxis, as described in co-pending U.S. application Ser. No. 10/913,780, filed Aug. 6, 2004, entitled "Methods and Apparatus for Invertebral Disc Prosthesis Insertion", the full disclosure of which has been previously incorporated herein by reference.

The prosthesis as shown in FIG. 20E with fully formed supports and a mobile bearing core member disposed between the supports is capable of several kinds of articulate motion. For example, flexion/extension articulate motion in the anterior and posterior directions, and lateral bending comprising side to side motion on the patient. The prosthesis can also provide axial rotation between the supports, for example rotation about a vertical axis of rotation, that corresponds to a twist along the spine of the patient. The prosthesis can also provide translation between the endplates with the mobile bearing core.

In many embodiments, the angles and lengths of the screws are selected to provide safety. In specific embodiments, the screws are selected and angled to leave bone stock and process substantially intact.

In many embodiments the surfaces of the supports of prosthesis are adapted to anchor the prosthesis to the vertebrae. As can be seen with reference to the above figures, pyramidal anchors disposed in rows can be located on the surfaces of the support components that engage the vertebrae. Such pyramidal anchors can be formed by machining the surfaces to form a serrated surface. The expanded prosthesis can be coated to promote anchoring. In many embodiments, the bone contacting surfaces of the upper and lower supports are coated with a bone growth promoting substance. Examples include Titanium plasma spray coating, hydroxy apatite. In specific embodiments, the bone contacting surfaces can be coated with nano Calcium Phosphate particles to promote bone growth.

The upper and lower supports can comprise many biocompatible materials. In some embodiments the upper and lower supports comprise ceramic, ceramic composite, polymer, cobalt chrome, titanium and combinations thereof.

FIGS. 21A to 21D show posterior and/or posterior lateral access to the intervertebral space, according to embodiments of the present invention. Embodiments provide in situ disc expansion within the disc space to provide minimal disruption to the posterior bone support, facets and nerves and to retain the anatomical structures. In many embodiments, two far posterio-lateral minimally invasive approaches are used so as to allow for the minimum of facet (zygophyseal) joint removal such that the facet joints remain substantially intact. In many embodiments a Total Disc Replacement (TDR) is provided.

Figure 21A:
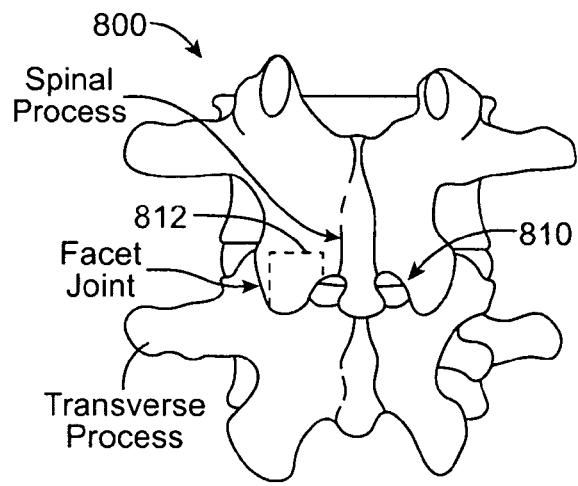
FIGS. 21A to 21D show posterior lateral access to the intervertebral space, according to embodiments of the present invention.
Figure 21B:
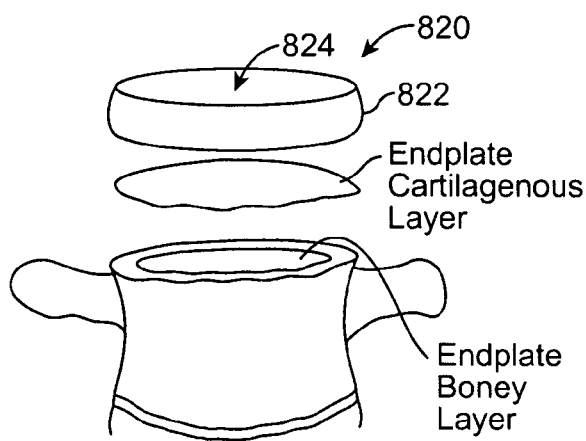
Figure 21C:
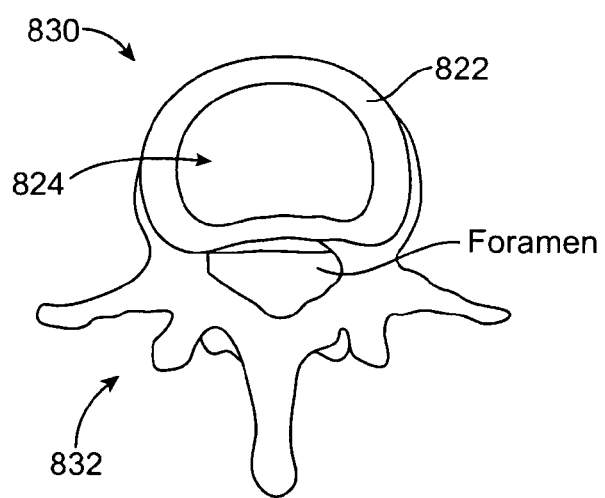
Figure 21D:
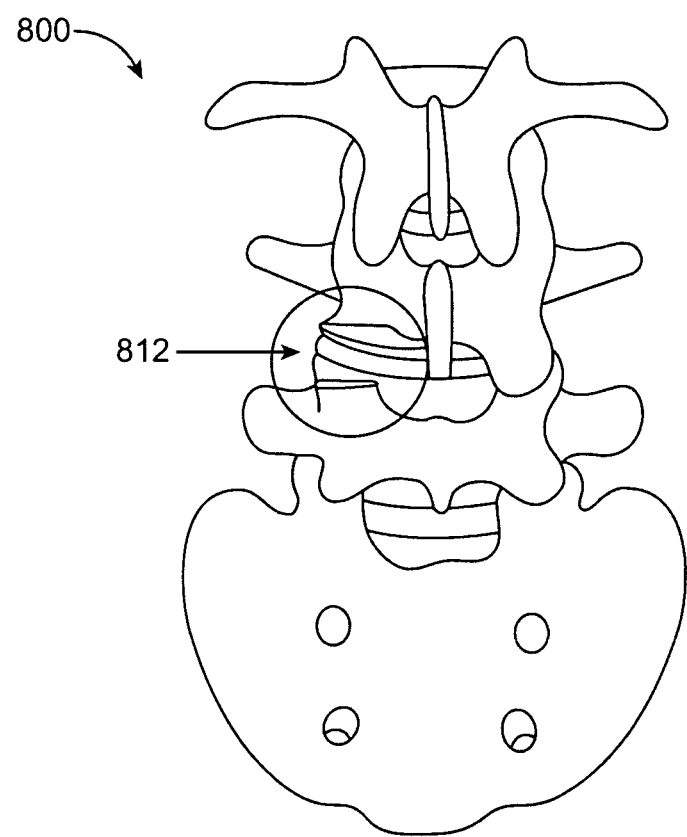

An anterior aspect of the lumbar spine is shown in FIG. 21B. A posterior aspect 800 of the lumbar spine includes several spinal processes as shown in FIG. 8A. A disc 820 includes an annulus 822 and a nucleus 823. In many embodiments, these processes are remain substantially intact following posterior and posterior-lateral insertion of the intervertebral prosthesis. In some embodiments, a naturally occurring and pre-existing opening 810 is used to access disc 820 posteriorly. A suitably sized instrument, for example about a 9 mm diameter size instrument, can be introduced into the naturally occurring intervertebral space through opening 810. In specific embodiments, the upper and lower supports each comprise about a 9 mm narrow profile configuration to pass through pre-existing opening 810. In some embodiments, an opening 812 can be formed to access the intervertebral space, for example as shown in FIGS. 21A and 21D. An instrument with a narrow profile size of about 13 mm across may be used with such openings. Opening 810 can comprise cuts formed the inferior articular spinal process and/or cuts formed in the superior spinal process that comprise the facet joint, or zygophyseal joint, of adjacent spinal vertebrae. In some embodiments, the opening may be formed in a manner similar to that which is performed with Transforaminal Interbody Fusion (TLIF). In many embodiments, symmetric opposing openings are used to access the intervertebral space, for example pre-existing openings and/or formed openings. In many embodiments, a posterior lateral approach through soft tissue, for example a Wiltse approach is used to access the posterior aspect of the spine. A superior view of a lumbar vertebra is shown in FIG. 21C. In many embodiments, at least a portion of the surgical instruments and/or the expandable articulate prosthesis will pass through the vertebral foramen, for example a foramen as shown in FIG. 21C. As the expandable articulate prosthesis may pass at least partially through the foramen, embodiments of the present invention may be referred to as Transforaminal Interbody Articulation (TLIA, or TIA). A posterior lateral approach 832 permits access to disc 820 through the vertebral foramen.

In some embodiments it may be desirable to access the disc and intervertebral space with an anterior or anterior lateral approach using the expandable articulate prosthesis. With an anterior approach the expandable prosthesis can minimize movement or disruption of the blood vessels in front of the spine (descending aorta and vena cava), minimize the formation of scar tissue during healing following device placement by reducing invasiveness of the anterior placement, avoid abnormal posterior anatomy would make an anterior approach more appropriate for the patient (e.g. unusual nerve location).

FIGS. 22A to 22E show a method for introducing a joint assembly into an intervertebral disc space, in accordance with embodiments of the present invention. Annulus 822 of disc 820 is thicker anteriorly than posteriorly. A first opening 920A is formed in a posterior portion of annulus 822 with penetration of the annulus into nucleus 823 of disc 820. A second opening 920B is formed in a posterior portion of annulus 822 with penetration of the annulus into nucleus 823. A tissue removal instrument 930 is inserted through opening 920A into nucleus 823 to remove nucleus 823. A viewing instrument 932, comprising an endoscope, arthroscope, fiber optic or the like, is inserted into opening 920B to permit viewing of the removal of nucleus 823. In some embodiments, the instruments can be switched following removal of some tissue to facilitated complete removal of the nucleus, for example viewing instrument 932 inserted into opening 920A and tissue removal instrument 930 inserted into opening 920B. Bilateral disc entry as shown can facilitate disc decompression, insertion of the expandable prosthesis, and anchoring of the prosthetic disc.

An expandable member template 934B can be inserted into the evacuated disc space through opening 92A with instrument 934 to determine that sufficient tissue has been removed. Expandable member template 934B may comprise an expandable balloon that can be filled with a radiopaque material. The balloon may comprise a radiopaque material, and be inflated with a gas and/or saline and the like. In specific embodiments, a Mylar balloon is filled with Barium solution and the Mylar Balloon has an expanded shape that corresponds to the foot print of the expandable articulate prosthesis. After viewing the shape of the expanded member, for example with fluoroscopy, additional tissue may be removed if desired. In some embodiments, the template may have radiographic markers to indict the midline and anterior/posterior orientation. A fluoroscopic image of the template can be saved and compared to the prosthetic disc image. In many embodiments, the template has a lower height than the prosthesis that is sufficient to evaluate the footprint of material removed and ensure that sufficient material has been removed to allow expansion of the prosthetic disc.

In some embodiments, a portion of the annulus may be removed to guide the expandable prosthesis during delivery into the intervertebral space. The annulus comprises Type II collagen, which is strong, and can guide placement of the prosthesis in some embodiments. In specific embodiments, the annulus can be shaped during the discectomy to guide the prosthesis during deployment into the evacuated space, and the expandable articulate prosthesis may be press fit anteriorly into the annular annulus so as to resist rotation within the disc space. In specific embodiments, the interior shape of the annulus formed during discectomy corresponds to structures on the expandable articulate prosthesis, for example a foot print of the expandable articulate prosthesis.

An expandable articulate prosthesis 942 can be deployed with a deployment instrument 940 inserted through opening 920A. Deployment instrument 940 may comprise racks, gears, pulleys, cables and the like as described above to expand prosthesis 942 as the prosthesis is advanced into the disc space. A distractor 950 can be inserted through opening 920B to distract the adjacent vertebrae while prosthesis is deployed with expansion into the evacuated disc space. An instrument 960 can be inserted into opening 920A to adjust the location of expandable intervertebral prosthesis 942 after the upper and lower supports are fully formed. Adjustment to the location of the disc with fully formed supports can be done while distractor 950 is inserted through opening 920B. Alignment can be accomplished using natural indicia such as the pedicles and/or with radiopaque markers, for example markers on the prosthesis. Screws can be passed through opening 920A to anchor the upper and lower supports on one side of the prosthesis, and screws can be passed through opening 920B to anchor the upper and lower supports on the other side of the prosthesis.

Figure 23A:
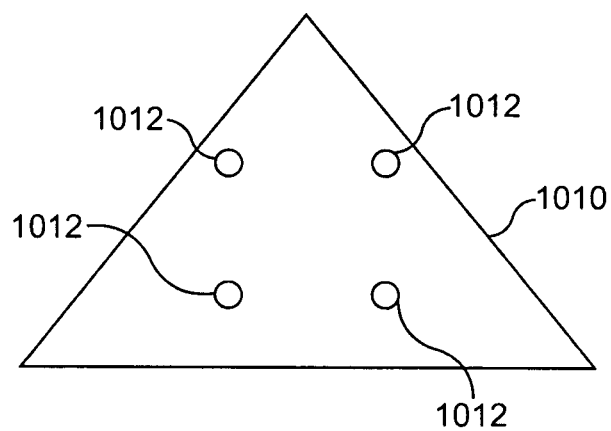
FIGS. 23A and 23B show radiopaque markers on upper and lower supports of an expandable intervertebral prosthesis, according to embodiments of the present invention.
Figure 23B:
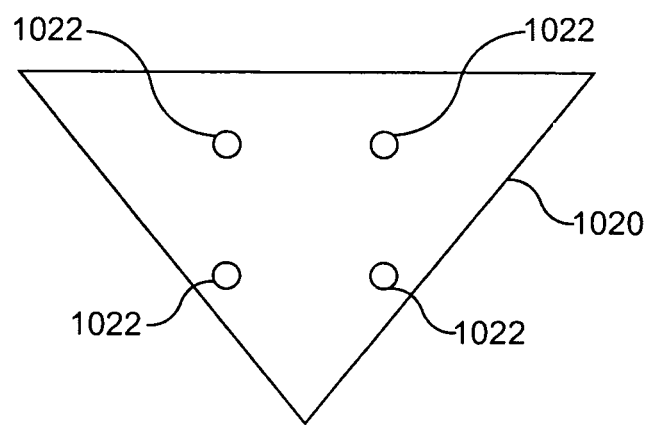

FIGS. 23A and 23B show radiopaque markers on upper and lower supports of an expandable intervertebral prosthesis, according to embodiments of the present invention. FIG. 23A shows a superior view of an upper expandable support 1010 that comprises radiopaque markers 1012 positioned on the upper support. FIG. 23B shows an inferior view of a lower expandable support 1020 that comprises radiopaque markers 1012 positioned on the lower support. The radio opaque markers can be used to detect alignment of the upper support and lower support in a manner similar to that described in U.S. application Ser. No. 11/187,733, filed Jul. 21, 2005, entitled "Intervertebral Prosthesis Placement Instrument"; U.S. application Ser. No. 10/903,913, filed Jul. 30, 2004, entitled "Intervertebral Prosthetic Disc with Metallic Core", U.S. Publ. No. 2006/0025862, the full disclosure of which has been previously incorporated by reference. The markers can be helpful in detecting anterior posterior alignment with fluoroscopy, lateral alignment with the pedicles and rotation of the upper and/or lower support in relation to the pedicles. The markers can be used in addition to other indicia, for example with the pedicles to ensure that the posterior lateral edges of the inserted disc are equidistant from the center of the pedicles and at the same disc level.

Figure 24A:
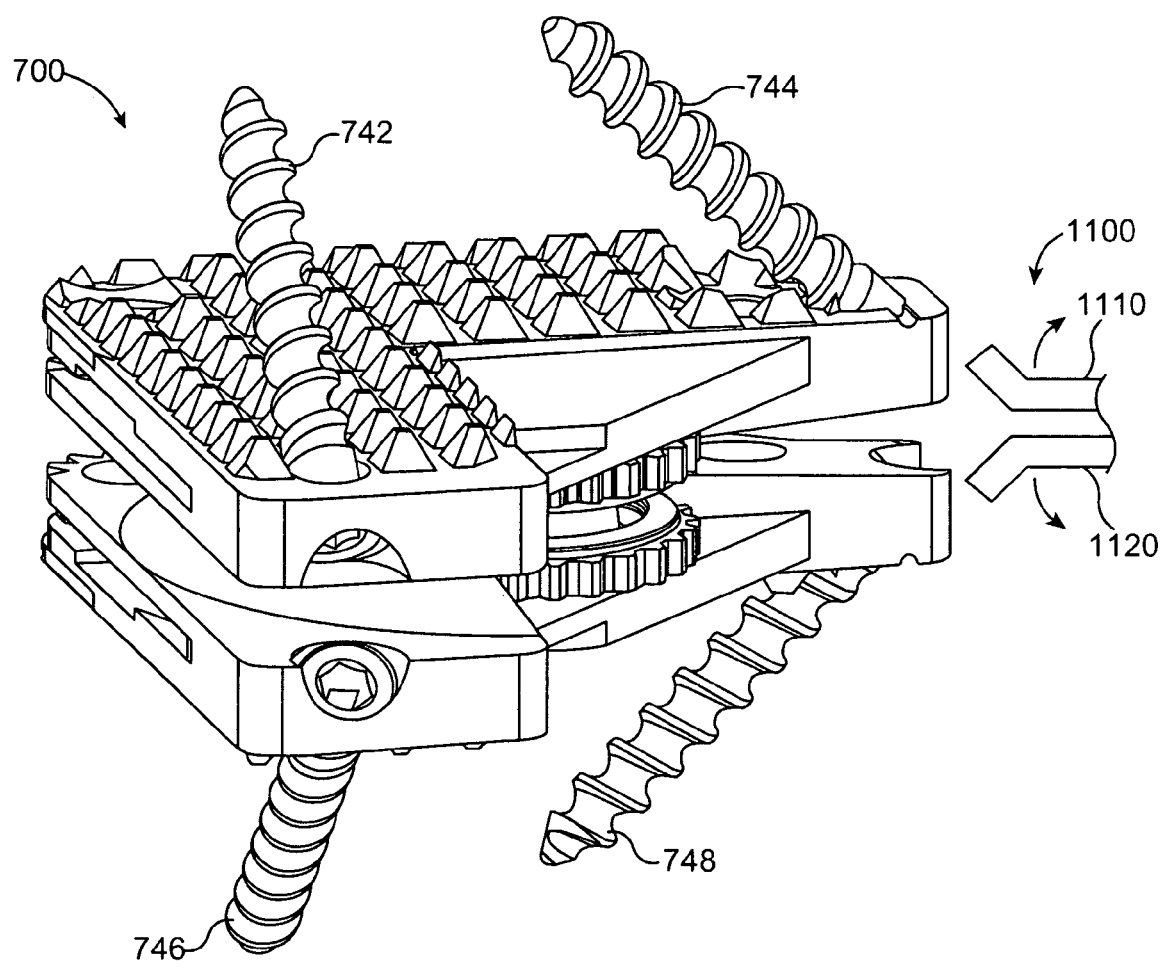
FIGS. 24A to 24E show a method of removing an expandable intervertebral prosthesis as in FIGS. 20A to 20E, in accordance with embodiments of the present invention.
Figure 24B:
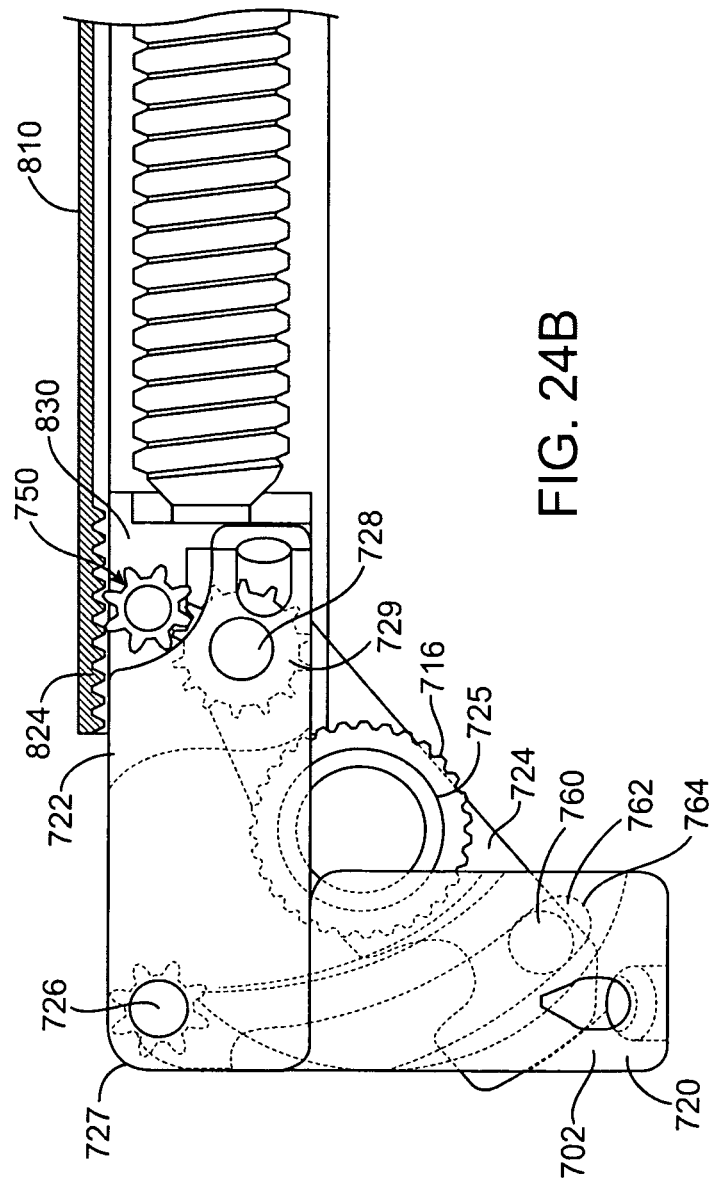
Figure 24C:
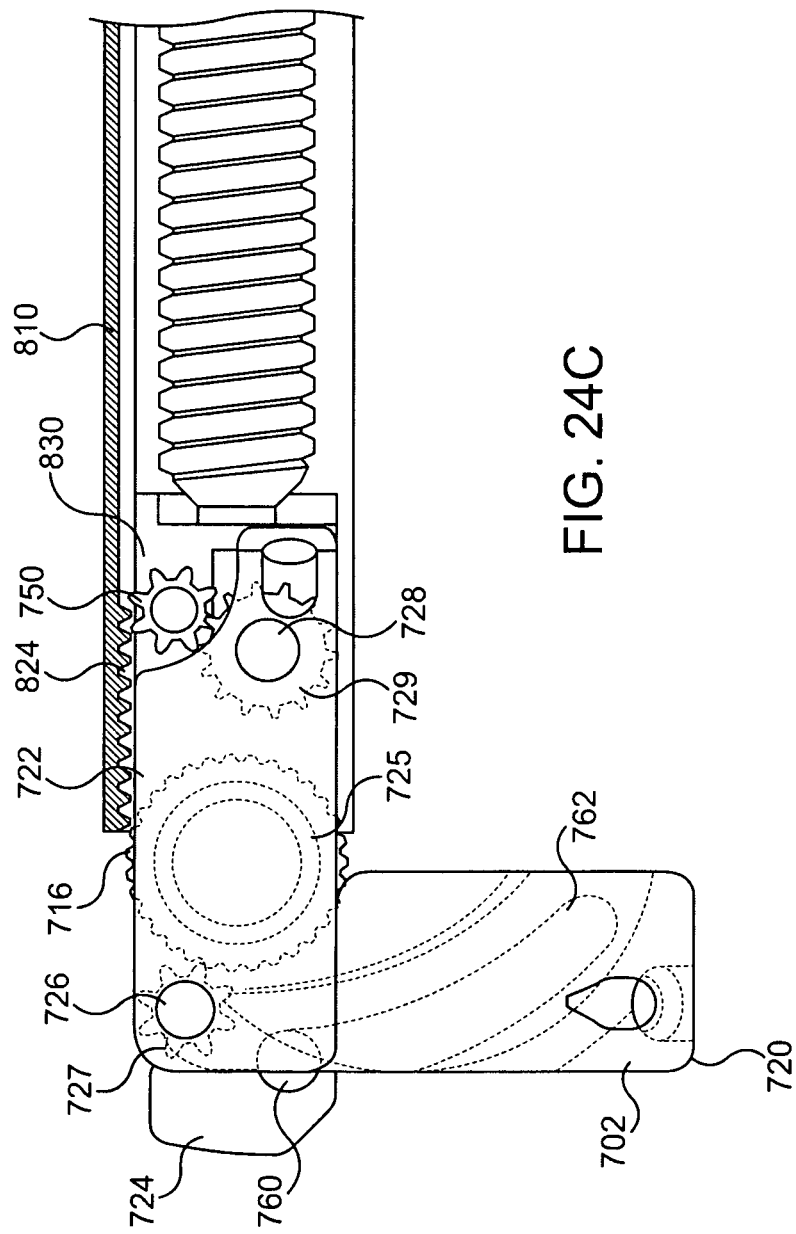
Figure 24D:
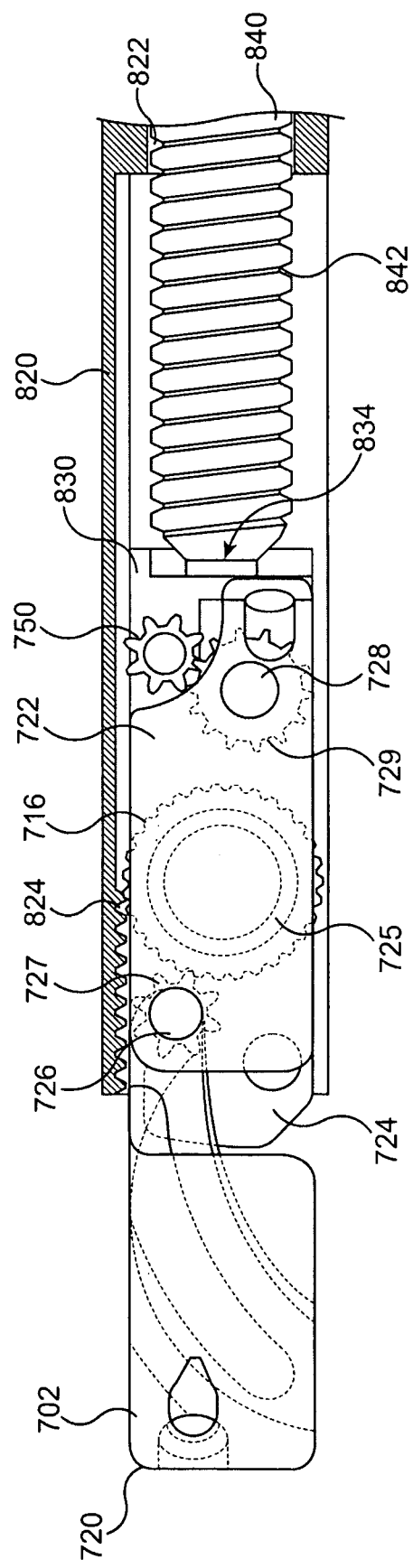
Figure 24E:
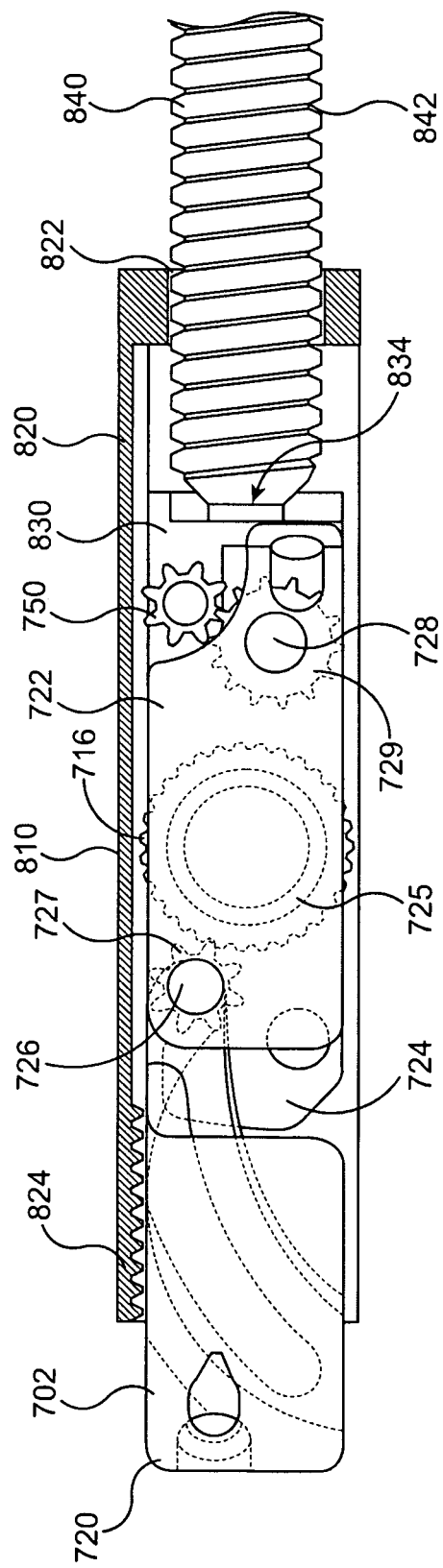
Figure 25A:
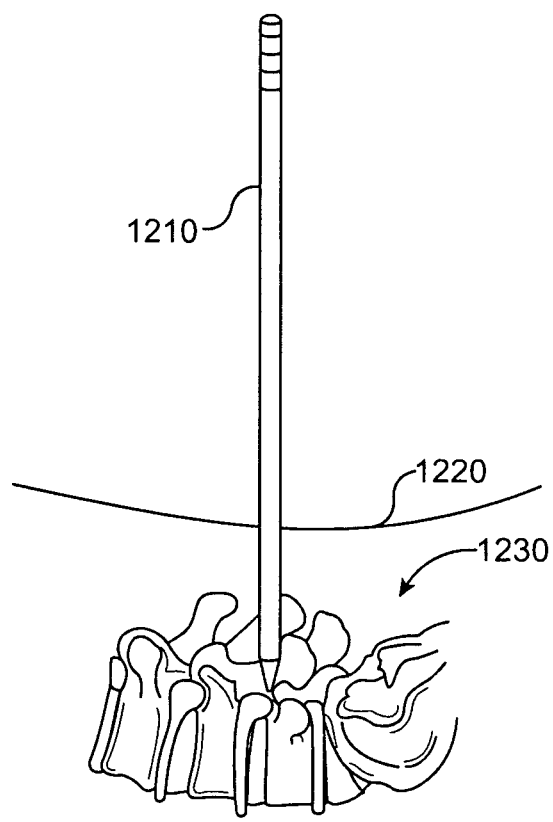
FIGS. 25A to 25D show blunt dissection of tissue to access the intervertebral space, according to embodiments of the present invention.
Figure 25B:
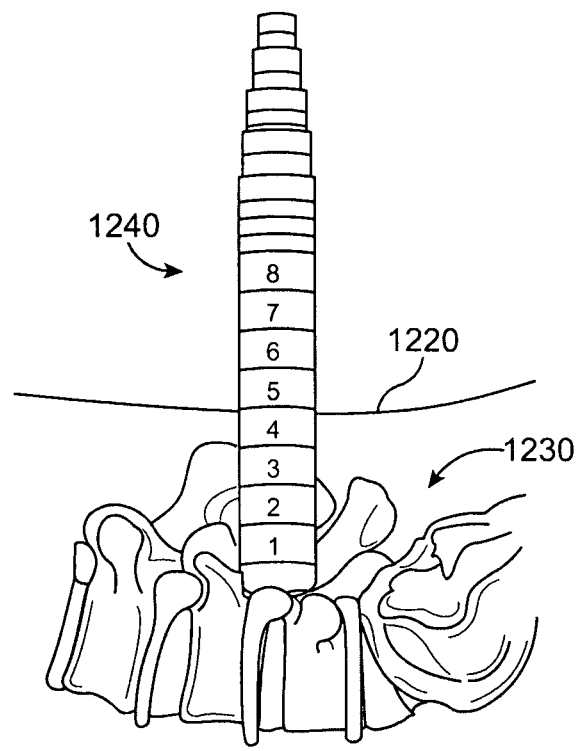
Figure 25C:
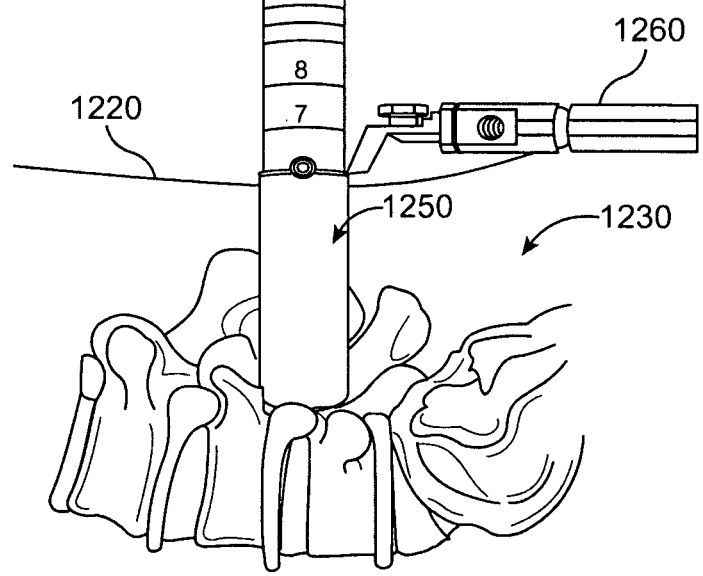
Figure 25D:
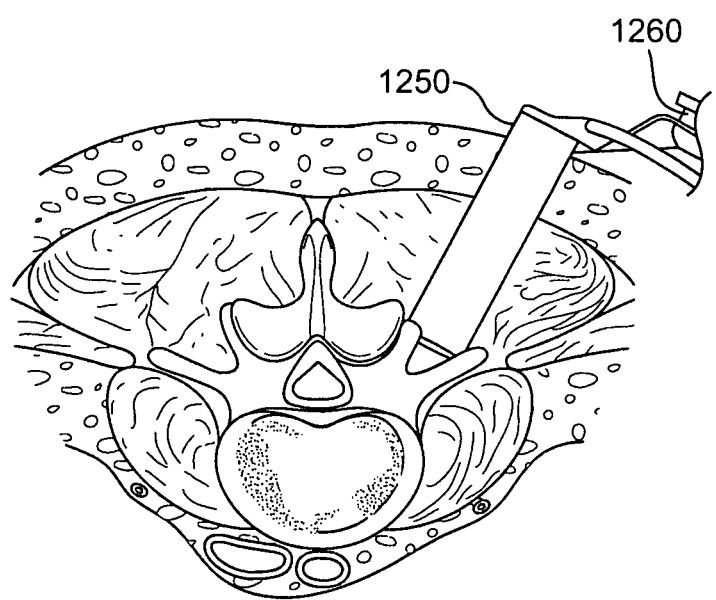

FIGS. 24A to 24E show a method of removing an expandable intervertebral prosthesis as in FIGS. 20A to 20E, in accordance with embodiments of the present invention. Screws 742, 744, 746 and 748 can be removed. An instrument with a casing as described above is introduced into the intervertebral space. The instrument comprises a distal end 1100 with an upper protrusion structure 1110 to engage the upper support through the screw hole for screw 744 and a lower protrusion structure 1120 to engage the lower support through the screw hole for screw 748, for example as shown in FIG. 24A. Other engagement structures on the supports and instrument may be used. Outer cartridge casing 820 is advanced such that pinion gear 750 is engaged with rack 824, for example as shown in FIG. 24B. The implant may also be retracted while engaged with the protrusion structures such that the rack and pinion gear are engaged. This engagement causes middle component 724 to swing under the proximal component in a narrow profile configuration, for example as shown in FIG. 24C. Further retraction of the prosthesis and/or advancement of the casing engages retention ring gear 716 with rack 824 so as to pivot the distal component into the elongate and narrow profile configuration as shown in FIG. 24D. Retraction of the expandable intervertebral can be continued so as to retract and fully collapse the prosthesis to the narrow profile configuration as shown in FIG. 24E.

FIGS. 25A to 25D show blunt dissection of tissue to access the intervertebral space, according to embodiments of the present invention. A dilator 1210, for example a 20 gauge needle, is passed through a skin 1220 of the patient to a posterior aspect 1230 of the spine of the patient. Sequential dilators 1240 comprising blunt dissection instruments are sequentially passed over dilator 1210 and each other until the tissue is dilated to a desired size. An operative tube 1250 is place over the sequential dilators to provide access to posterior aspect 1230 of the spine. Operative tube 1250 can be locked in place with an arm 1260. The dilators can then be removed to establish an operative corridor. A posterior lateral approach can be made though muscle tissue in a minimally invasive fashion. Many of the other approaches described above can be made in a similar minimally invasive fashion with blunt dissection.

Figure 26:
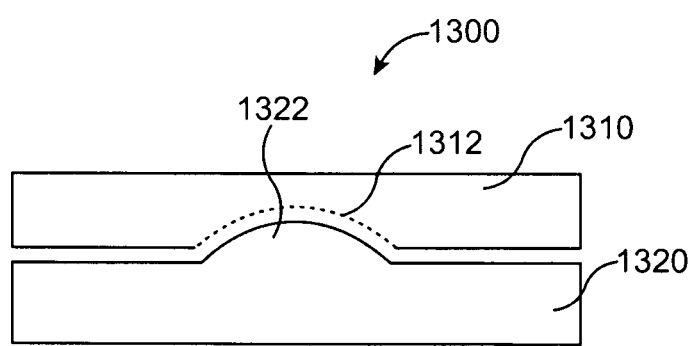
FIG. 26 shows an expandable intervertebral prosthesis comprising an upper support that engages a lower support to articulate, according to embodiments of the present invention.

FIG. 26 shows an expandable intervertebral prosthesis 1300 comprising an upper support that engages a lower support to articulate, according to embodiments of the present invention. Upper support 1310 comprises an expandable support as described above. Lower support 1320 comprises an expandable support as described above. Lower support 1320 comprises a convex protrusion 1322 to engage upper support 1310. Upper support 1310 comprises a concave recessed surface 1312 to receive convex protrusion 1322. Convex protrusion 1322 and concave recessed surface 1322 articulate the upper and lower supports. The upper and lower supports can articulate with at least one of a flexion/extension, a lateral bending or an axial rotation.

Figure 27:
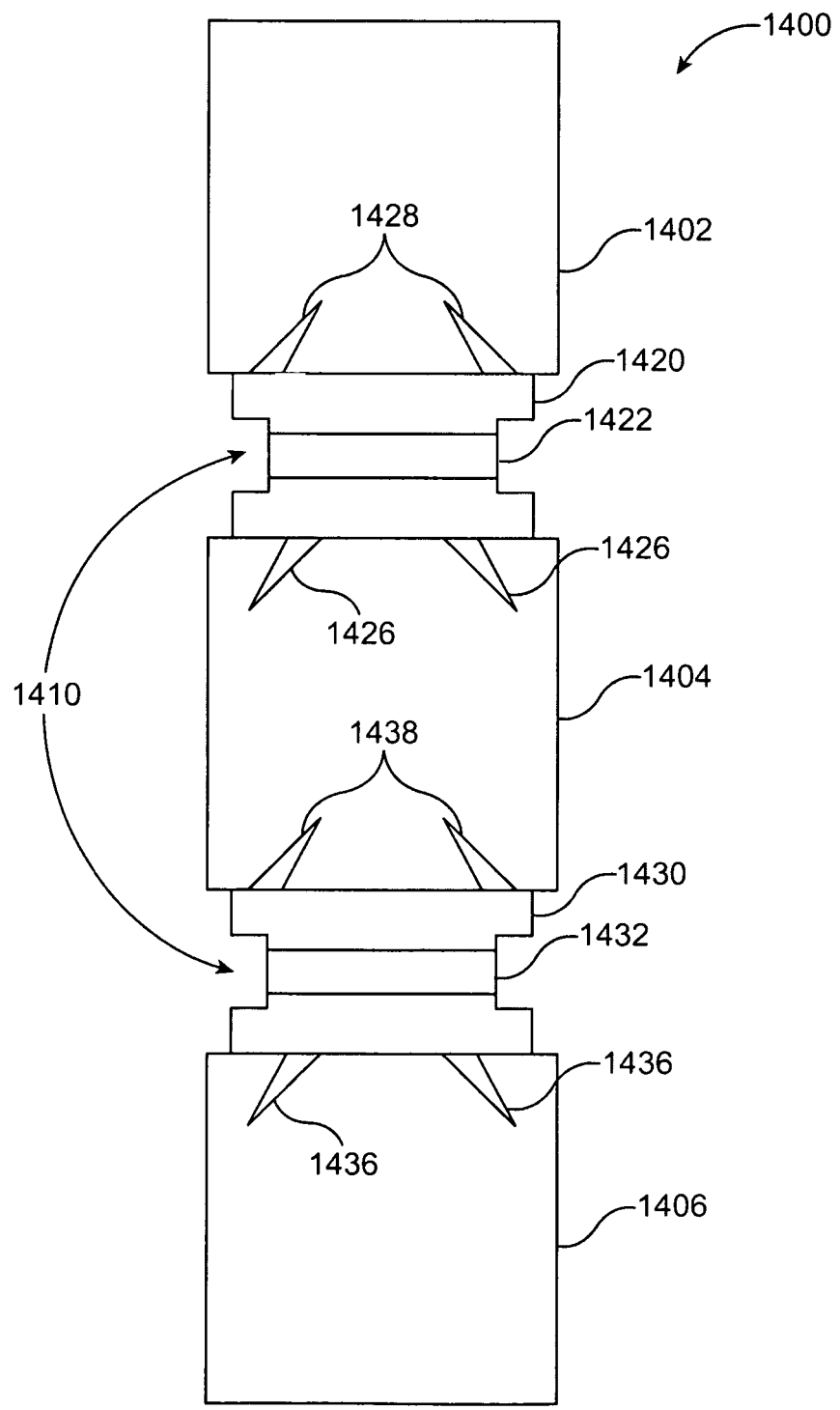
FIG. 27 shows self expanding prostheses that can be stacked in adjacent intervertebral spaces, according to embodiments of the present invention.

Referring now to FIG. 27, self expanding prostheses can be stacked in adjacent intervertebral spaces, according to embodiments of the present invention. A stacked arrangement 1400 comprises intervertebral prostheses in adjacent intervertebral spaces. Adjacent intervertebral spaces 1410 are defined by an upper vertebra 1402, a middle vertebra 1404 and a lower vertebra 1406. In many embodiments, the prosthesis comprises anchors adapted to permit stacking with another prosthesis positioned in an adjacent intervertebral space. An upper prosthesis 1420 comprises upper anchors 1428 and lower anchors 1426. Upper prosthesis 1420 comprises an expandable upper and lower support with a mobile bearing core member 1422 located between the upper and lower expandable supports as described above. A lower prosthesis 1430 comprises upper anchors 1438 and lower anchors 1436. Lower prosthesis 1430 comprises an expandable upper and lower support with a mobile bearing core member 1432 located between the upper and lower support as described above. The angles of the screws and/or other anchors may be oriented and positioned with lengths to permit stacking of multiple prostheses in adjacent intervertebral spaces as described in U.S. Appl. No. 60/820,769, filed on Jul. 28, 2006, entitled "Spinal Prosthesis with Offset Anchors", the full disclosure of which has been previously incorporated by reference. Lower anchors 1426 of upper prosthesis 1420 are oriented outward and upper anchors 1438 of lower prosthesis 1430 are oriented inward, such that the tips of the anchors from each of the prostheses avoid each other. In a specific embodiment a first expandable articulate prosthesis is placed with a posterior and/or posterior lateral approach in the intervertebral space defined by L4 and L5 and a second expandable articulate prosthesis is placed with a posterior/posterior lateral approach in the intervertebral space defined by L3 and L4.

Figure 27A:
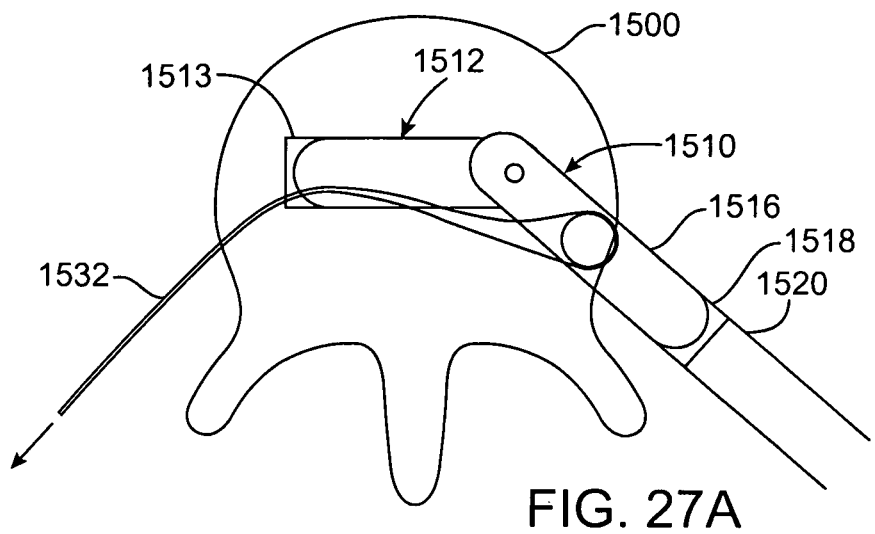
FIGS. 27A to 27C show in situ deployment of an expandable articulate intervertebral prosthesis in an intervertebral space with a placement instrument and a contralateral placement instrument, according to embodiments of the present invention.
Figure 27B:
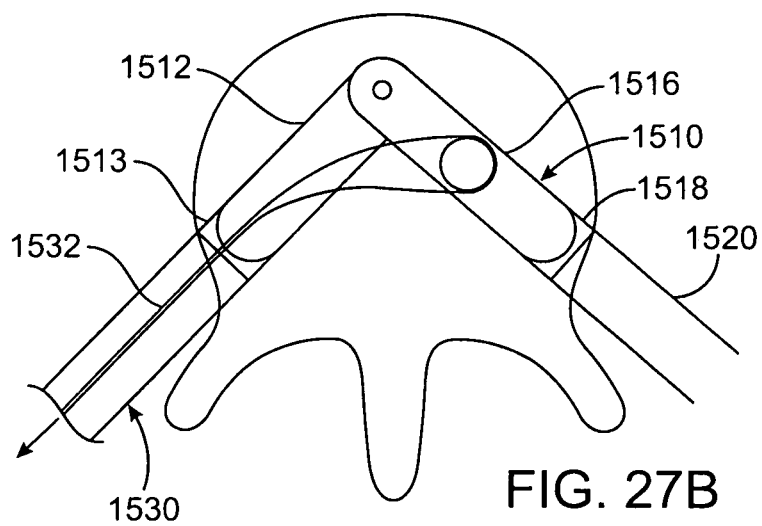
Figure 27C:
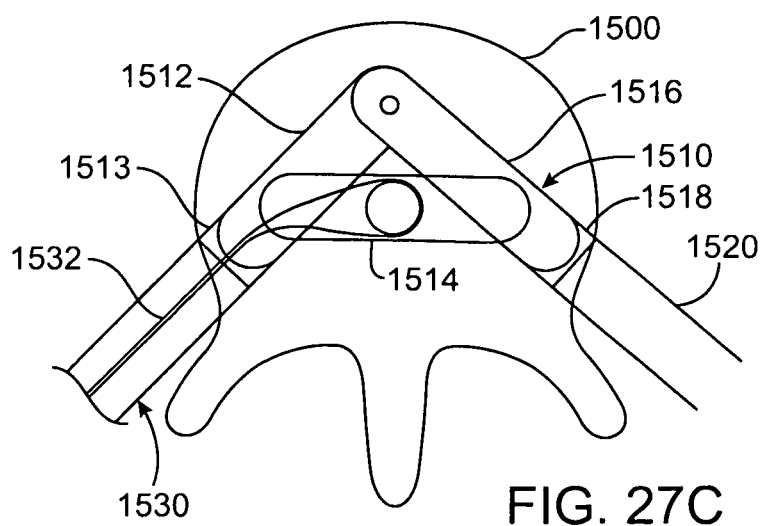
Figure 29A:
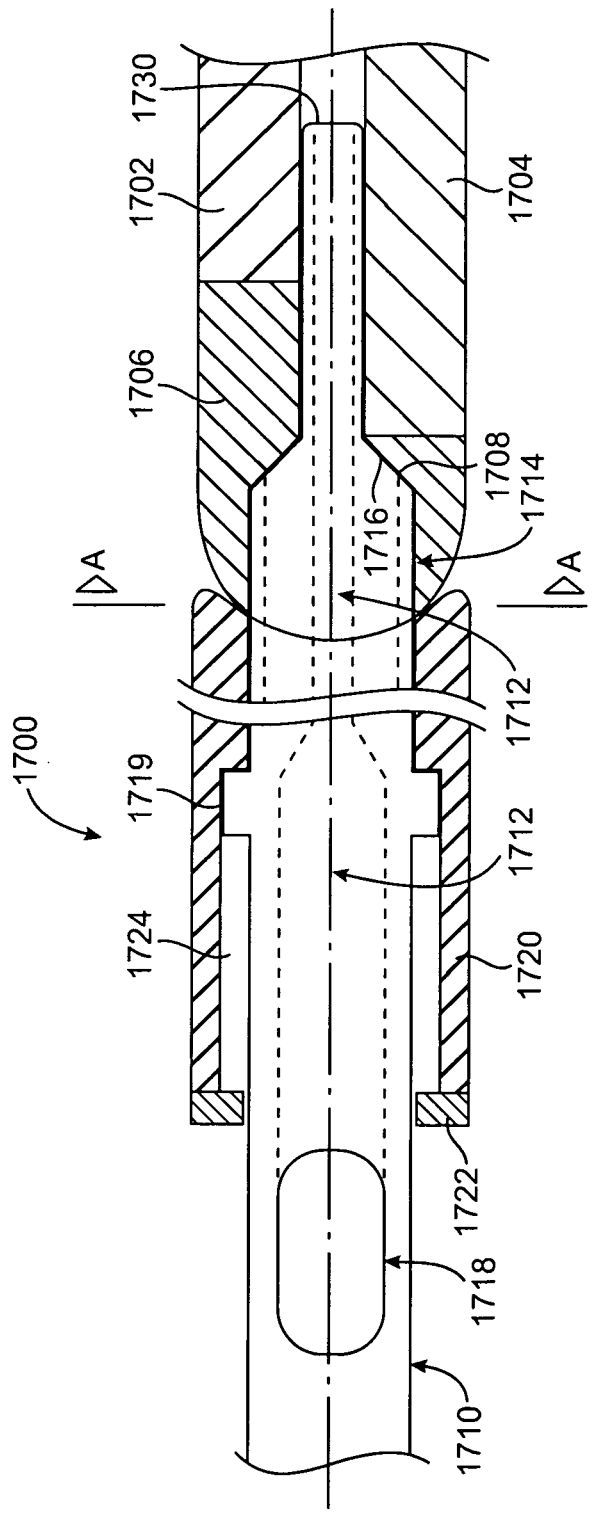
FIGS. 29A to 29D show a contralateral placement instrument as in FIGS. 27A to 27C, according to embodiments of the present invention.
Figure 29B:
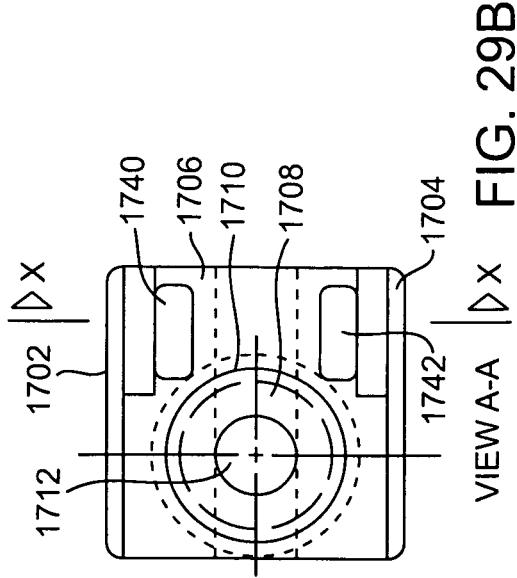
Figure 29C:
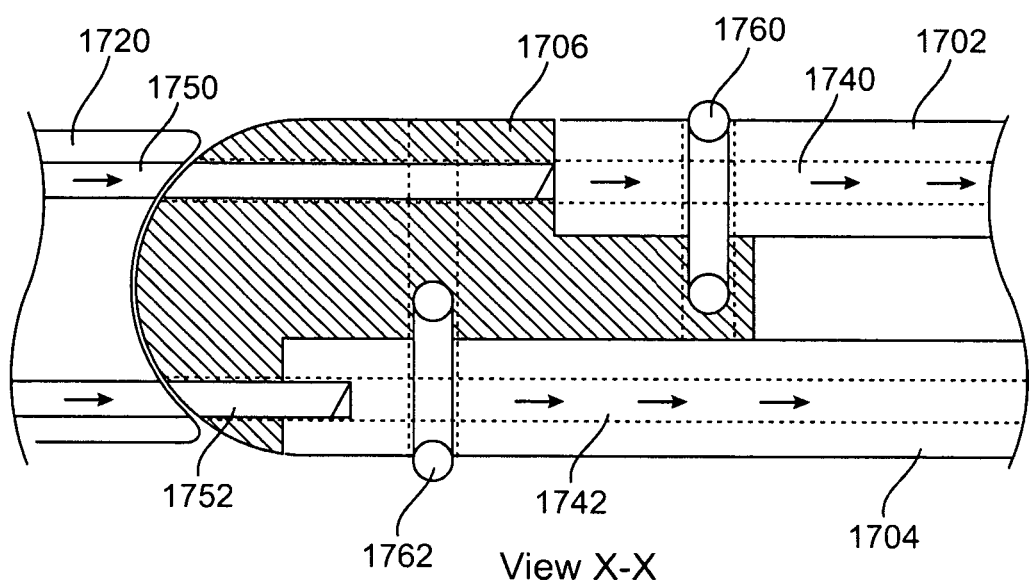
Figure 29D:
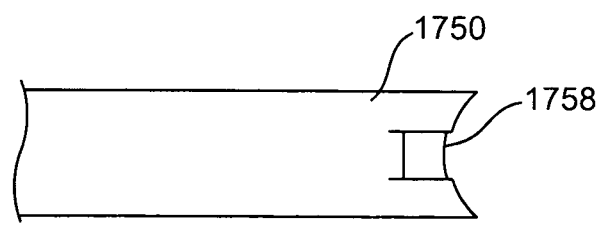

FIGS. 27A to 27C show in situ deployment of an expandable articulate intervertebral prosthesis 1510 in an intervertebral space with a placement instrument and a contralateral placement instrument, according to embodiments of the present invention. An inferior vertebra 1500 comprises spinal processes as shown above. Two posterior lateral access ports can be formed with blunt dissection with a Wiltse approach as described above. In many embodiments, the annulus remains substantially intact following removal of the nucleus, and the prosthesis is positioned within the annulus via posterior lateral access openings in the annulus as described above. A placement instrument 1520 is used to advance prosthesis 1510 and a contralateral placement instrument 1530 can be used to manipulate the prosthesis 1510 during deployment. Placement instrument 1520 can be attached to prosthesis 1510 with a threaded spacer 1524 that is positioned between the upper and lower supports.

Prosthesis 1510 can comprise an elongate narrow profile configuration and an expanded wide profile configuration as described above and can be advanced into the intervertebral space in the elongate narrow profile configuration. Prosthesis 1510 comprises upper and lower supports, and each support can comprise a distal support component, a proximal support component and a middle support component as described above. A distal component 1512 is pivotally connected to a proximal component 1516. While the components are advanced into the intervertebral space, distal component 1512 pivots in relation to proximal component 1516. In specific embodiments, distal component 1512 is a final position when pivoted to 90 degrees. A threaded leading edge spacer 1513, or distal spacer, can be attached to distal component 1512 to connect the distal component to contralateral placement instrument 1530 with rotation of the contralateral placement instrument. A threaded trailing edge spacer 1518, or proximal spacer, can be attached to proximal component 1516 to connect the proximal component with placement instrument 1520 with rotation of the placement instrument. A middle component 1514 can pivot into position after the distal component has pivoted into position as described above.

A gut, or cable 1532 can be used to expand prosthesis 1510. Cable 1532 can comprise, nylon or other suitable material, for example surgical suture material. Following preparation of the intervertebral space, for example after a discectomy, cable 1532 can be threaded, or advanced, into one surgical access port, through the prepared intervertebral space and/or openings in the annulus, and out the other surgical access port. Tension in a proximal direction can be applied to cable 1532 to expand prosthesis 1510. Contralateral placement instrument 1532 comprises an opening to receive cable 1532 such that contralateral placement instrument 1532 can be advanced distally to engage distal component 1512. Cable 1532 can guide the contralateral placement instrument into position as the contralateral placement instrument is advanced distally so as to engage the leading edge threaded spacer. The leading edge threaded spacer can be positioned between the distal components and attached to the distal components with a cable. Threaded connection of the contralateral placement instrument to the leading edge spacer connects contralateral placement instrument 1530 to distal component 1512. Tension applied to cable 1532 can pivot distal component 1512 into the deployed position. Additional displacement of cable 1532 can pivot middle component 1514 into position.

In many embodiments, the fully formed upper and lower supports can be locked into position with a locking mechanism. The locking mechanism may comprise an insertable elongate member, a cam and/or a ratchet. Channels, or longitudinal slots, can be formed in the components to receive an elongate member after the supports are fully formed, for example a rod. The longitudinal slots can extend substantially along the length of the respective component, for example along the length of the proximal component and/or along the length of the distal component. In many embodiments, the middle component swings clear of the channels when pivoted into position, such that the elongate member can be inserted into the slot while the middle component is in the deployed wide profile position. Interference of the elongate member with the middle component and/or proximal and distal components locks the components into position while the support is fully formed. The elongate member may comprise an oval rod, a rectangular rod, and/or a circular rod and the like. The rods can be removed to collapse and remove the prosthesis. In many embodiments, the rods and disc components may comprise a ratchet mechanism which retains the elongate member in position in the longitudinal slots after insertion. In some embodiments, a cam mechanism is provided that rotates into position so as to lock the components into position, for example upon rotation of the middle component to the deployed wide profile configuration.

In many embodiments, the placement instrument and contralateral placement instrument are both connected to the prosthesis, for example simultaneously connected to the prosthesis. This connection of both placement instruments can be used to manipulate the prosthesis into position. In specific embodiments, both instruments are simultaneously connected to the articulate, expanded prosthesis while the upper and lower supports are in fully formed and locked positions as described above and the support positioned in the intervertebral space and/or annulus.

FIGS. 28A to 28D show a placement instrument 1600 as in FIGS. 27A to 27C, according to embodiments of the present invention. The placement instrument can be inserted posteriorly through the canal and/or foramen so as to engage the bony endplates near the disc space. In many embodiments, the placement instrument is inserted after two minimally invasive Wiltse incisions and/or dissections and a discectomy that uses a posterior parallel distractor. Placement instrument 1600 comprises a distractor with a distractor tip 1630 that can be inserted at least partially into the intervertebral space. Instrument 1600 comprises a stop to limit penetration of distractor tip 1630. Instrument 1600 comprises handles 1610 to distract the adjacent vertebrae. Instrument 1600 comprises a hinge 1620 that opens distractor tip 1630 upon inward motion of handles 1610.

Instrument 1600 is adapted to pass the prostheses in an elongate narrow profile configuration into the intervertebral space. Distractor tip 1630 comprises a channel 1640 with grooves 1642 formed therein. Channel 1640 is dimensioned to pass the prosthesis in an elongate narrow profile configuration. Grooves 1642 are dimensioned and spaced to receive anchors on the external surfaces of the support components, for example pyramidal components as described above. In some embodiments, the anchors may comprise elongate pyramidal anchors and or elongate keels or flanges and the grooves adapted to pass the elongate anchors with the groove aligned with the elongate anchor. In many embodiments, channel 1640 is sized to distract the vertebrae with distractor tip 1630 while the elongate prosthesis slides down channel 1640. Near hinge 1620, channel 1640 can be sized to pass the prosthesis with a sliding fit.

Instrument 1600 comprises an insertion tool 1650 to advance the prosthesis along channel 1640 so as to advance the prosthesis into the intervertebral space. Insertion tool 1650 comprises a shaft 1654 and a handle 1652. Handle 1652 is connected to shaft 1654. In many embodiments handle 1652 comprises a grub screw, and handle 1652 and shaft 1654 comprise strong materials such that handle 1652 can be hammered so as to drive the prosthesis distally into the intervertebral space and distract the vertebrae with separation of distal tip 1630.

FIGS. 29A to 29D show a contralateral placement instrument 1700 as in FIGS. 27A to 27C, according to embodiments of the present invention. In many embodiments, the placement instrument engages the prosthesis with a leading edge spacer 1706, or distal spacer. The expandable articulate intervertebral prosthesis comprises an upper support 1702, or superior endplate, and a lower support 1704, or lower endplate. Spacer 1706 can be attached to the upper and lower supports, for example attached with a cable that can be cut. Contralateral placement instrument 1700 comprises an elongate shaft 1710. Elongate shaft 1710 comprises a channel 1712. Shaft 1710 comprises an opening 1718 that exposes and extends to channel 1710. Shaft 1710 comprises a nipple portion near a distal end 1730 that extends between upper support 1702 and lower support 1704 when the insertion tool is connected to spacer 1706. Spacer 1706 limits articulate movement between the upper and lower supports during deployment. Spacer 1706 may be provided as a part or component of a prosthesis assembly for insertion of the prosthesis into the intervertebral space, and spacer 1706 may be connected to shaft 1710.

Shaft 1710 can be connected to the prosthesis upon connection to spacer 1706. Shaft 1710 comprises threads 1714 that engage threads on spacer 1706. In some embodiments, the threads may be positioned on the nipple. Shaft 1710 comprises a shoulder 1716 that engages a shoulder stop 1708 that limits threaded advancement of shaft 17170. Distal end 1730 includes channel 1712 such that the cable can be threaded through shaft 1710 from distal end 1730 to proximal opening 1718. A sleeve 1720, or tube, can be provided that fits over shaft 1710.

In many embodiments, sleeve 1720 may guide shaft 1710. Sleeve 1720 may be sized to fit within an access tube. In many embodiments, shaft 1710 slides inside sleeve 1720, and shaft 1710 may comprise a flange 1719 that slides within sleeve 1720. A channel 1724, or space, can be provided inside sleeve 1720 that allows clearance for flange 1719 while the flange slides inside the sleeve. A screw retained end cap 1722 may be provided on the end of sleeve 1720.

In many embodiments, the trailing edge spacer, or proximal spacer is substantially similar to the trailing edge spacer, or proximal spacer, and the spacers are removably attached to the upper and lower supports. The leading edge spacer and trailing edge spacer can be factory mounted and tied to the upper and lower supports with cable that can be cut, for example nylon gut cable. The elongate members, for example longitudinal rectangular rods, are inserted into their designated slots so as to cut the cable and release the spacers from the supports. In such embodiments, the expanded upper and lower supports can be positioned in the intervertebral space and/or annulus before the upper and lower supports are locked.

An upper channel 1740 and a lower channel 1742 are each adapted to receive an elongate support member. An upper elongate member 1750 is sized to pass through upper channel 1740 formed in at least one component of the upper support. A lower elongate member 1752 is sized to pass through lower channel 1742 formed in at least one component of the lower support. An upper attachment cable 1760 attaches spacer 1706 to upper support 1702. A lower attachment cable 1762 attaches spacer 1706 to lower support 1704. The upper and lower elongate members each comprise a sharpened distal end portion to cut the respective attachment cable. Upper elongate member 1750 comprises a sharpened distal end portion 1758 to cut upper attachment cable 1760.

While the exemplary embodiments have been described in some detail for clarity of understanding and by way of example, a variety of additional modifications, adaptations, and changes may be clear to those of skill in the art. Hence, the scope of the present invention is limited solely by the appended claims.

What is claimed is:

1. A method for introducing a joint assembly to an intervertebral space between a pair of vertebral bodies of a patient, said method comprising:
   introducing upper support components interconnected by pivot joints into a surgical site;
   arranging the upper support components interconnected by the pivot joints in situ into an upper support;
   introducing lower support components into the surgical site; and
   arranging the lower support components in situ into a lower support, wherein the support components are introduced from a posterior approach of the patient and distal components are pivoted about the pivot joints toward proximal components to form the supports and wherein the upper support and the lower support are arranged to articulate with respect to one another, wherein the distal components are inserted at least partially into the intervertebral space before the proximal components, and wherein the upper and lower components each comprise a middle component folded under the proximal component and wherein the distal components are pivoted toward the proximal components before the middle components are unfolded from the proximal components.

2. The method as in claim 1, further comprising attaching the upper support or the lower support to bone anchors.

3. The method as in claim 1, wherein the components of the upper and lower supports are introduced and arranged together.

4. The method as in claim 1, wherein the components of each support are arranged by pivoting one or more elongate components of each support from a first elongate narrow profile configuration to a second wide profile configuration to assemble each support.

5. The method as in claim 4 wherein at least one gear on each support is rotated to pivot the one or more components on each support.

6. The method of claim 1, wherein the lower support components are connected with joints and wherein the lower support components are arranged in situ to form the lower support by articulating the upper support components about the joints.

7. A method for introducing a joint assembly to an intervertebral space between a pair of vertebral bodies of a patient, said method comprising:
   introducing upper support components into a surgical site;
   arranging the upper support components in situ into an upper support;
   introducing lower support components into the surgical site;
   arranging the lower support components in situ into a lower support, wherein the
   support components are introduced from a posterior approach of the patient and distal components are pivoted toward proximal components to form the supports and wherein the upper support and the lower support are arranged to articulate with respect to one another, wherein the upper support components are connected with joints, wherein the upper support components are arranged in situ to form the upper support by articulating the upper support components about the joints, wherein the distal components are inserted at least partially into the intervertebral space before the proximal components, and wherein the upper and lower components each comprise a middle component folded under the proximal component and wherein the distal components are pivoted toward the proximal components before the middle components are unfolded from the proximal components.

8. The method of claim 7, wherein the upper support components are connected to one another by pivot joints prior to introduction into the intervertebral space.

* * * * *